(12) United States Patent
Dai et al.

(10) Patent No.: US 11,691,981 B2
(45) Date of Patent: Jul. 4, 2023

(54) HETEROCYCLIC COMPOUNDS, PREPARATION METHODS THEREFOR, AND METHODS OF USES THEREOF

(71) Applicant: INVENTISBIO CO., LTD., Shanghai (CN)

(72) Inventors: Xing Dai, Short Hills, NJ (US); Yaolin Wang, Short Hills, NJ (US); Yueheng Jiang, Belmont, MA (US); Yanqin Liu, Shanghai (CN); Haotao Niu, Shanghai (CN); Zhenwu Wang, Shanghai (CN); Zixing Han, Shanghai (CN); Liangshan Tao, Shanghai (CN); Jifang Weng, Shanghai (CN); Zhe Shi, Shanghai (CN)

(73) Assignee: INVENTISBIO CO., LTD., Shanghai (CN)

( * ) Notice: Subject to any disclaimer, the term of this patent is extended or adjusted under 35 U.S.C. 154(b) by 0 days.

(21) Appl. No.: 16/910,878

(22) Filed: Jun. 24, 2020

(65) Prior Publication Data

US 2021/0017187 A1 Jan. 21, 2021

(30) Foreign Application Priority Data

Jun. 25, 2019 (WO) ................ PCT/CN2019/092677

(51) Int. Cl.
| | | |
|---|---|---|
| C07D 493/08 | (2006.01) | |
| C07D 401/14 | (2006.01) | |
| C07D 405/14 | (2006.01) | |
| C07D 417/14 | (2006.01) | |
| C07D 487/04 | (2006.01) | |

(52) U.S. Cl.
CPC ......... *C07D 493/08* (2013.01); *C07D 401/14* (2013.01); *C07D 405/14* (2013.01); *C07D 417/14* (2013.01); *C07D 487/04* (2013.01)

(58) Field of Classification Search
CPC .. C07D 493/08; C07D 401/14; C07D 405/14; C07D 417/14; C07D 487/04
See application file for complete search history.

(56) References Cited

U.S. PATENT DOCUMENTS

| 5,707,932 A * | 1/1998 | Kleemann ............... A01N 43/56 546/276.1 |
| 2008/0269293 A1* | 10/2008 | Chi ....................... C07D 403/12 546/276.1 |
| 2009/0048269 A1 | 2/2009 | Finlay et al. |
| 2012/0165332 A1* | 6/2012 | Major .................. C07D 239/48 544/122 |

FOREIGN PATENT DOCUMENTS

| EP | 3150592 A1 | 4/2017 |
| WO | 2007/089512 A1 | 8/2007 |
| WO | 2009/022171 A1 | 2/2009 |
| WO | 2010/146132 A1 | 12/2010 |
| WO | 2014/040555 A1 | 3/2014 |
| WO | 2016/057278 A1 | 4/2016 |
| WO | 2016/106009 A1 | 6/2016 |
| WO | 2018/002217 A1 | 1/2018 |

OTHER PUBLICATIONS

Morgentin et al. Two-Directional Approach for the Rapid Synthesis of 2,4-Bis-Aminoaryl Pyridine Derivatives. Synthetic Communications, vol. 42, 8-24. (Year: 2012).*
International Search Report for corresponding PCT/CN2019/092677, dated Mar. 26, 2020, 7 pages.
Written Opinion for corresponding PCT/CN2019/092677, dated Mar. 20, 2020, 6 pages.
Communication pursuant to Rule 164(1) EPC dated Mar. 1, 2023 for European Application No. 19934626.3.
Ward et al., "Structure-Guided Design of Highly Selective and Potent Covalent Inhibitors of ERKI/2", Journal of Medicinal Chemistry, vol. 58, No. 11, Jun. 11, 2015, pp. 4790-4801 (12 pages), XP055390622.
Tandon et al., "RBxI0080307, a dual EGFR/IGF-IR inhibitor for anticancer therapy", European Journal of Pharmacology, vol. 711, No. 1, Apr. 29, 2013, pp. 19-26 (8 pages), XP028561825.
Mak et al., "A phase Ib 1-10, dose-finding, pharmacokinetic study of the 13-15 focal adhesion kinase inhibitor GSK2256098 and trametinib in patients with advanced solid tumours", British Journal of Cancer, vol. 120, No. 10, Apr. 17, 2019, pp. 975-981(7 pages), XP036822810.
Sallam et al., "Synthesis and antimicrobial activity of some novel substituted pyridazin-3(2H)-ones containing 1,3,4-thiadiazole moiety", Medicinal Chemistry Research, Birkhaeuser, vol. 25, No. 2, Dec. 31, 2015, pp. 369-380 (12 pages), XP035802910.

* cited by examiner

*Primary Examiner* — Sikarl A Witherspoon
(74) *Attorney, Agent, or Firm* — Nixon & Vanderhye, P.C.

(57) ABSTRACT

Provided herein are novel heterocyclic compounds, for example, compounds having Formula I. Also provided herein are methods of preparing the compounds and methods of using the same, for example, in inhibiting TGF-beta mediated signaling and/or for treating cancer.

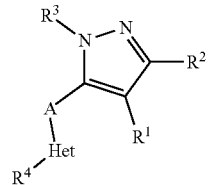

Formula I

21 Claims, No Drawings

HETEROCYCLIC COMPOUNDS, PREPARATION METHODS THEREFOR, AND METHODS OF USES THEREOF

CROSS REFERENCE TO RELATED APPLICATIONS

This application claims priority to International Application No. PCT/CN2019/092677 filed Jun. 25, 2019, the content which is incorporated herein by reference in its entirety.

BACKGROUND OF THE INVENTION

Field of the Invention

In various embodiments, the present invention generally relates to novel heterocyclic compounds, pharmaceutical compositions, methods of preparing, and methods of using, such as for treating cancer.

Background Art

The transforming growth factor β (TGFβ) consists a family of regulatory growth factors and cytokine that have pleiotropic activities in a broad range of tissues and organs. Active TGFβ homodimer binds to heterodimeric TGFβ type I and type receptor complex resulting in phosphorylation of the type I receptor which in turn phosphorylates Smad2 and Smad3 in the cytoplasm. The activation of TGFβ signaling pathway triggers the downstream biologic effects which include cell growth, differentiation and development (Li and Flavell 2008, *Cell*, 134, 392-404, Derynck and Budi, 2019, *Sci. Signal.* 12, eaav5183). Aberrant regulation of the TGF-β signaling pathway is associated with immune disorder that contributes to various diseases such as cancer and fibrosis.

BRIEF SUMMARY OF THE INVENTION

In various embodiments, the present disclosure provides novel compounds. Typically, the compounds herein are TGFβR¹ and/or TGFβRII inhibitors and can inhibit TGF-beta mediated signaling. The compounds herein are useful for treating various diseases or disorders, such as cancer, fibrosis or immune related diseases.

Some embodiments of the present disclosure are directed to a compound of Formula I, II, III, or IV, or a pharmaceutically acceptable salt thereof:

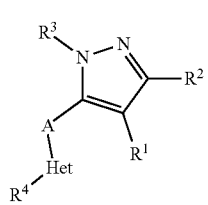

Formula I

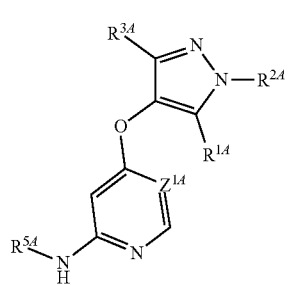

Formula II

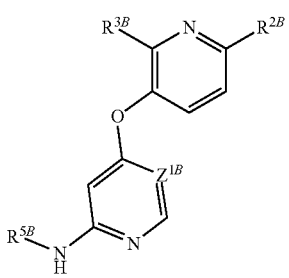

Formula III

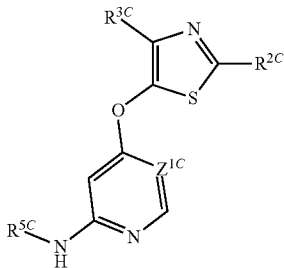

Formula IV wherein the variables are defined herein.

In some embodiments, the compound of Formula I can have a subformula of Formula I-1, I-2, I-3, I-4, or I-5, as defined herein. In some embodiments, the compound of Formula II can have a subformula of Formula II-1, II-2, II-3, II-4, II-5, II-6, or II-7, as defined herein. In some embodiments, the compound of Formula III can have a subformula of Formula III-1 III-2, or III-3, as defined herein. In some embodiments, the present disclosure provides a compound selected from any of Compound Nos. 1-90, or a pharmaceutically acceptable salt thereof.

Certain embodiments of the present disclosure are directed to a pharmaceutical composition comprising one or more of the compounds of the present disclosure (e.g., a compound of Formula I (e.g., Formula I-1, I-2, I-3, I-4, or I-5), Formula II (e.g., Formula II-1, II-2, II-3, II-4, II-5, II-6, or II-7), Formula II-S, Formula III (e.g., Formula III-1, III-2, or III-3), Formula III-S, Formula IV, or any of Compound Nos. 1-90, or a pharmaceutically acceptable salt thereof) and optionally a pharmaceutically acceptable excipient. The pharmaceutical composition described herein can be formulated for different routes of administration, such as oral administration, parenteral administration, or inhalation etc.

Some embodiments of the present disclosure are also directed to a method of treating cancer in a subject in need thereof. In some embodiments, the method comprises administering a therapeutically effective amount of a compound of the present disclosure (e.g., a compound of any of Formula I (e.g., Formula I-1, I-2, I-3, I-4, or I-5), Formula II (e.g., Formula II-1, II-2, II-3, II-4, II-5, II-6, or II-7), Formula II-S, Formula III (e.g., Formula III-1, III-2, or III-3), Formula III-S, Formula IV, or any of Compound Nos. 1-90, or a pharmaceutically acceptable salt thereof) or a therapeutically effective amount of a pharmaceutical composition described herein.

It is to be understood that both the foregoing summary and the following detailed description are exemplary and explanatory only, and are not restrictive of the invention herein.

DETAILED DESCRIPTION OF THE INVENTION

Typically, the novel compounds described herein are useful in modulating TGF-beta mediated signaling and can be used for treating or preventing diseases or disorders such as cancer. As detailed herein, the novel compounds herein can inhibit TGFβR1 and/or TGFβR2 kinase activities with high potency, selectivity, and with desirable pharmacokinetic profiles.

Compounds

Compounds of the present disclosure typically have a pyrrazole core (e.g., Formula I, II, or II-S), a pyridine core (e.g., Formula III), or a thiazole core (e.g., Formula IV). As detailed herein, while substituents for the different core structures appear similar, each of these core structures can provide a unique structure and activity relationship.

Formula I

Some embodiments of the present disclosure provide a compound of Formula I, or a pharmaceutically acceptable salt thereof:

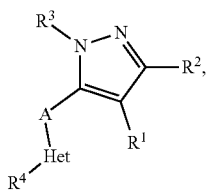

Formula I wherein:

A is O or NH;

Het is an optionally substituted heteroaryl;

$R^1$ and $R^2$ are each independently hydrogen, halogen, —CN, —CO-$G^1$, —$SO_2$-$G^1$, —$NR^{10}R^{11}$, —O—$R^{20}$, an optionally substituted alkyl, an optionally substituted alkenyl, an optionally substituted alkynyl, an optionally substituted carbocyclic ring (e.g., $C_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl);

or $R^1$ and $R^2$ together form an optionally substituted phenyl, an optionally substituted heteroaryl, an optionally substituted carbocyclic or heterocyclic ring, e.g., an optionally substituted 5-8 membered carbocyclic, or an optionally substituted 5-8 membered heterocyclic ring;

$R^3$ is hydrogen, a nitrogen protecting group, an optionally substituted alkyl, an optionally substituted carbocyclic ring (e.g., $C_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl);

$R^4$ is hydrogen, halogen, or —$NHR^5$, wherein $R^5$ is hydrogen, a nitrogen protecting group, an optionally substituted alkyl, an optionally substituted carbocyclic ring (e.g., $C_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl);

wherein $G^1$ at each occurrence is independently hydrogen, —$NR^{10}R^{11}$, —O—$R^{20}$, an optionally substituted alkyl, an optionally substituted alkenyl, an optionally substituted alkynyl, an optionally substituted carbocyclic ring (e.g., $C_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl);

wherein each of $R^{10}$ and $R^{11}$ at each occurrence is independently hydrogen, a nitrogen protecting group, an optionally substituted alkyl, an optionally substituted alkenyl, an optionally substituted alkynyl, an optionally substituted carbocyclic ring (e.g., $C_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl); or $R^{10}$ and $R^{11}$ together form an optionally substituted heterocyclic or heteroaryl ring, e.g., an optionally substituted 5-7 membered heterocyclic or an optionally substituted 5-10 membered heteroaryl; and wherein $R^{20}$ at each occurrence is independently hydrogen, an oxygen protecting group, an optionally substituted alkyl, an optionally substituted alkenyl, an optionally substituted alkynyl, an optionally substituted carbocyclic ring (e.g., $C_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl).

Typically, A in Formula I is oxygen and the Het in Formula I is an optionally substituted 5 or 6 membered heteroaryl having 1 or 2 ring nitrogens, such as pyridyl or pyrimidinyl.

In a typical embodiment, the compound of Formula I can be characterized by Formula I-1:

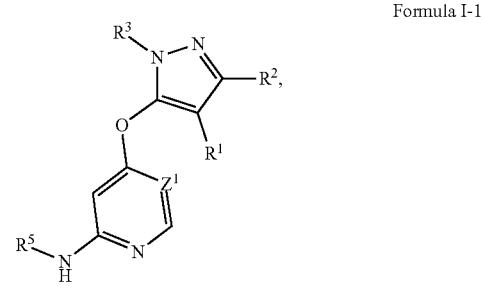

Formula I-1 wherein $Z^1$ is CH or N, wherein R, $R^2$, $R^3$, and $R^5$ are defined herein.

In some preferred embodiments, $R^1$ in Formula I is hydrogen. For example, in some embodiments, the compound of Formula I can be characterized by Formula I-2:

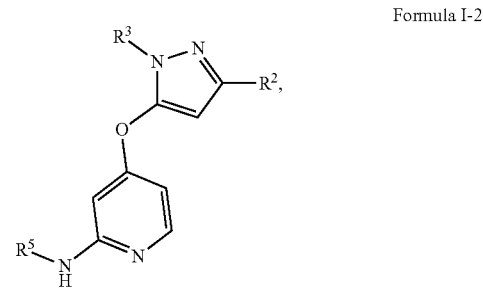

Formula I-2 wherein $R^2$, $R^3$, and $R^5$ are defined herein. In some embodiments, $R^1$ in Formula I is not hydrogen. In some embodiments, $R^1$ and $R^2$ can together form an optionally substituted phenyl, an optionally substituted heteroaryl (e.g., as described herein), an optionally substituted 5-8 membered carbocyclic (e.g., 5 or 6 membered carbocyclic), or an optionally substituted 5-8 membered heterocyclic ring (e.g., 5 or 6 membered heterocyclic ring).

$R^4$ in Formula I is typically —NH—$R^5$, although in some embodiments, $R^4$ can be hydrogen or halogen, which can for example serve as a synthetic intermediate.

In some preferred embodiments, the compound of Formula I can be characterized by Formula I-3, I-4, or I-5:

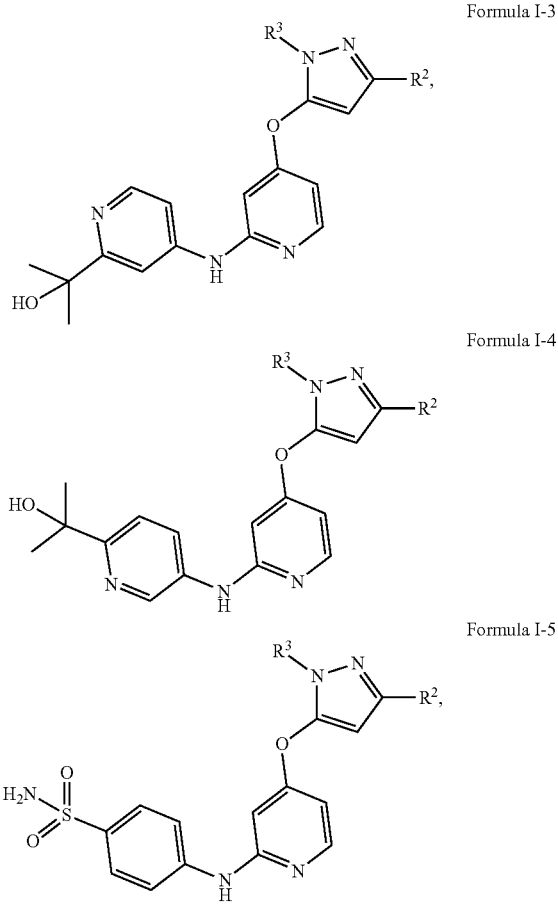

Formula I-3

Formula I-4

Formula I-5 wherein $R^2$ and $R^3$ are defined herein.

Various groups suitable for $R^2$ are described herein, which include for example a halogen, optionally substituted alkyl, carbocyclic ring, heterocyclyl, phenyl, or heteroaryl.

In some embodiments, $R^2$ can be a halogen, such as F, Cl, or Br.

In some embodiments, $R^2$ can be an optionally substituted alkyl group, such as optionally substituted $C_{1-6}$ alkyl or $C_{1-4}$ alkyl. For example, in some embodiments, $R^2$ can be an unsubstituted $C_{1-4}$ alkyl, such as methyl, ethyl, isopropyl, tert-butyl. In some embodiments, $R^2$ can be a $C_{1-4}$ alkyl optionally substituted with 1-3 substituents independently selected from F, $C_{1-4}$ alkyl, and $C_{1-4}$ alkoxy, for example, $R^2$ can be —CHF$_2$, —CF$_3$, —CH$_2$—CHF$_2$ or —CH$_2$—CF$_3$.

Carbocyclic rings can also be suitable $R^2$ groups. In some embodiments, $R^2$ can be an optionally substituted saturated carbocyclic ring. For example, in some embodiments, $R^2$ can be an optionally substituted cycloalkyl, such as an optionally substituted $C_{3-4}$ cycloalkyl. In some embodiments, $R^2$ can be an unsubstituted $C_{3-6}$ cycloalkyl, e.g., cyclopropyl, cyclobutyl, cyclopentyl, etc.

In some embodiments, $R^2$ can be an optionally substituted heterocyclic ring. Typically, the heterocyclic ring is a monocyclic ring containing one or two ring heteroatoms each independently O, S, or N. Those skilled in the art would appreciate that typically, the heterocyclic ring does not include O—O, O—S, S—S, O—N, S—N bond. Preferably, when present, only one O or S atom is present. Non-limiting suitable examples of heterocyclic rings include the following, each of which can be optionally substituted:

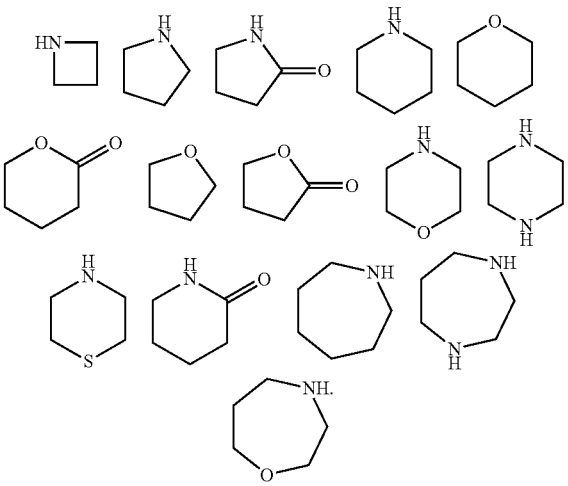

In some embodiments, the heterocyclic ring can also be a bicyclic or polycyclic ring. Examples of such heterocyclic rings are described herein. When present, the heterocyclic ring can be attached to the remainder of the molecule via any of the available attaching points, including an available ring nitrogen atom. In some embodiments, the heterocyclic ring is unsubstituted. In some embodiments, the heterocyclic ring is optionally substituted with 1-3 substituents independently selected from F, $C_{1-4}$ alkyl, and $C_{1-4}$ alkoxy.

In some embodiments, $R^2$ can be an optionally substituted alkoxy, such as an optionally substituted $C_{1-4}$ alkoxy. For example, in some embodiments, $R^2$ can be an unsubstituted $C_{1-4}$ alkoxy or a $C_{1-4}$ alkoxy optionally substituted with 1-3 substituents independently selected from F, $C_{1-4}$ alkyl, and $C_{1-4}$ alkoxy. In some embodiments, $R^2$ can be an optionally substituted cycloalkoxy, such as an optionally substituted $C_{3-6}$ cycloalkoxy. For example, in some embodiments, $R^2$ can be an unsubstituted $C_{3-6}$ cycloalkoxy or a $C_{3-6}$ cycloalkoxy optionally substituted with 1-3 substituents independently selected from F, $C_{1-4}$ alkyl, and $C_{1-4}$ alkoxy.

In some embodiments, $R^2$ can be an optionally substituted aryl, such as an optionally substituted phenyl. For example, in some embodiments, $R^2$ can be an unsubstituted phenyl or a phenyl optionally substituted with 1-3 substituents independently selected from halogen (e.g., F), —CN, $C_{1-4}$ alkyl, fluorine substituted $C_{1-4}$ alkyl (e.g., CF$_3$), $C_{1-4}$ alkoxy, and fluorine substituted $C_{1-4}$ alkoxy.

In some embodiments, $R^2$ can be an optionally substituted heteroaryl, such as an optionally substituted 5 or 6 membered heteroaryl. Typically, the heteroaryl is a monocyclic ring containing 1-3 ring heteroatoms each independently O, S, or N. Those skilled in the art would understand that typically, the monocyclic heteroaryl contains at most one ring atom that is O or S. Non-limiting suitable examples of heteroaryl include the following, each of which can be optionally substituted:

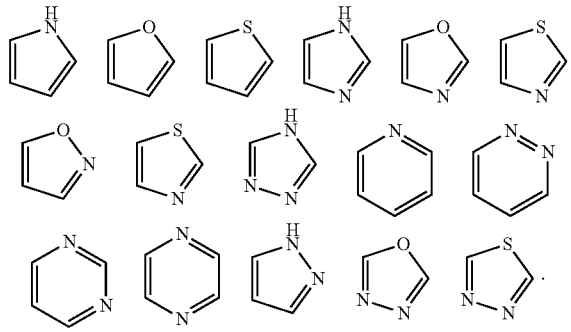

When present, the heteroaryl can be attached to the remainder of the molecule via any of the available attaching points, including an available ring nitrogen atom. In some embodiments, the heteroaryl is unsubstituted. In some embodiments, the heteroaryl is optionally substituted with 1-3 substituents independently selected from halogen (e.g., F), —CN, $C_{1-4}$ alkyl, fluorine substituted $C_{1-4}$ alkyl (e.g., $CF_3$), $C_{1-4}$ alkoxy, and fluorine substituted $C_{1-4}$ alkoxy.

Typically, $R^2$ in Formula I (including subformulae I-1, I-2, I-3, I-4, and I-5) can be selected from halogen, an optionally substituted $C_{1-4}$ alkyl, an optionally substituted $C_{3-6}$ cycloalkyl, an optionally substituted 4-8 membered heterocyclyl, an optionally substituted $C_{1-4}$ alkoxy, an optionally substituted $C_{3-6}$ cycloalkoxy, an optionally substituted phenyl, and an optionally substituted 5 or 6 membered heteroaryl. In some embodiments, the optionally substituted $C_{1-4}$ alkyl, $C_{3-4}$ cycloalkyl, 4-8 membered heterocyclyl, $C_{1-4}$ alkoxy or $C_{3-6}$ cycloalkoxy is optionally substituted with 1-3 substituents independently selected from F, $C_{1-6}$ alkyl, and $C_{1-4}$ alkoxy; and the optionally substituted phenyl, or 5 or 6 membered heteroaryl is optionally substituted with 1-3 substituents independently selected from halogen (e.g., F), —CN, $C_{1-4}$ alkyl, fluorine substituted $C_{1-4}$ alkyl, $C_{1-4}$ alkoxy, and fluorine substituted $C_{1-4}$ alkoxy.

In some preferred embodiments, $R^2$ is selected from a $C_{1-4}$ alkyl optionally substituted with 1-3 fluorine; a $C_{1-4}$ alkoxy optionally substituted with 1-3 fluorine; and a $C_{3-4}$ cycloalkyl optionally substituted with 1-3 substituents independently selected from fluorine and methyl.

In some preferred embodiments, $R^2$ is selected from methyl, ethyl, isopropyl, methoxy, —$CHF_2$, —$CF_3$, cyclopropyl, cyclobutyl, cyclopentyl, —$CH_2$—$CHF_2$ and —$CH_2$—$CF_3$.

Various groups suitable for $R^3$ are described herein, which include for example an optionally substituted alkyl, carbocyclic ring, heterocyclyl, phenyl, or heteroaryl.

In some embodiments, $R^3$ can be an optionally substituted alkyl group, such as optionally substituted $C_{1-6}$ alkyl or $C_{1-4}$ alkyl. For example, in some embodiments, $R^3$ can be an unsubstituted $C_{1-4}$ alkyl, such as methyl, ethyl, isopropyl, tert-butyl. In some embodiments, $R^3$ can be a $C_{1-4}$ alkyl optionally substituted with 1-3 substituents independently selected from F, $C_{1-4}$ alkyl, and $C_{1-4}$ alkoxy, for example, $R^3$ can be —$CHF_2$, —$CF_3$, —$CH_2$—$CHF_2$, or —$CH_2$—$CF_3$. In some embodiments, $R^3$ can be a $C_{1-4}$ alkyl substituted with one $C_{3-6}$ cycloalkyl, i.e., —$C_{1-4}$ alkyl-($C_{3-4}$ cycloalkyl), which can be further optionally substituted, at either or both of the $C_{1-4}$ alkyl and $C_{3-4}$ cycloalkyl, with 1-3 substituents independently selected from F, $C_{1-4}$ alkyl, and $C_{1-4}$ alkoxy. For example, in some embodiments, $R^3$ can be

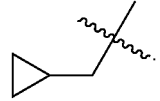

In some embodiments, $R^3$ can also be a $C_{1-4}$ alkyl substituted with one heterocyclyl (e.g., described herein), which can be further optionally substituted, at either or both of the $C_{1-4}$ alkyl and the heterocyclyl, with 1-3 substituents independently selected from F, $C_{1-4}$ alkyl, and $C_{1-4}$ alkoxy. In some embodiments, $R^3$ can also be an optionally substituted aralkyl (e.g., benzyl, phenylethyl, etc.) or optionally substituted heteroaralkyl (e.g., a $C_{1-4}$ alkyl substituted with a 5 or 6-membered heteroaryl).

Carbocyclic rings can also be suitable $R^3$ groups. In some embodiments, $R^3$ can be an optionally substituted saturated carbocyclic ring. For example, in some embodiments, $R^3$ can be an optionally substituted cycloalkyl, such as an optionally substituted $C_{3-4}$ cycloalkyl. In some embodiments, $R^3$ can be an unsubstituted $C_{3-6}$ cycloalkyl, e.g., cyclopropyl, cyclobutyl, cyclopentyl, etc. In some embodiments, $R^3$ can be a $C_{3-6}$ cycloalkyl optionally substituted with 1-3 substituents independently selected from F, $C_{1-4}$ alkyl (e.g., methyl), and $C_{1-4}$ alkoxy.

In some embodiments, $R^3$ can be an optionally substituted heterocyclic ring. Typically, the heterocyclic ring contains one or two ring heteroatoms each independently O, S, or N. Non-limiting suitable examples of heterocyclic rings include the following, each of which can be optionally substituted:

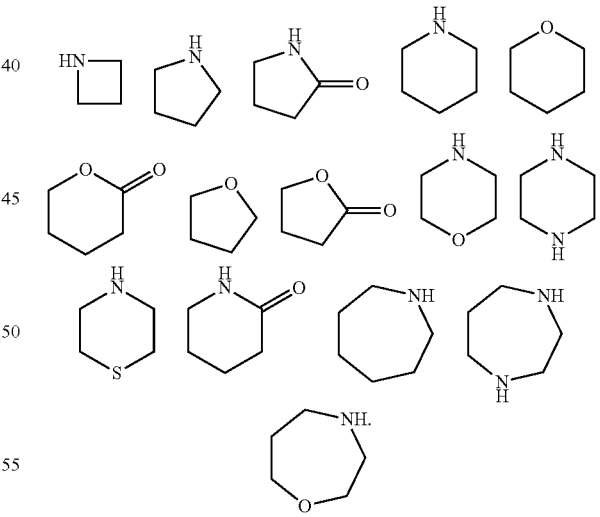

In some embodiments, the heterocyclic ring can also be a bicyclic or polycyclic ring. Examples of such heterocyclic rings are described herein. When present, the heterocyclic ring can be attached to the remainder of the molecule via any of the available attaching points, including an available ring nitrogen atom. In some embodiments, the heterocyclic ring is unsubstituted. In some embodiments, the heterocyclic ring is optionally substituted with 1-3 substituents independently selected from F and $C_{1-4}$ alkyl.

In some embodiments, R³ can be an optionally substituted aryl, such as an optionally substituted phenyl. For example, in some embodiments, R³ can be an unsubstituted phenyl or a phenyl optionally substituted with 1-3 substituents independently selected from halogen (e.g., F), —CN, $C_{1-4}$ alkyl, fluorine substituted $C_{1-4}$ alkyl (e.g., $CF_3$), $C_{1-4}$ alkoxy, and fluorine substituted $C_{1-4}$ alkoxy.

In some embodiments, R³ can be an optionally substituted heteroaryl, such as an optionally substituted 5 or 6 membered heteroaryl. Typically, the heteroaryl is a monocyclic ring containing 1-3 ring heteroatoms each independently O, S, or N. Non-limiting suitable examples of heteroaryl include the following, each of which can be optionally substituted:

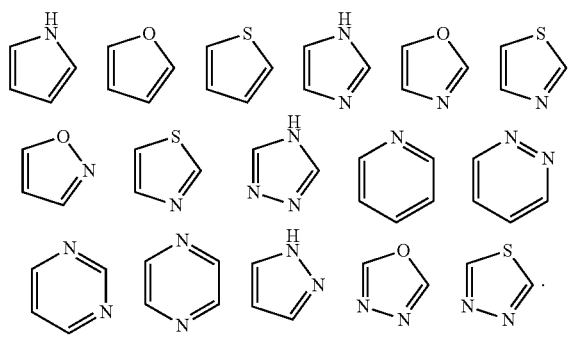

When present, the heteroaryl can be attached to the remainder of the molecule via any of the available attaching points, including an available ring nitrogen atom. In some embodiments, the heteroaryl is unsubstituted. In some embodiments, the heteroaryl is optionally substituted with 1-3 substituents independently selected from halogen (e.g., F), —CN, $C_{1-4}$ alkyl, fluorine substituted $C_{1-4}$ alkyl (e.g., $CF_3$), $C_{1-4}$ alkoxy, and fluorine substituted $C_{1-4}$ alkoxy.

Typically, R³ in Formula I (including subformulae I-1, I-2, I-3, I-4, and I-5) is selected from an optionally substituted $C_{1-4}$ alkyl, an optionally substituted $C_{3-6}$ cycloalkyl, an optionally substituted 4-8 membered heterocyclyl (e.g., described herein), an optionally substituted phenyl, and an optionally substituted 5 or 6 membered heteroaryl (e.g., described herein). For example, in some embodiments, R³ is a $C_{1-4}$ alkyl optionally substituted with 1-3 fluorine; a $C_{3-6}$ cycloalkyl optionally substituted with 1-3 substituents independently selected from fluorine and $C_{1-4}$ alkyl (e.g., methyl); or a 4-8 membered heterocyclyl optionally substituted with 1-3 substituents independently selected from fluorine and $C_{1-4}$ alkyl (e.g., methyl). In some embodiments, R³ is a $C_{1-4}$ alkyl substituted with one $C_{3-4}$ cycloalkyl, i.e., —$C_{1-4}$ alkyl-($C_{3-4}$ cycloalkyl), which can be further optionally substituted. In some embodiments, R³ is a phenyl optionally substituted with 1-3 substituents independently selected from halogen (e.g., F), —CN, $C_{1-4}$ alkyl, fluorine substituted $C_{1-4}$ alkyl, $C_{1-4}$ alkoxy, and fluorine substituted $C_{1-4}$ alkoxy; or a 5 or 6 membered heteroaryl (e.g., described herein) optionally substituted with 1-3 substituents independently selected from halogen (e.g., F), —CN, $C_{1-4}$ alkyl, fluorine substituted $C_{1-4}$ alkyl, $C_{1-4}$ alkoxy, and fluorine substituted $C_{1-4}$ alkoxy.

In some preferred embodiments R³ can be methyl, ethyl, isopropyl, tert-butyl, —$CHF_2$, —$CF_3$, —$CH_2$—$CHF_2$, —$CH_2$—$CF_3$,

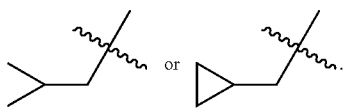

In some preferred embodiments, R³ can be selected from:

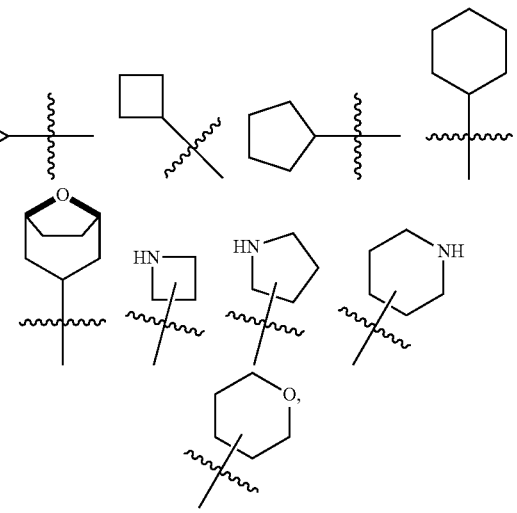

each of which is optionally substituted, for example, with 1 or 2 substituents independently selected from F and methyl.

In some more specific embodiments, R³ can be selected from:

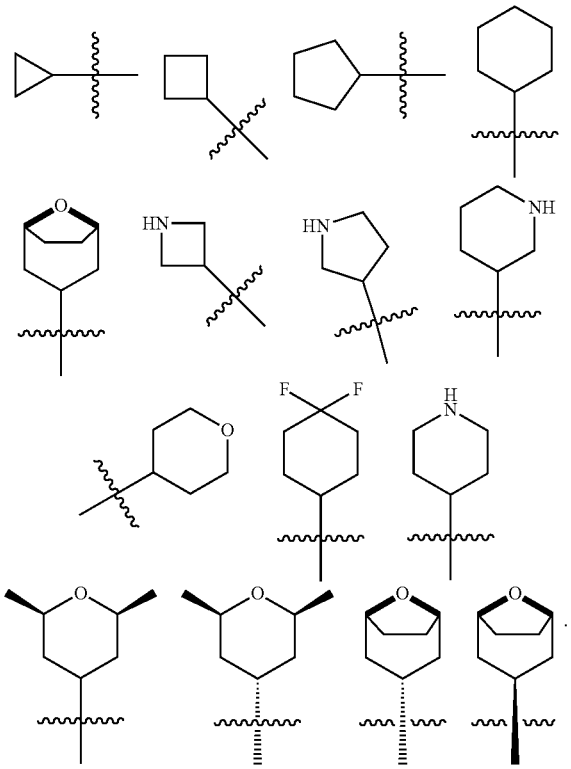

In some preferred embodiments, $R^3$ can be

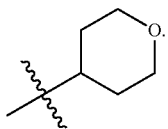 [SMILES: *C1CCOCC1]

In some preferred embodiments, $R^3$ can be select from:

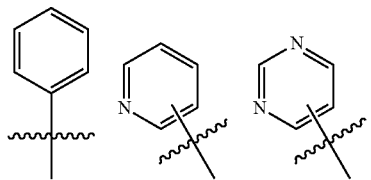

each of which is optionally substituted, for example, with 1 or 2 substituents independently selected from F, Cl, methyl, and CN.

In some more specific embodiments, $R^3$ is selected from

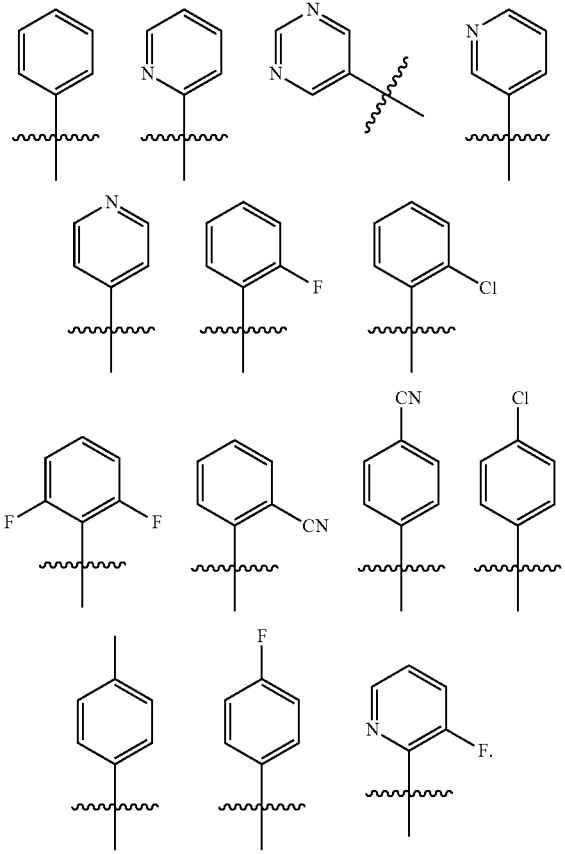

$R^4$ in Formula I is typically —NH—$R^5$, although in some embodiments, $R^4$ can be hydrogen or halogen, which can for example serve as a synthetic intermediate.

Various suitable $R^5$ groups are described herein. For example, in some embodiments, $R^5$ is selected from:

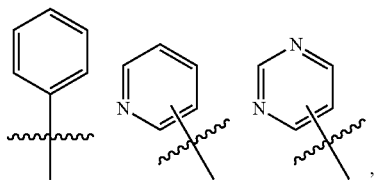

each of which is substituted with one substituent selected from,

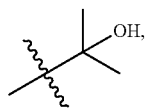 [SMILES: *C(C)(C)O]

—$CONH_2$, and

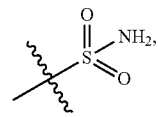 [SMILES: *S(N)(=O)=O]

and further optionally substituted. The phenyl, pyridyl, or pyrimidinyl can connect to the remainder of the molecule via any of the available attaching points, and the one substituent can be ortho, meta, or para to the connection. For example, in some embodiments, $R^5$ can be:

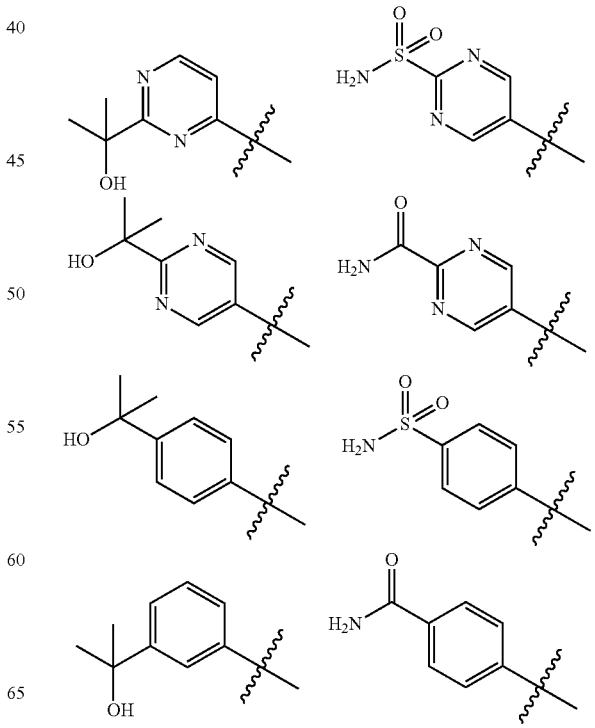

-continued

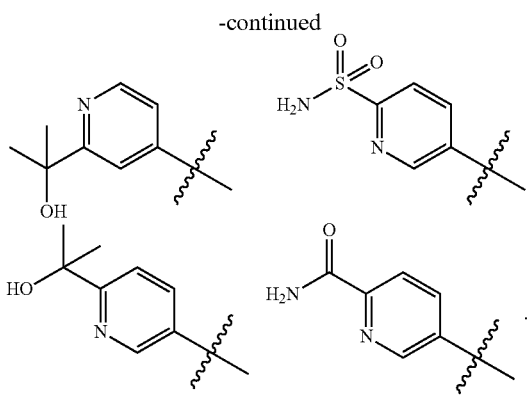

In some embodiments, $R^5$ groups can be an optionally substituted phenyl. In some embodiments, two adjacent substituents can join together to form an optionally substituted carbocyclic or heterocyclic ring, typically a 5 or 6 membered ring. For example, in some embodiments, $R^5$ can be selected from:

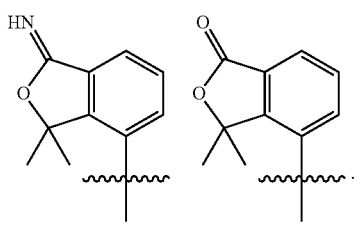

Formula II

Some embodiments of the present disclosure are directed to compounds of Formula II, or a pharmaceutically acceptable salt thereof:

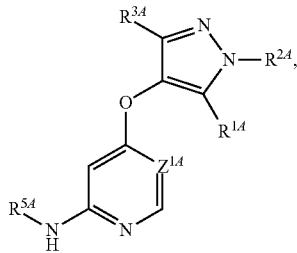

Formula II wherein the variables $R^{1A}$, $R^{2A}$, $R^{3A}$, and $Z^{1A}$ are defined herein.

Typically, in Formula II,
$R^{1A}$ is hydrogen, halogen, or an optionally substituted $C_{1-4}$ alkyl;
$R^{2A}$ is —$CH_2CF_3$ or $C_{4-6}$ cycloalkyl, wherein the $C_{4-6}$ cycloalkyl is optionally substituted with 1-3 substituents independently selected from fluorine and methyl;
or $R^{1A}$ and $R^{2A}$ together form an optionally substituted heteroaryl, or an optionally substituted heterocyclic ring, e.g., an optionally substituted 5-8 membered heterocyclic ring;
$R^{3A}$ is hydrogen, halogen, —CN, —CO-$G^1$, —$SO_2$-G, —$NR^{10}R^{11}$, —O—$R^{20}$, an optionally substituted alkyl, an optionally substituted alkenyl, an optionally substituted alkynyl, an optionally substituted carbocyclic ring (e.g., $C_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl);

$Z^{1A}$ is N or CH;

$R^{5A}$ is hydrogen, a nitrogen protecting group, an optionally substituted alkyl, an optionally substituted carbocyclic ring (e.g., $C_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl);

wherein $G^1$ at each occurrence is independently hydrogen, —$NR^{10}R^{11}$, —O—$R^{20}$, an optionally substituted alkyl, an optionally substituted alkenyl, an optionally substituted alkynyl, an optionally substituted carbocyclic ring (e.g., $C_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl); wherein each of $R^{10}$ and $R^{11}$ at each occurrence is independently hydrogen, a nitrogen protecting group, an optionally substituted alkyl, an optionally substituted alkenyl, an optionally substituted alkynyl, an optionally substituted carbocyclic ring (e.g., $C_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl); or $R^{10}$ and $R^{11}$ together form an optionally substituted heterocyclic or heteroaryl ring, e.g., an optionally substituted 5-7 membered heterocyclic or an optionally substituted 5-10 membered heteroaryl; and wherein $R^{20}$ at each occurrence is independently hydrogen, an oxygen protecting group, an optionally substituted alkyl, an optionally substituted alkenyl, an optionally substituted alkynyl, an optionally substituted carbocyclic ring (e.g., $C_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl).

In some preferred embodiments, $R^{1A}$ in Formula II is hydrogen.

In some embodiments, $R^{1A}$ and $R^{2A}$ can together form an optionally substituted heteroaryl (e.g., as described herein), or an optionally substituted 5-8 membered heterocyclic ring (e.g., 5 or 6 membered heterocyclic ring). For example, in some embodiments, the compound of Formula II is characterized as having Formula II-1:

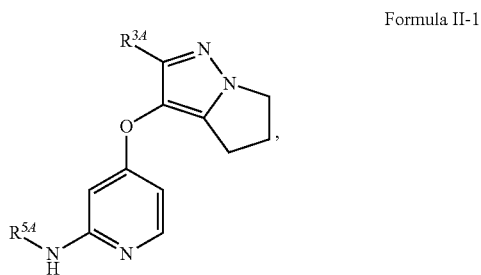

Formula II-1 wherein $R^{3A}$ and $R^{5A}$ are defined herein.

In some embodiments, the compound of Formula II is characterized as having Formula II-2, II-3, II-4, II-5, II-6, or II-7:

Formula II-2

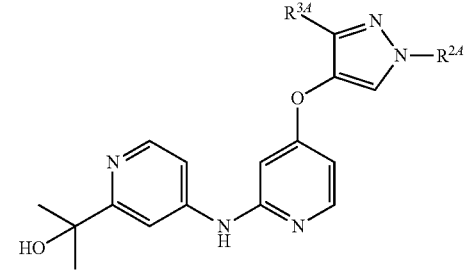

Formula II-3

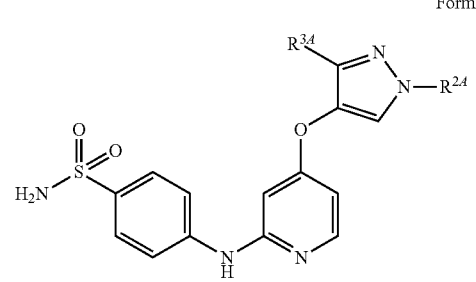

Formula II-4

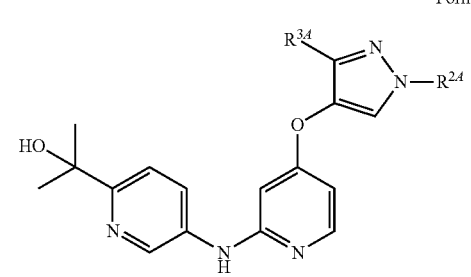

Formula II-5

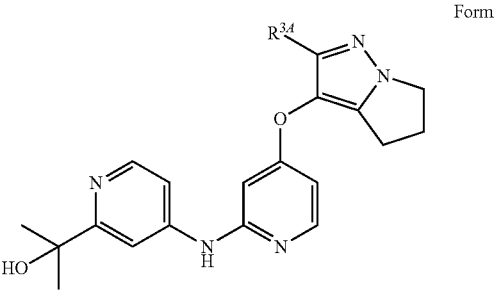

Formula II-6

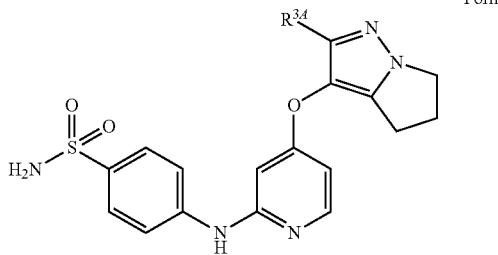

Formula II-7

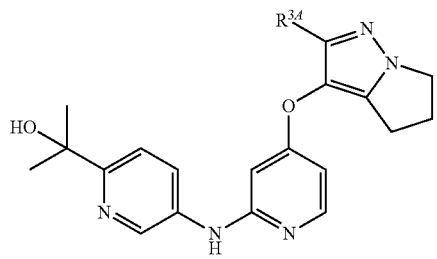

wherein $R^{2A}$ and $R^{3A}$ are defined herein.

In some embodiments, $R^{2A}$ can be —CH$_2$CF$_3$. In some embodiments, $R^{2A}$ can be cyclobutyl optionally substituted with 1 or 2 substituents independently selected from fluorine and methyl. In some embodiments, $R^2$ can be cyclopentyl optionally substituted with 1 or 2 substituents independently selected from fluorine and methyl.

Various suitable groups for $R^{3A}$ are described herein. In some embodiments, $R^{3A}$ can be halogen (e.g., F, Cl, or Br). In some embodiments, $R^{3A}$ can be any of those described herein for $R^3$ in the context of Formula I. For example, in some embodiments, $R^{3A}$ in Formula II (including subformulae II-1, II-2, II-3, II-4, II-5, II-6, and II-7) can be selected from an optionally substituted $C_{1-4}$ alkyl, an optionally substituted $C_{3-4}$ cycloalkyl, an optionally substituted 4-8 membered heterocyclyl (e.g., described herein), an optionally substituted phenyl, and an optionally substituted 5 or 6 membered heteroaryl (e.g., described herein). In some embodiments, $R^{3A}$ is a $C_{1-4}$ alkyl optionally substituted with 1-3 fluorine; a $C_{3-6}$ cycloalkyl optionally substituted with 1-3 substituents independently selected from fluorine and $C_{1-4}$ alkyl (e.g., methyl); or a 4-8 membered heterocyclyl optionally substituted with 1-3 substituents independently selected from fluorine and $C_{1-4}$ alkyl (e.g., methyl). In some embodiments, $R^{3A}$ is a $C_{1-4}$ alkyl substituted with one $C_{3-6}$ cycloalkyl, i.e., —$C_{1-4}$ alkyl-($C_{3-6}$ cycloalkyl), which can be further optionally substituted. In some embodiments, $R^{3A}$ is a phenyl optionally substituted with 1-3 substituents independently selected from halogen (e.g., F), —CN, $C_{1-4}$ alkyl, fluorine substituted $C_{1-4}$ alkyl, $C_{1-4}$ alkoxy, and fluorine substituted $C_{1-4}$ alkoxy; or a 5 or 6 membered heteroaryl (e.g., described herein) optionally substituted with 1-3 substituents independently selected from halogen (e.g., F), —CN, $C_{1-4}$ alkyl, fluorine substituted $C_{1-4}$ alkyl, $C_{1-4}$ alkoxy, and fluorine substituted $C_{1-4}$ alkoxy.

In some preferred embodiments, $R^{3A}$ can be methyl, ethyl, isopropyl, tert-butyl, —CHF$_2$, —CF$_3$, —CH$_2$—CHF$_2$, —CH$_2$—CF$_3$,

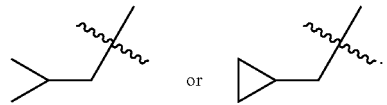

In some preferred embodiments, $R^{3A}$ can be selected from:

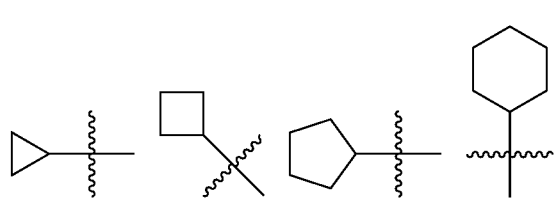

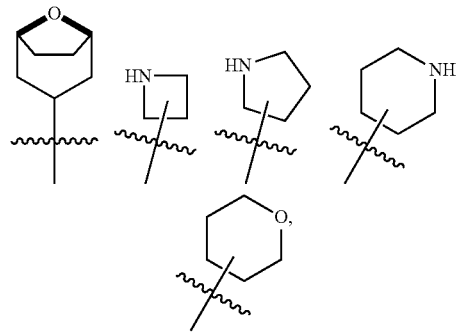

each of which is optionally substituted, for example, with 1 or 2 substituents independently selected from F and methyl.

In some more specific embodiments, $R^{3A}$ can be selected from:

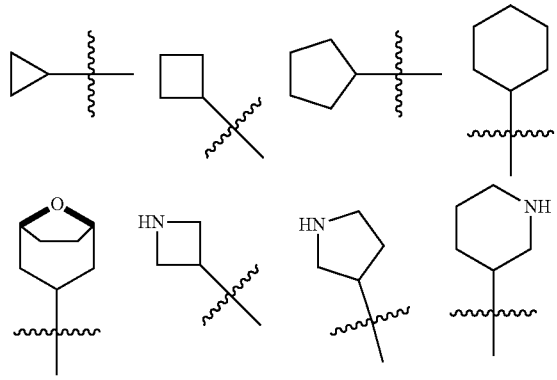

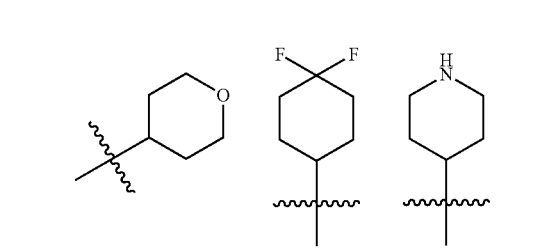

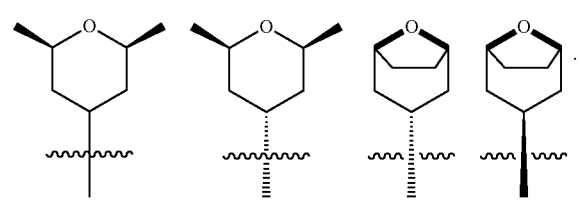

In some preferred embodiments, $R^{3A}$ can be

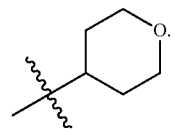 [SMILES: *C1CCOCC1]

In some embodiments, $R^{3A}$ can be selected from:

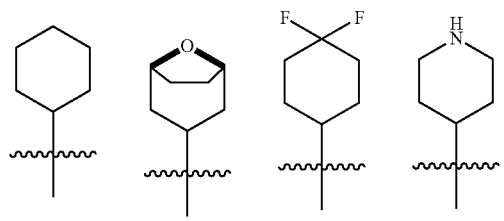

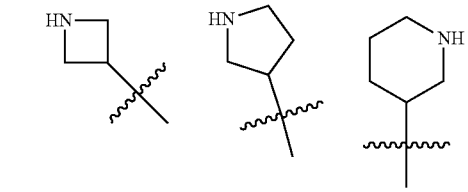

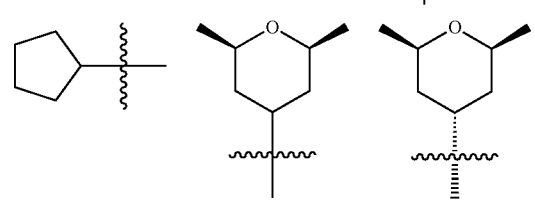

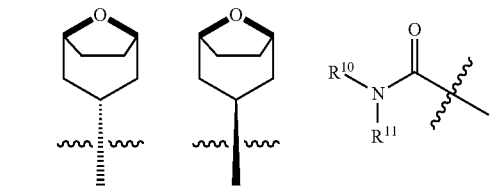

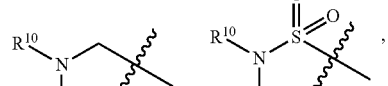

wherein $R^{10}$ and $R^{11}$ are defined herein. For example, in some embodiments, one of $R^{10}$ and $R^{11}$ can be hydrogen or a nitrogen protecting group, and the other of $R^{10}$ and $R^{11}$ can be an optionally substituted $C_{1-6}$ alkyl, optionally substituted $C_{3-6}$ cycloalkyl, optionally substituted 4-8 membered heterocyclyl, optionally substituted phenyl, or optionally substituted 5 or 6 membered heteroaryl. In some embodiments, the optionally substituted $C_{1-6}$ alkyl, $C_{3-4}$ cycloalkyl, or 4-8 membered heterocyclyl, can be optionally substituted with 1-3 substituents independently selected from F, $C_{1-4}$ alkyl, and $C_{1-4}$ alkoxy; and the optionally substituted phenyl, or 5 or 6 membered heteroaryl is optionally substituted with 1-3 substituents independently selected from halogen (e.g., F), —CN, $C_{1-4}$ alkyl, fluorine substituted $C_{1-4}$ alkyl, $C_{1-4}$ alkoxy, and fluorine substituted $C_{1-4}$ alkoxy.

In some preferred embodiments, $R^{3A}$ can be selected from:

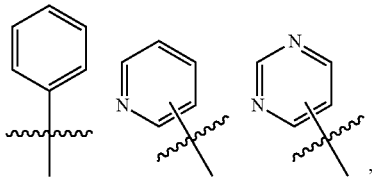

each of which is optionally substituted, for example, with 1 or 2 substituents independently selected from F, Cl, methyl, and CN.

In some more specific embodiments, $R^{3A}$ is an optionally substituted phenyl or heteroaryl selected from

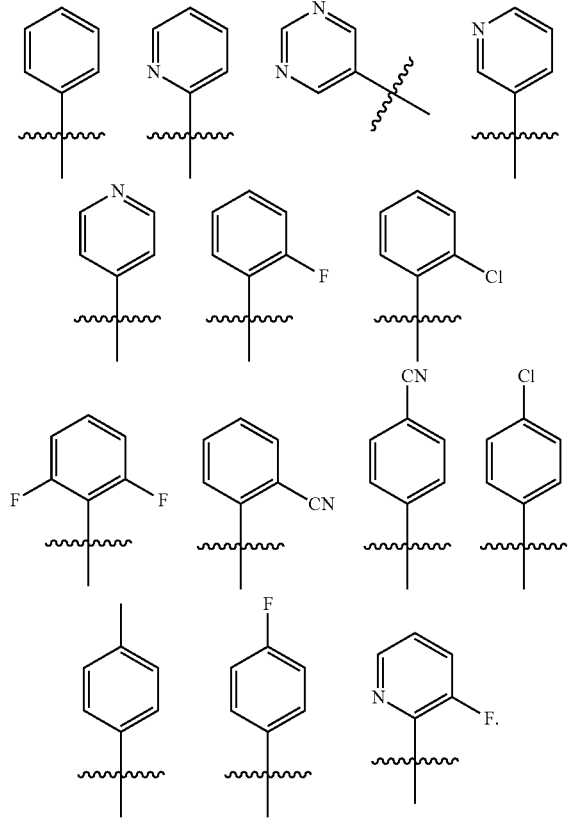

Various suitable groups for $R^{5A}$ are described herein, which includes any of those described herein for $R^5$ in the context of Formula I. For example, in some embodiments, $R^{5A}$ is selected from:

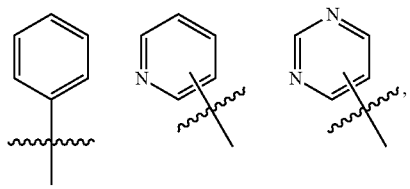

each of which is substituted with one substituent selected from

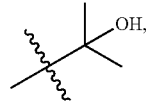

—CONH$_2$, and

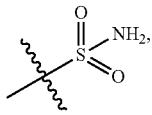

and further optionally substituted. In some embodiments, $R^{5A}$ can be selected from:

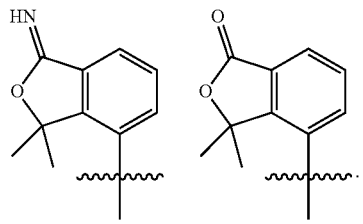

Typically, $R^{2A}$ in Formula II is —CH$_2$CF$_3$ or C$_{4-6}$ cycloalkyl, wherein the C$_{4-6}$ cycloalkyl is optionally substituted with 1-3 substituents independently selected from fluorine and methyl. In some embodiments, provided that one of 1)-3) and/or one or 4) and 5) is true:
1) $R^{3A}$ is an optionally substituted phenyl;
2) $R^{3A}$ is an optionally substituted 4-pyridyl, optionally substituted 3-pyridyl, substituted 2-pyridyl, optionally substituted pyrimidinyl, or optionally substituted 5-membered heteroaryl; examples of suitable substituents include F, methyl, Cl, —CN, etc.;
3) $R^{3A}$ is selected from:

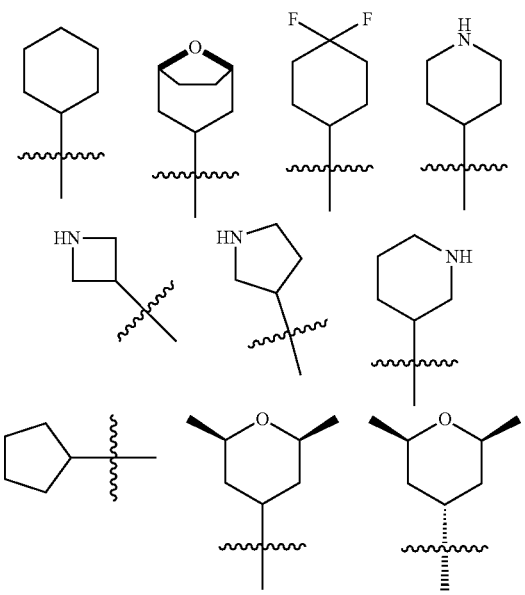

-continued

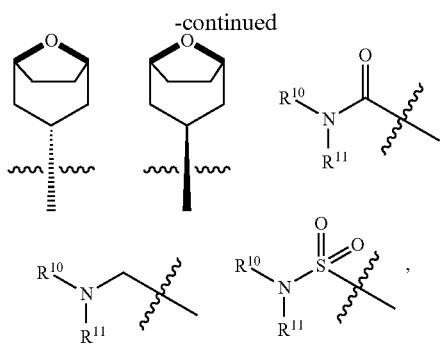

wherein $R^{10}$ and $R^{11}$ are defined herein;
4) $R^{5A}$ is selected from

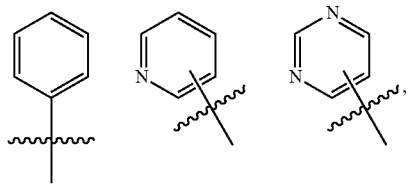

each of which is substituted with

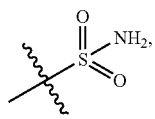

and further optionally substituted,
5) $R^{5A}$ is selected from

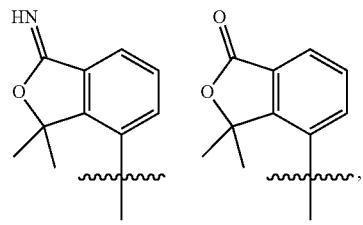

then $R^2$ in Formula II (including any of the applicable subformulae) can also be any of those described herein for $R^2$ in the context of Formula I, except that $R^{2A}$ is preferably not a halogen, —CN, —$NR^{10}R^{11}$ or —O—$R^{20}$.

For example, in some embodiments, $R^{3A}$ is an optionally substituted phenyl, an optionally substituted 4-pyridyl, optionally substituted 3-pyridyl, substituted 2-pyridyl, optionally substituted pyrimidinyl, or optionally substituted 5-membered heteroaryl, including any of those exemplified herein, $R^{2A}$ can be selected from an optionally substituted $C_{1-4}$ alkyl, an optionally substituted $C_{3-6}$ cycloalkyl, an optionally substituted 4-8 membered heterocyclyl, an optionally substituted phenyl, and an optionally substituted 5 or 6 membered heteroaryl. In some embodiments, the optionally substituted $C_{1-4}$alkyl, $C_{3-6}$ cycloalkyl, or 4-8 membered heterocyclyl is optionally substituted with 1-3 substituents independently selected from F, $C_{1-6}$ alkyl, and $C_{1-4}$ alkoxy; and the optionally substituted phenyl, or 5 or 6 membered heteroaryl is optionally substituted with 1-3 substituents independently selected from halogen (e.g., F), —CN, $C_{1-4}$ alkyl, fluorine substituted $C_{1-4}$ alkyl, $C_{1-4}$ alkoxy, and fluorine substituted $C_{1-4}$ alkoxy. In some embodiments, $R^2$ can be methyl, ethyl, isopropyl, —$CHF_2$, —$CF_3$, cyclopropyl, cyclobutyl, cyclopentyl, —$CH_2$—$CHF_2$ or —$CH_2$—$CF_3$. In such embodiments, $R^{5A}$ can be any of those described herein and $R^{1A}$ is typically hydrogen.

Similarly, when $R^{3A}$ is selected from:

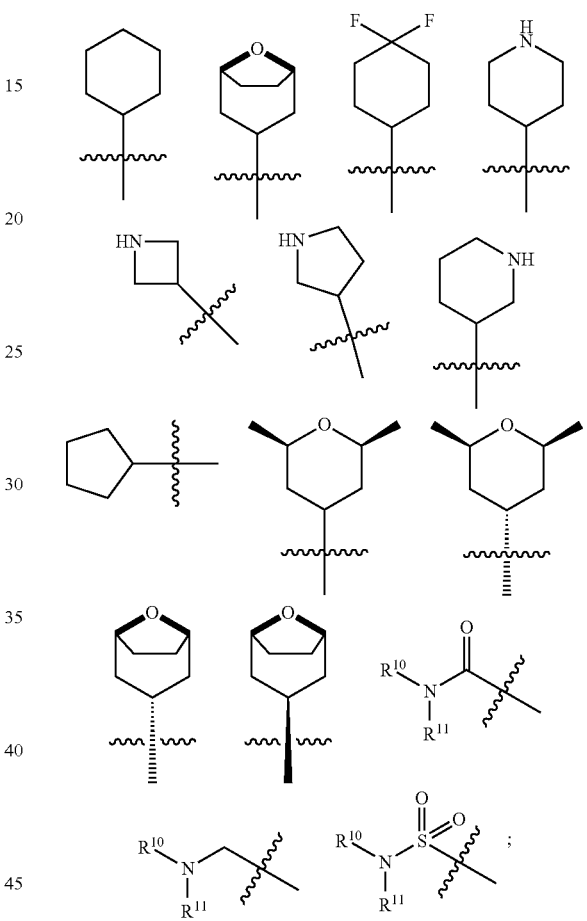

wherein $R^{10}$ and $R^{11}$ are defined herein,
$R^{2A}$ can be selected from an optionally substituted $C_{1-4}$ alkyl, an optionally substituted $C_{3-6}$ cycloalkyl, an optionally substituted 4-8 membered heterocyclyl, an optionally substituted phenyl, and an optionally substituted 5 or 6 membered heteroaryl. In some embodiments, the optionally substituted $C_{1-4}$ alkyl, $C_{3-6}$ cycloalkyl, or 4-8 membered heterocyclyl is optionally substituted with 1-3 substituents independently selected from F, $C_{1-4}$ alkyl, and $C_{1-4}$ alkoxy; and the optionally substituted phenyl, or 5 or 6 membered heteroaryl is optionally substituted with 1-3 substituents independently selected from halogen (e.g., F), —CN, $C_{1-4}$ alkyl, fluorine substituted $C_{1-4}$ alkyl, $C_{1-4}$ alkoxy, and fluorine substituted $C_{1-4}$ alkoxy. In some embodiments, $R^{2A}$ can be methyl, ethyl, isopropyl, —$CHF_2$, —$CF_3$, cyclopropyl, cyclobutyl, cyclopentyl, —$CH_2$—$CHF_2$ or —$CH_2$—$CF_3$. In such embodiments, $R^{5A}$ can be any of those described herein and $R^{1A}$ is typically hydrogen.

Similarly, when $R^{5A}$ is:

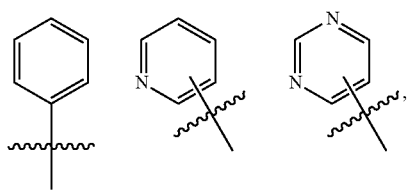

each of which is substituted with

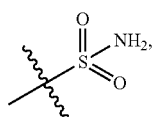

and further optionally substituted, or $R^{5A}$ is

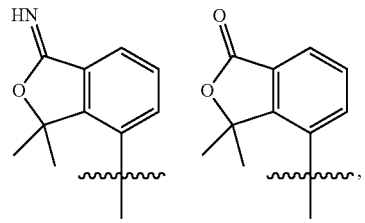

$R^{2A}$ can also be selected from an optionally substituted $C_{1-4}$ alkyl, an optionally substituted $C_{3-6}$ cycloalkyl, an optionally substituted 4-8 membered heterocyclyl, an optionally substituted phenyl, and an optionally substituted 5 or 6 membered heteroaryl. In some embodiments, the optionally substituted $C_{1-4}$ alkyl, $C_{3-6}$ cycloalkyl, or 4-8 membered heterocyclyl is optionally substituted with 1-3 substituents independently selected from F, $C_{1-4}$ alkyl, and $C_{1-4}$ alkoxy; and the optionally substituted phenyl, or 5 or 6 membered heteroaryl is optionally substituted with 1-3 substituents independently selected from halogen (e.g., F), —CN, $C_{1-4}$ alkyl, fluorine substituted $C_{1-4}$ alkyl, $C_{1-4}$ alkoxy, and fluorine substituted $C_{1-4}$ alkoxy. In some embodiments, $R^2$ can be methyl, ethyl, isopropyl, —CHF$_2$, —CF$_3$, cyclopropyl, cyclobutyl, cyclopentyl, —CH$_2$—CHF$_2$ or —CH$_2$—CF$_3$. In such embodiments, $R^{3A}$ can be any of those described herein and $R^{1A}$ is typically hydrogen.

Some embodiments of the present disclosure are directed to compounds of Formula II-S, or a pharmaceutically acceptable salt thereof:

Formula II-S

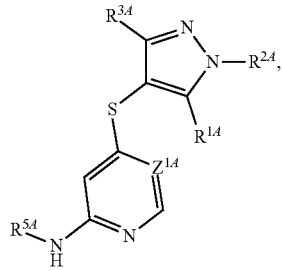

wherein the variables $R^{1A}$, $R^{2A}$, $R^{3A}$, $R^{5A}$ and $Z^{1A}$ can be any of those defined in the context of Formula II. For example, $R^{1A}$ is preferably hydrogen and $Z^{1A}$ is preferably hydrogen. In some embodiments, $R^2$ can be methyl, ethyl, isopropyl, —CHF$_2$, —CF$_3$, cyclopropyl, cyclobutyl, cyclopentyl, —CH$_2$—CHF$_2$ or —CH$_2$—CF$_3$. In some embodiments, $R^{3A}$ can be methyl, ethyl, isopropyl, tert-butyl, —CHF$_2$, —CF$_3$, —CH$_2$—CF$_3$,

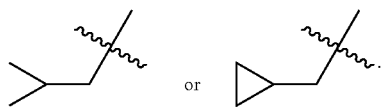

In some more specific embodiments, $R^{3A}$ can be selected from:

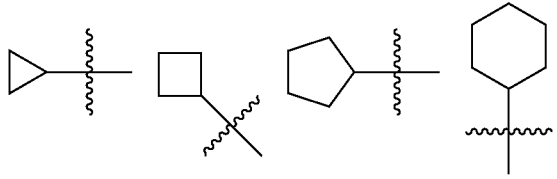

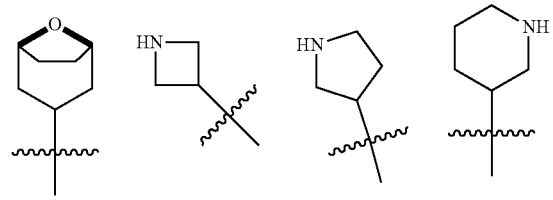

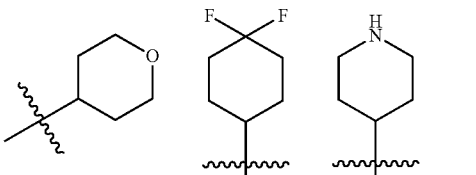

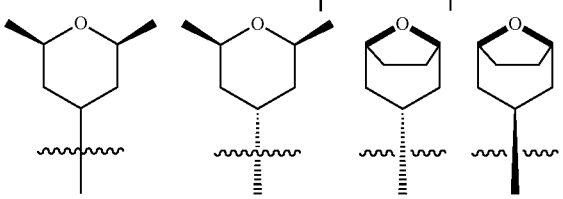

In some preferred embodiments, $R^{3A}$ can be

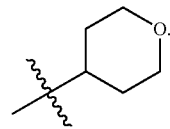

In some preferred embodiments, $R^{5A}$ can be selected from:

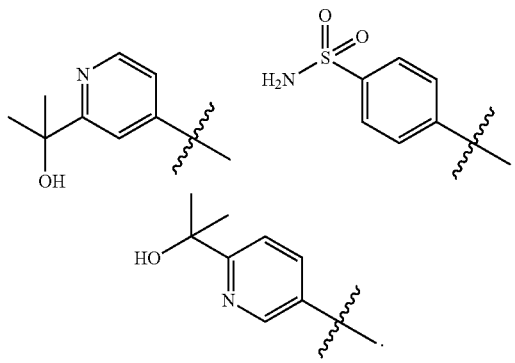

Formula III

Certain embodiments of the present disclosure are directed to compounds of Formula III, or a pharmaceutically acceptable salt thereof:

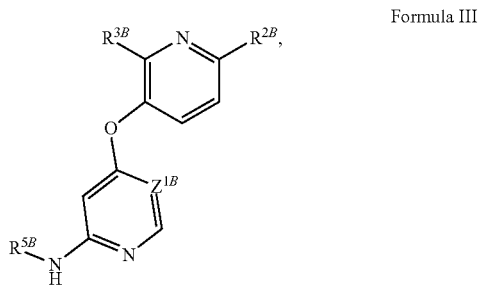

Formula III wherein
$R^{2B}$ and $R^{3B}$ are each independently hydrogen, halogen, —CN, —CO-$G^1$, —SO$_2$-$G^1$, —NR$^{10}$R$^{11}$, —O—R$^{20}$, an optionally substituted alkyl, an optionally substituted alkenyl, an optionally substituted alkynyl, an optionally substituted carbocyclic ring (e.g., C$_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl);
$Z^{1B}$ is N or CH; and
$R^{5B}$ is hydrogen, a nitrogen protecting group, an optionally substituted alkyl, an optionally substituted carbocyclic ring (e.g., C$_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl);
wherein $G^1$ at each occurrence is independently hydrogen, —NR$^{10}$R$^{11}$, —O—R$^{20}$, an optionally substituted alkyl, an optionally substituted alkenyl, an optionally substituted alkynyl, an optionally substituted carbocyclic ring (e.g., C$_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl);
wherein each of $R^{10}$ and $R^{11}$ at each occurrence is independently hydrogen, a nitrogen protecting group, an optionally substituted alkyl, an optionally substituted alkenyl, an optionally substituted alkynyl, an optionally substituted carbocyclic ring (e.g., C$_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl); or $R^{10}$ and $R^{11}$ together form an optionally substituted heterocyclic or heteroaryl ring, e.g., an optionally substituted 5-7 membered heterocyclic or an optionally substituted 5-10 membered heteroaryl; and wherein $R^{20}$ at each occurrence is independently hydrogen, am oxygen protecting group, an optionally substituted alkyl, an optionally substituted alkenyl, an optionally substituted alkynyl, an optionally substituted carbocyclic ring (e.g., C$_{3-6}$ carbocyclic ring), an optionally substituted heterocyclic ring (e.g., 5-8 membered heterocyclic ring), an optionally substituted aryl (e.g., phenyl), or an optionally substituted heteroaryl (e.g., 5-10 membered heteroaryl).

Typically, $Z^{1B}$ in Formula III is CH.

Various groups described herein are suitable for $R^{5B}$ in Formula III, which includes for example, any of those described as suitable as $R^5$ in the context of Formula I. For example, in some embodiments, $R^{5B}$ can be selected from:

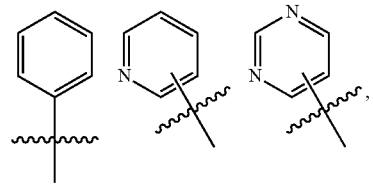

each of which is substituted with one substituent selected from,

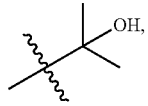 [SMILES: *C(C)(C)O]

—CONH$_2$, and

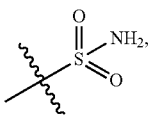 [SMILES: *S(N)(=O)=O]

and further optionally substituted, or $R^{5B}$ can be selected from:

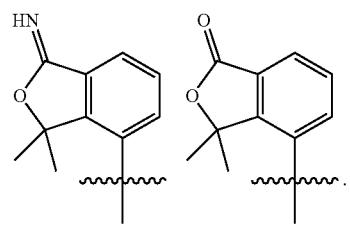

In some embodiments, the compound of Formula III can also be characterized as having Formula III-1, III-2, or III-3:

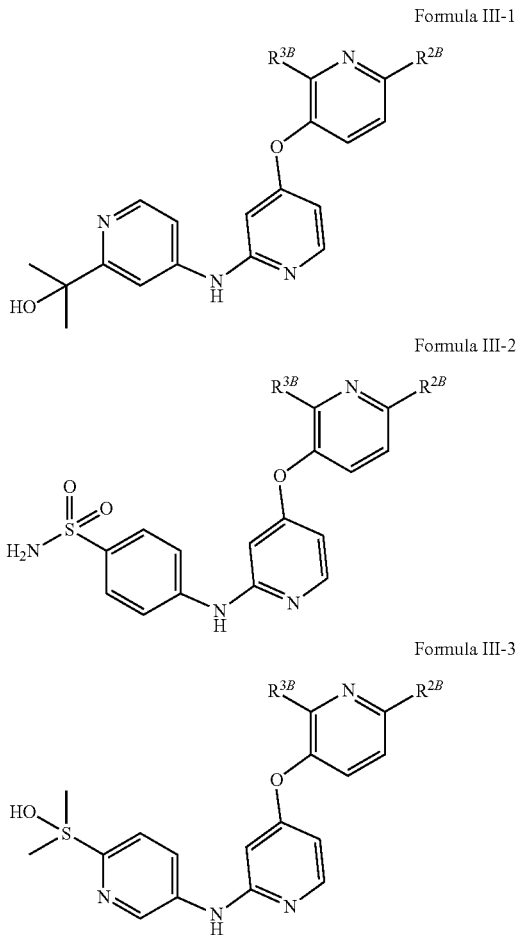

wherein $R^{2B}$ and $R^{3B}$ a defined herein.

Suitable $R^{2B}$ groups are described herein. In some embodiments, $R^{2B}$ in Formula III (including the subformulae III-1, III-2, and III-3) can also be any of those described herein for $R^2$ in the context of Formula I. For example, in some embodiments, $R^{2B}$ can be an optionally substituted $C_{1-4}$ alkyl, an optionally substituted $C_{3-4}$ cycloalkyl, an optionally substituted 4-8 membered heterocyclyl, an optionally substituted phenyl, and an optionally substituted 5 or 6 membered heteroaryl. In some embodiments, the optionally substituted $C_{1-6}$ alkyl, $C_{3-4}$ cycloalkyl, or 4-8 membered heterocyclyl is optionally substituted with 1-3 substituents independently selected from F, $C_{1-4}$ alkyl, and $C_{1-4}$ alkoxy; and the optionally substituted phenyl, or 5 or 6 membered heteroaryl is optionally substituted with 1-3 substituents independently selected from halogen (e.g., F), —CN, $C_{1-4}$ alkyl, fluorine substituted $C_{1-4}$ alkyl, $C_{1-4}$ alkoxy, and fluorine substituted $C_{1-4}$ alkoxy. In some embodiments, $R^{2B}$ is selected from a $C_{1-4}$ alkyl optionally substituted with 1-3 fluorine; a $C_{1-4}$ alkoxy optionally substituted with 1-3 fluorine; and a $C_{3-4}$ cycloalkyl optionally substituted with 1-3 substituents independently selected from fluorine and methyl. In some embodiments, $R^{2B}$ can be methyl, ethyl, isopropyl, methoxy, —CHF$_2$, —CF$_3$, cyclopropyl, cyclobutyl, cyclopentyl, —CH$_2$—CHF$_2$ or —CH$_2$—CF$_3$.

Suitable $R^{3B}$ groups are described herein. In some embodiments, $R^{3B}$ in Formula III (including the subformulae) can also be any of those described herein for $R^3$ in the context of Formula I. For example, in some embodiments, $R^{3B}$ in Formula III (including subformulae III-1, III-2, and III-3) can be selected from an optionally substituted $C_{1-4}$ alkyl, an optionally substituted $C_{3-6}$ cycloalkyl, an optionally substituted 4-8 membered heterocyclyl (e.g., described herein), an optionally substituted phenyl, and an optionally substituted 5 or 6 membered heteroaryl (e.g., described herein). In some embodiments, $R^{3B}$ is a $C_{1-4}$ alkyl optionally substituted with 1-3 fluorine; a $C_{3-6}$ cycloalkyl optionally substituted with 1-3 substituents independently selected from fluorine and $C_{1-4}$ alkyl (e.g., methyl); or a 4-8 membered heterocyclyl optionally substituted with 1-3 substituents independently selected from fluorine and $C_{1-4}$ alkyl (e.g., methyl). In some embodiments, $R^{3B}$ is a $C_{1-4}$ alkyl substituted with one $C_{3-4}$ cycloalkyl, i.e., —$C_{1-4}$ alkyl-($C_{3-4}$ cycloalkyl), which can be further optionally substituted. In some embodiments, $R^{3A}$ is a phenyl optionally substituted with 1-3 substituents independently selected from halogen (e.g., F), —CN, $C_{1-4}$ alkyl, fluorine substituted $C_{1-4}$ alkyl, $C_{1-4}$ alkoxy, and fluorine substituted $C_{1-4}$ alkoxy; or a 5 or 6 membered heteroaryl (e.g., described herein) optionally substituted with 1-3 substituents independently selected from halogen (e.g., F), —CN, $C_{1-4}$ alkyl, fluorine substituted $C_{1-4}$ alkyl, $C_{1-4}$ alkoxy, and fluorine substituted $C_{1-4}$ alkoxy.

In some preferred embodiments, $R^{3B}$ can be methyl, ethyl, isopropyl, tert-butyl, —CHF$_2$, —CF$_3$, —CH$_2$—CHF$_2$, —CH$_2$—CF$_3$,

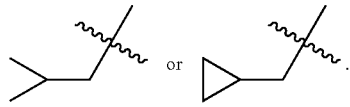

In some preferred embodiments, $R^{3B}$ can be selected from:

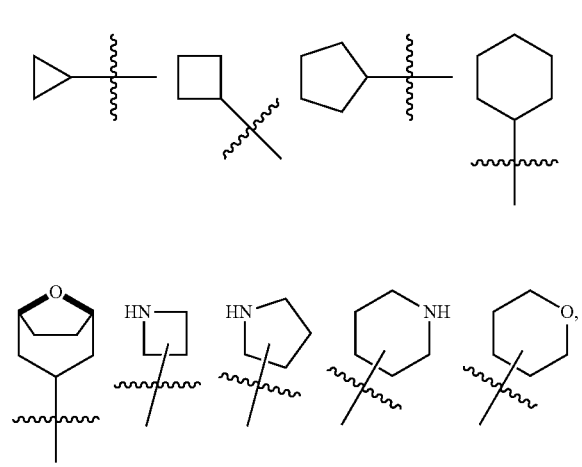

each of which is optionally substituted, for example, with 1 or 2 substituents independently selected from F and methyl.

In some more specific embodiments, $R^{3B}$ can be selected from:

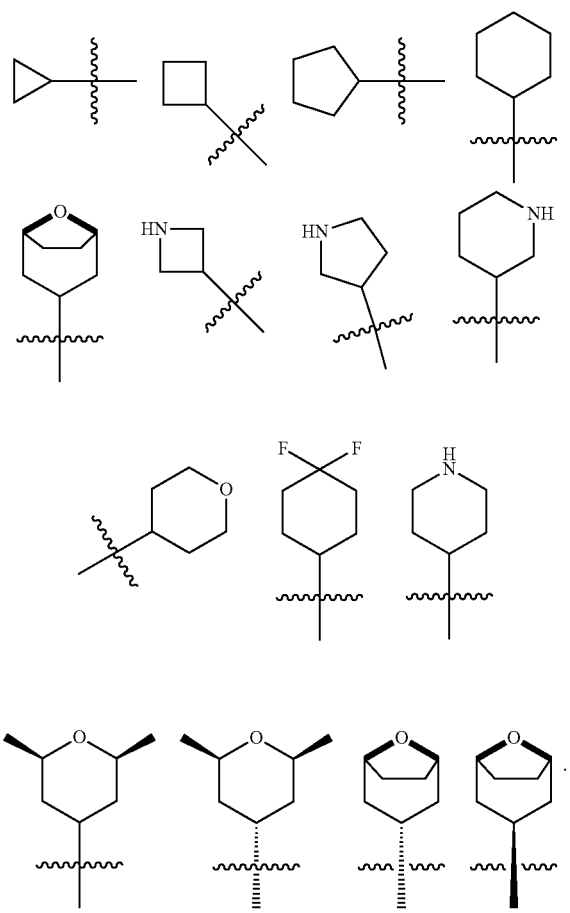

In some preferred embodiments, $R^{3B}$ can be

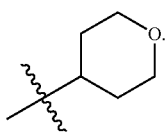

In some preferred embodiments, $R^{3B}$ can be selected from:

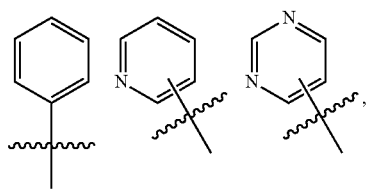

each of which is optionally substituted, for example, with 1 or 2 substituents independently selected from F, Cl, methyl, and CN.

In some more specific embodiments, $R^{3B}$ is an optionally substituted phenyl or heteroaryl selected from

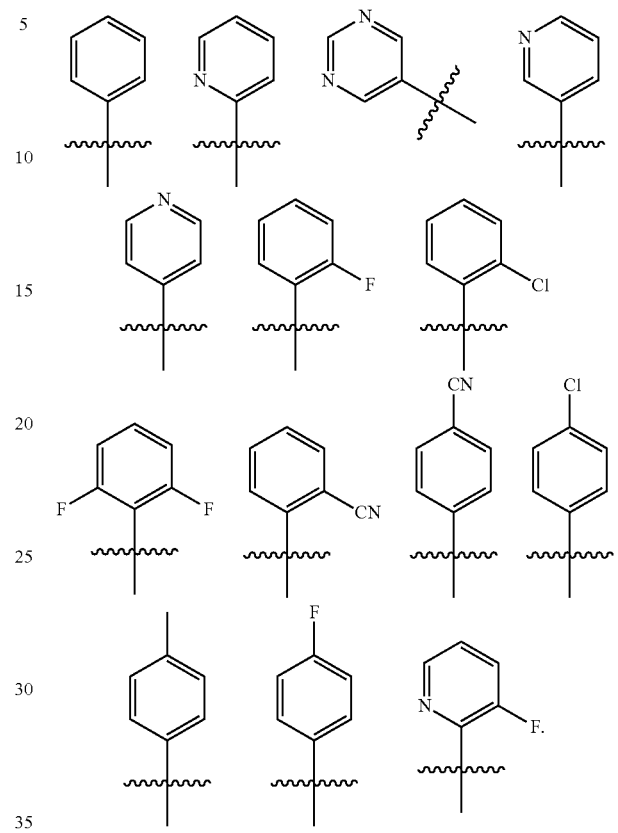

Some embodiments of the present disclosure are directed to compounds of Formula III-S, or a pharmaceutically acceptable salt thereof:

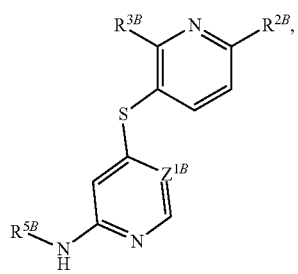

Formula III-S wherein the variables $R^{2B}$, $R^{3B}$, $R^{5B}$ and $Z^{1B}$ can be any of those defined in the context of Formula III. For example, $Z^{1B}$ is preferably hydrogen. In some embodiments, $R^{2B}$ can be methyl, ethyl, isopropyl, —CHF$_2$, —CF$_3$, cyclopropyl, cyclobutyl, cyclopentyl, —CH$_2$—CHF$_2$ or —CH$_2$—CF$_3$. In some embodiments, $R^{3B}$ can be methyl, ethyl, isopropyl, tert-butyl, —CHF$_2$, —CF$_3$, —CH$_2$—CF$_3$,

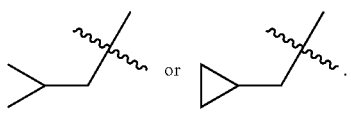

In some more specific embodiments, $R^{3B}$ can be selected from:

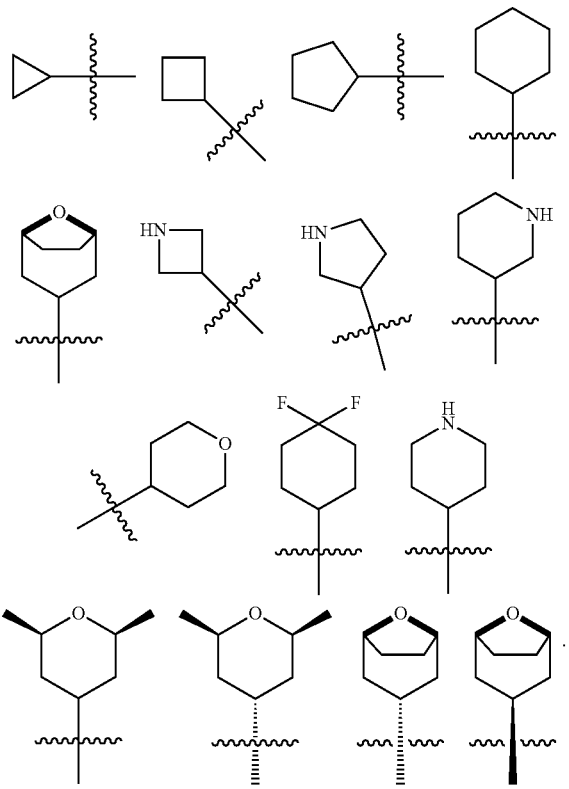

In some preferred embodiments, $R^{3B}$ can be

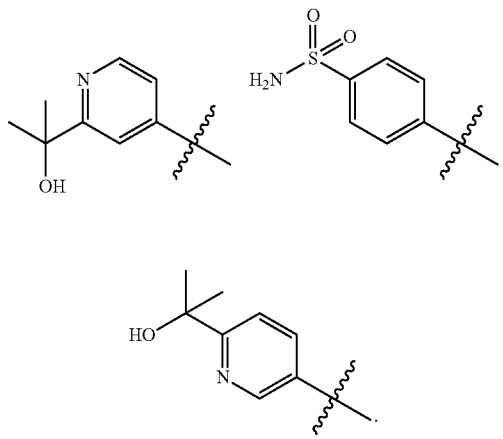

In some preferred embodiments, $R^{5B}$ can be selected from:

Formula IV

Certain embodiments of the present disclosure are directed to compounds of Formula IV, or a pharmaceutically acceptable salt thereof:

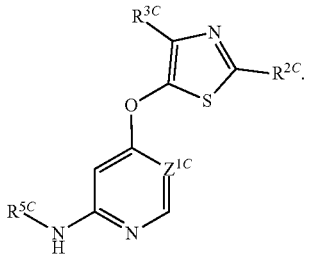

Formula IV

Typically, $Z^{1C}$ in Formula IV is CH. $R^{2C}$ in Formula IV can be any of those described herein for $R^2$ in the context of Formula I. For example, in some embodiments, $R^{2C}$ can be methyl, ethyl, isopropyl, methoxy, —$CHF_2$, —$CF_3$, cyclopropyl, cyclobutyl, cyclopentyl, —$CH_2$—$CHF_2$ or —$CH_2$—$CF_3$. $R^{3C}$ in Formula IV can be any of those described herein for $R^3$ in the context of Formula I. For example, in some embodiments, $R^{3C}$ can be methyl, ethyl, isopropyl, tert-butyl, —$CHF_2$, —$CF_3$, —$CH_2$—$CHF_2$, —$CH_2$—$CF_3$,

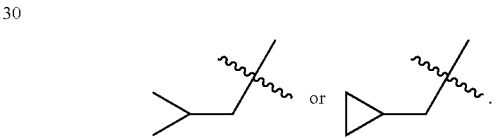

In some preferred embodiments, $R^{3C}$ can be selected from:

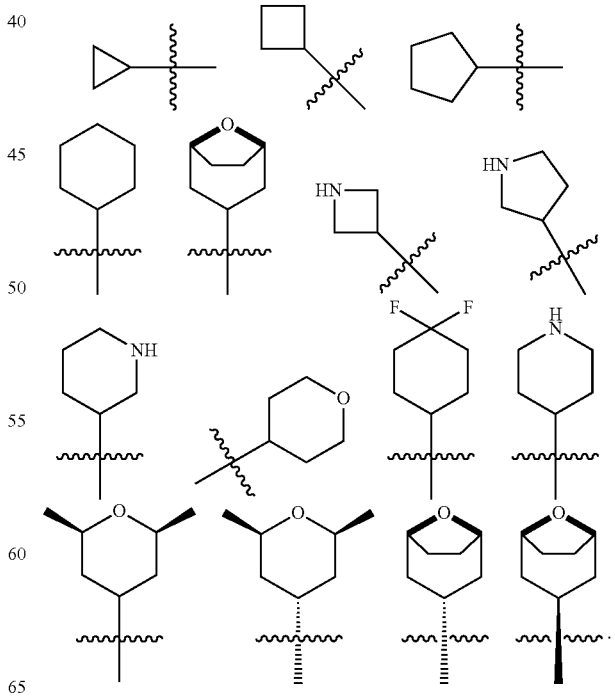

In some preferred embodiments, R³ can be
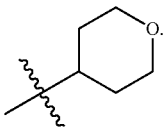
R⁵ᶜ in Formula IV can also be any of those described herein for R⁵ in the context of Formula I. For example, in some embodiments, R⁵ᶜ can be selected from:
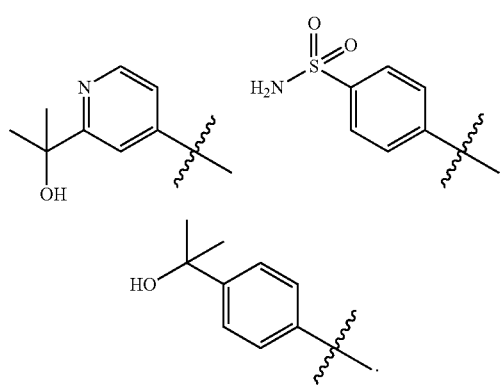
In some specific embodiments, the present invention provides a compound selected from Compound Nos. 1-90, or a pharmaceutically acceptable salt thereof:
1
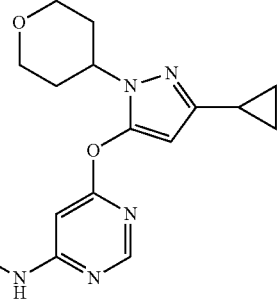
2
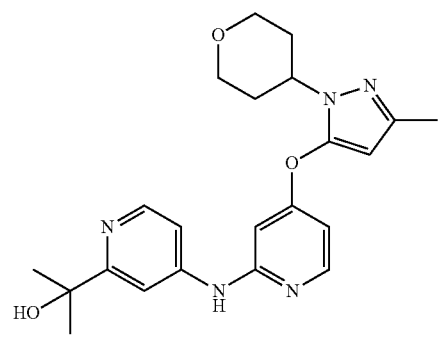
-continued
3
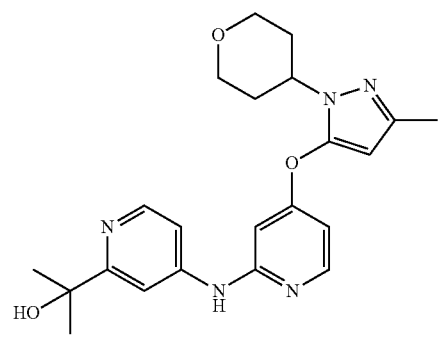
4
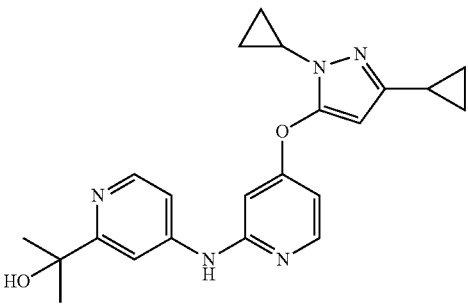
5
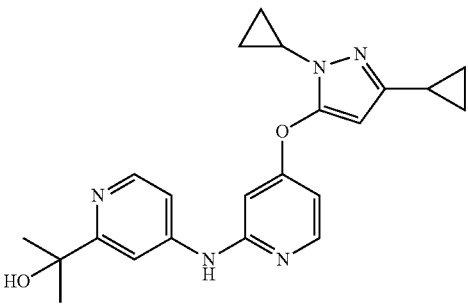
6
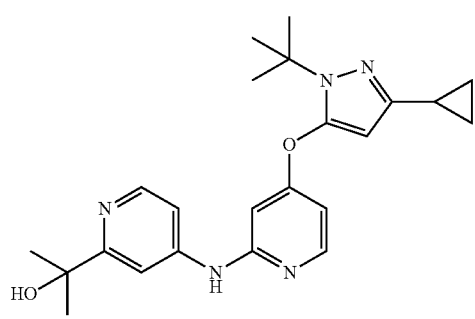
7
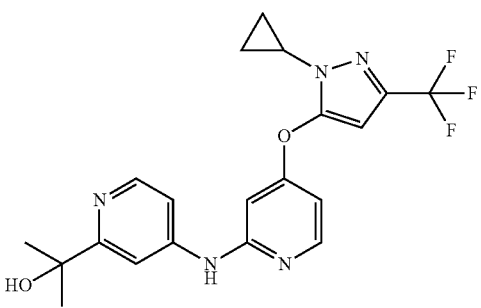

8
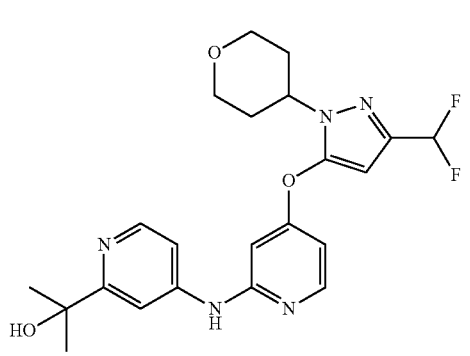
13
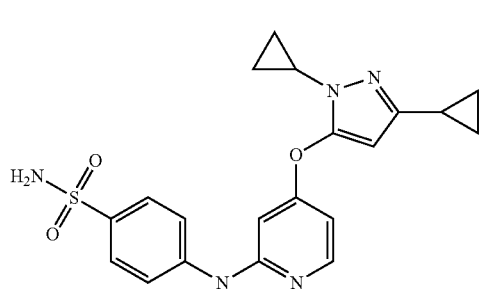
9
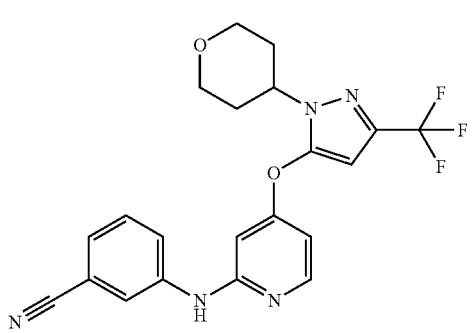
14
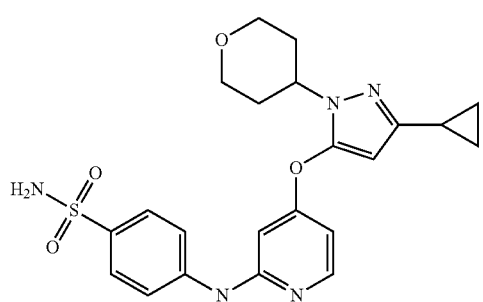
10
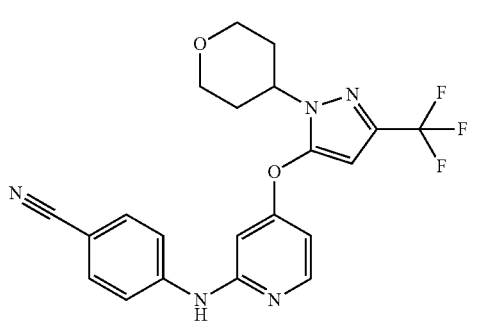
15
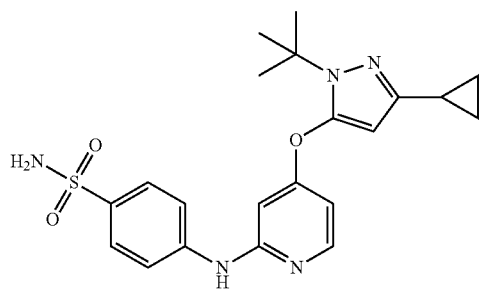
11
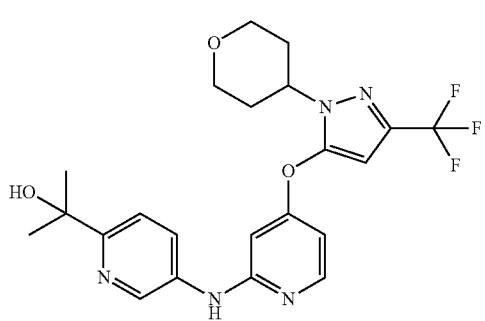
16
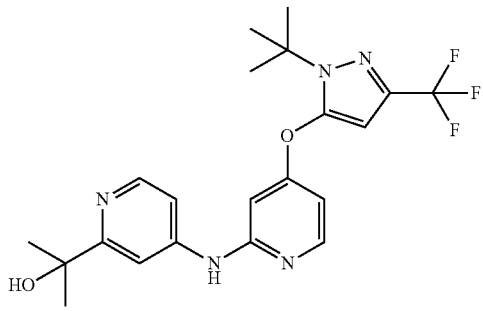
12
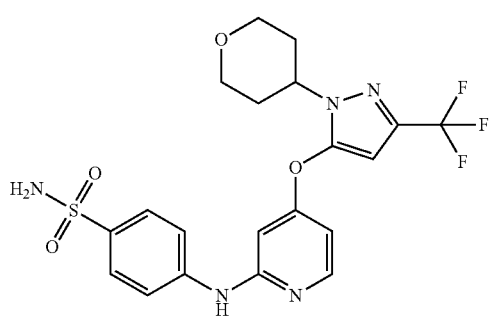
17
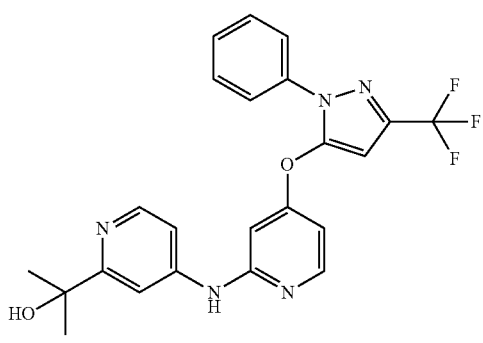

18
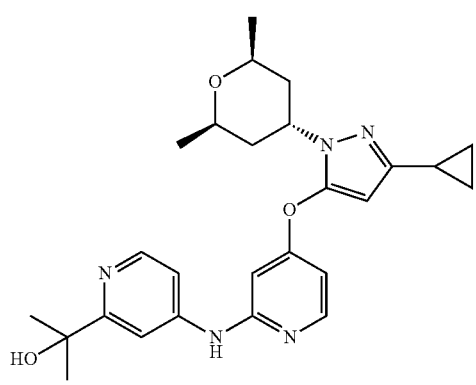
relative configuration
19
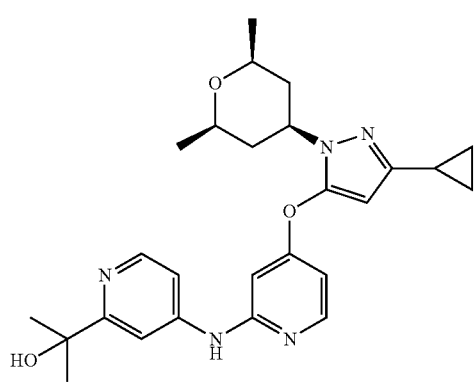
relative configuration
20
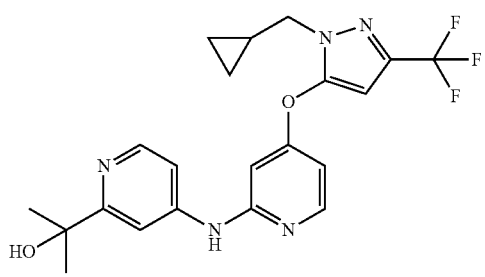
21
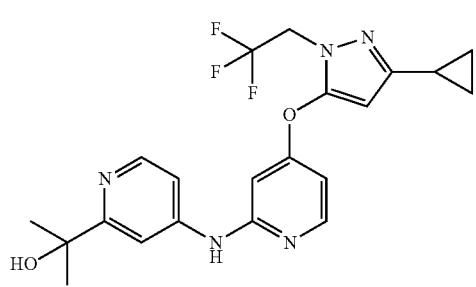
22
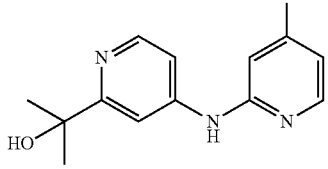
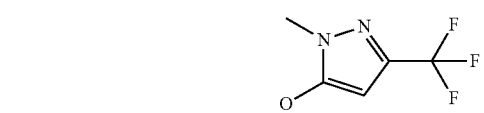
23
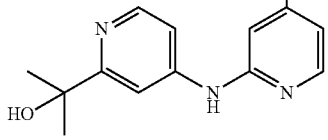
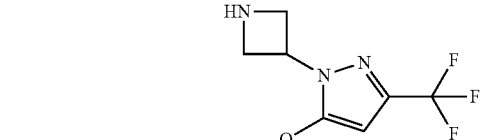
24
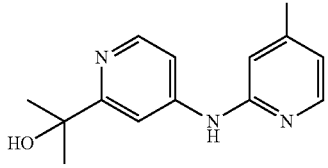
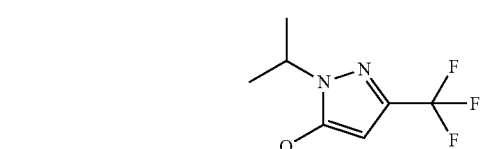
25
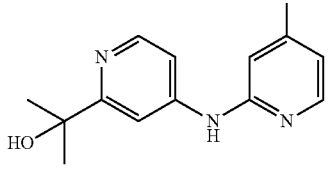
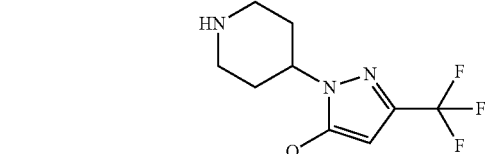
26
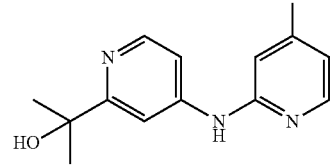

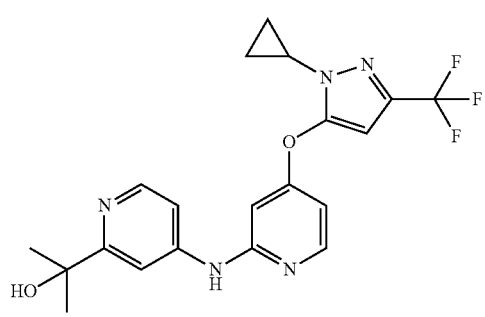
27
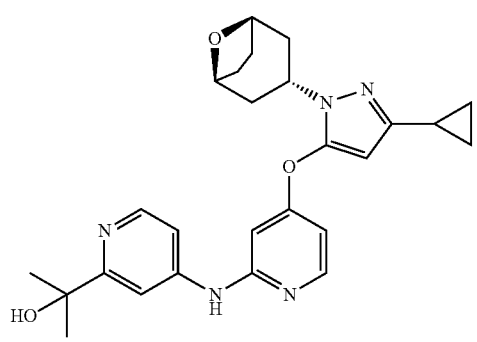
28
relative configuration
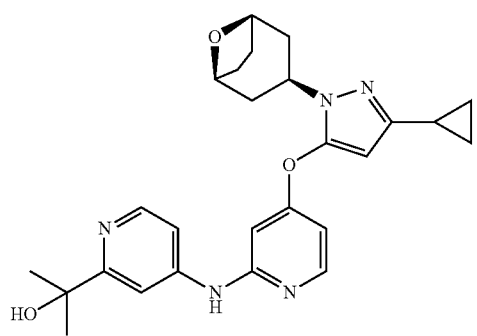
29
relative configuration
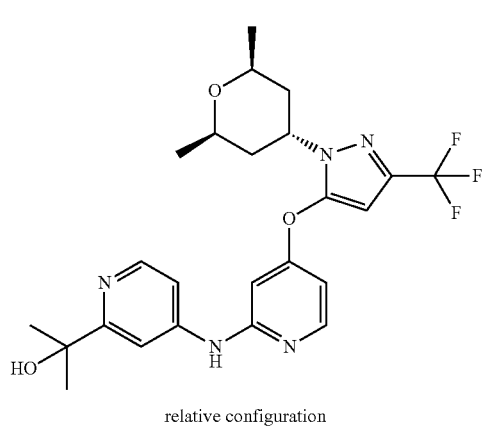
30
relative configuration
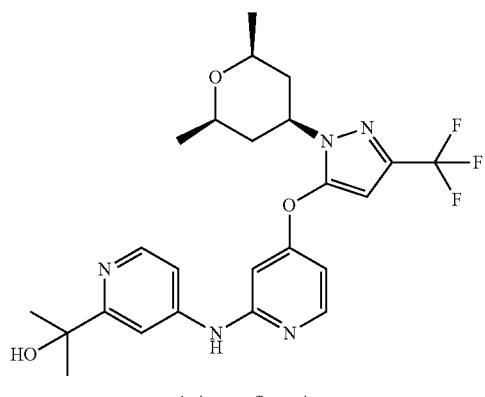
31
relative configuration
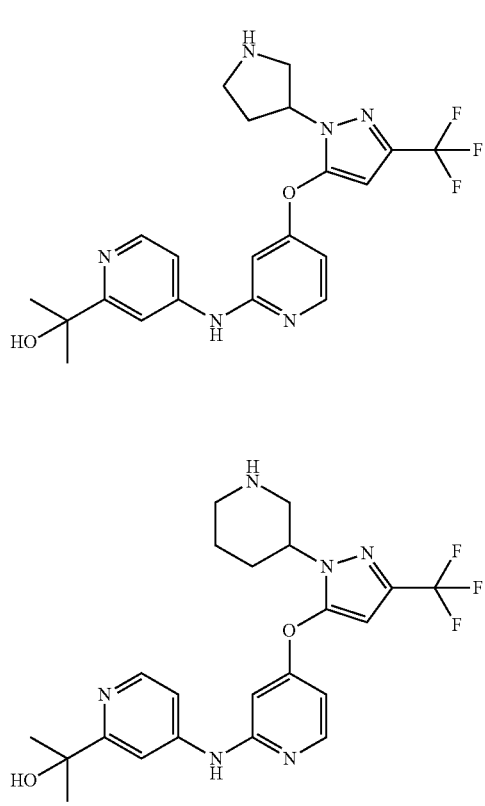
32
33
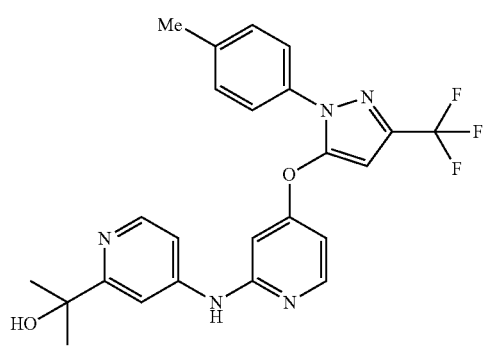
34

35
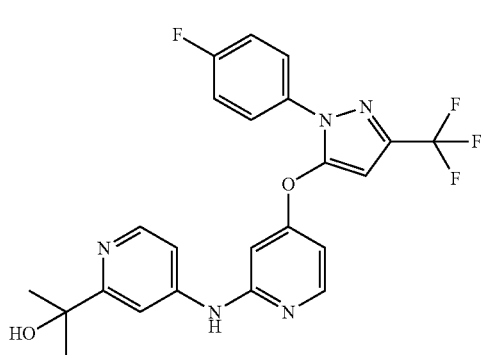
36
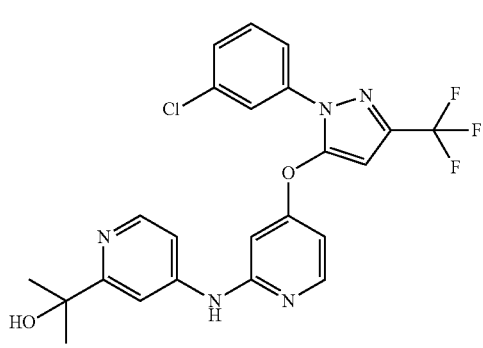
37
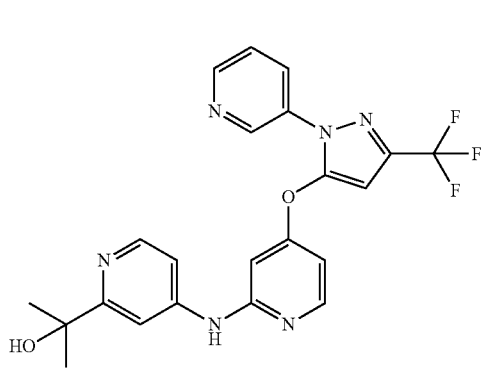
38
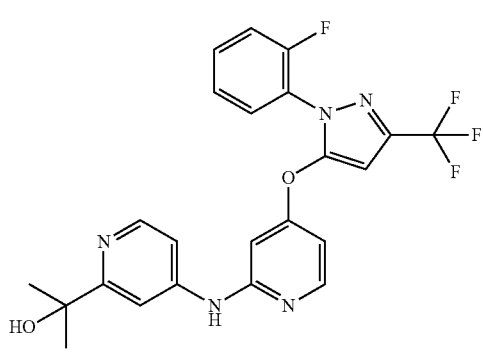
39
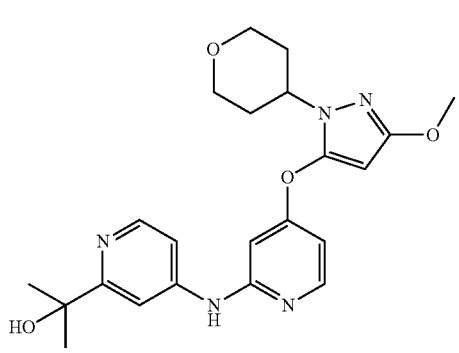
40
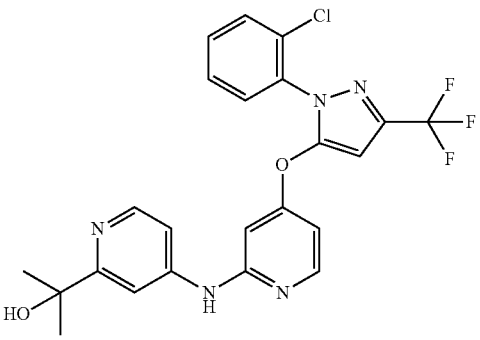
41
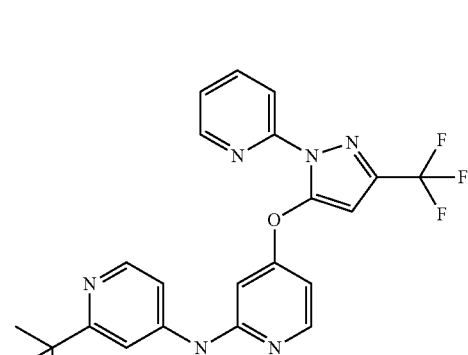
42
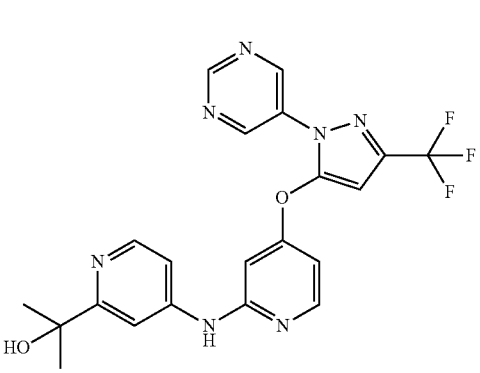

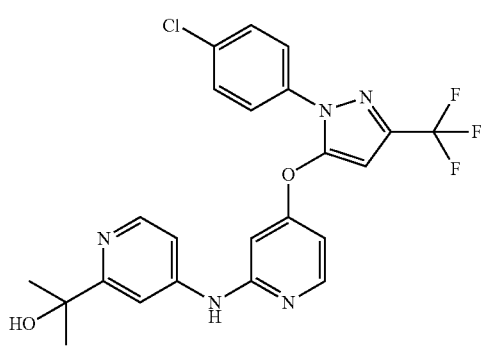
43
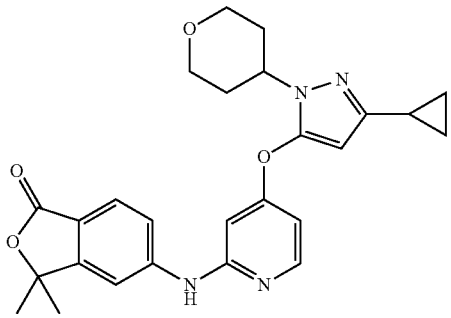
47
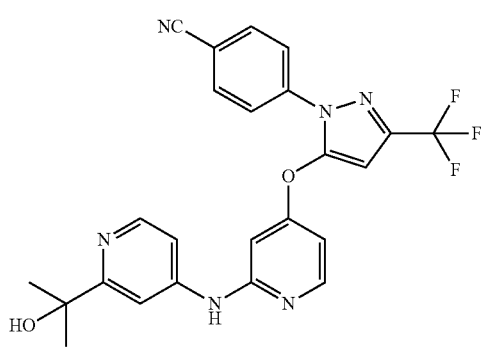
44
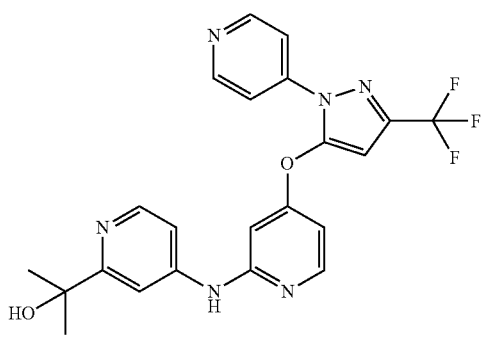
48
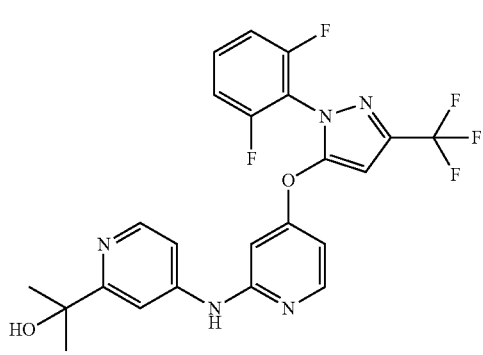
45
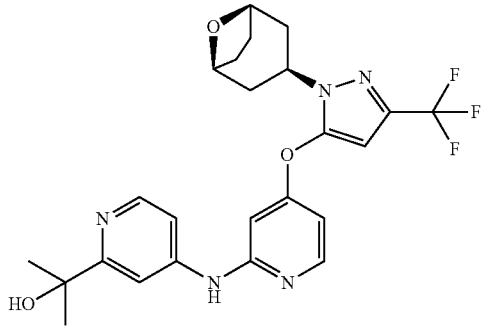
49
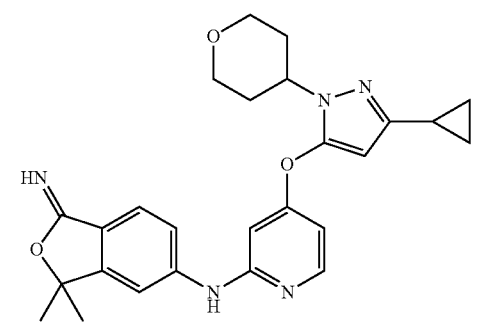
46
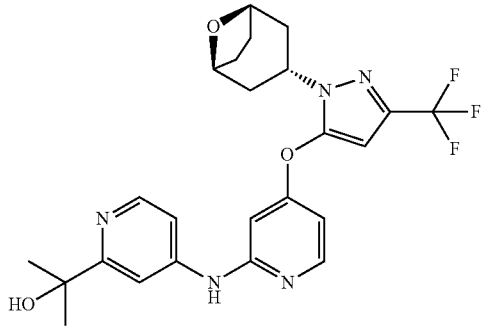
50

-continued
51
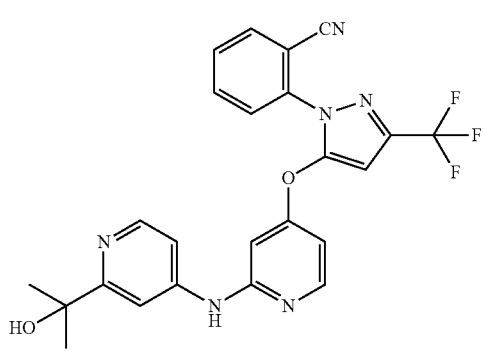
52
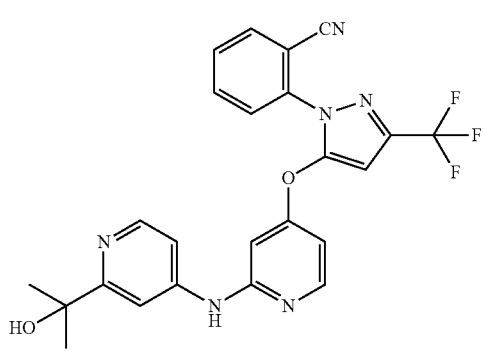
53
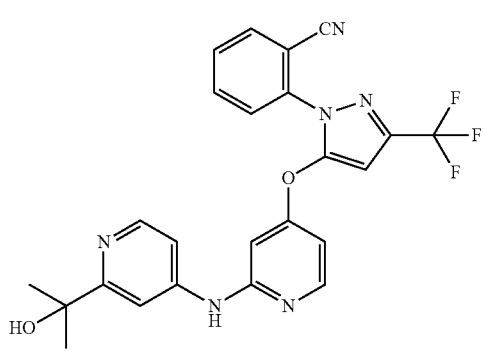
54
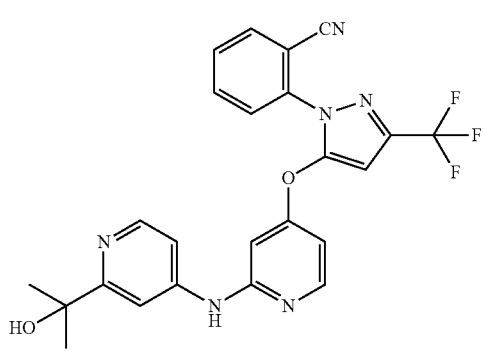
55
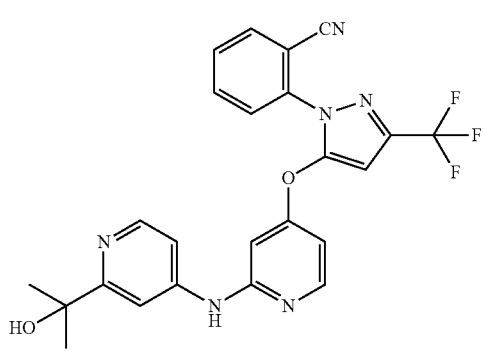
-continued
56
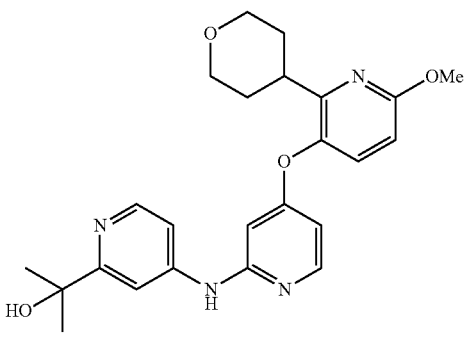
57
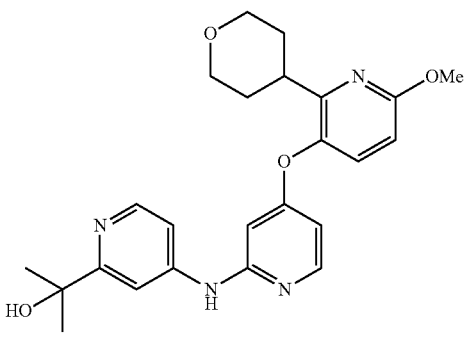
58
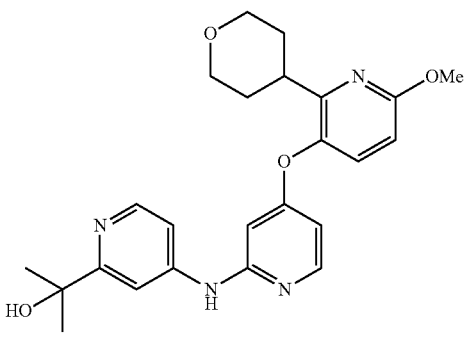
59
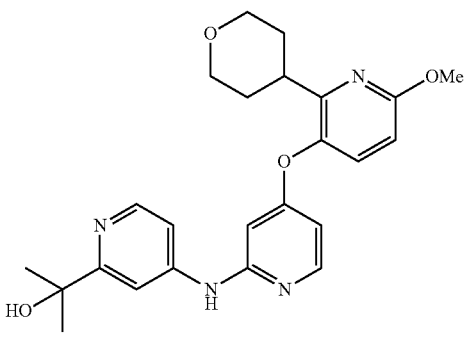
60
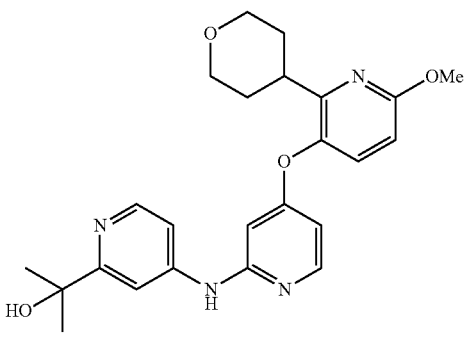

-continued
61
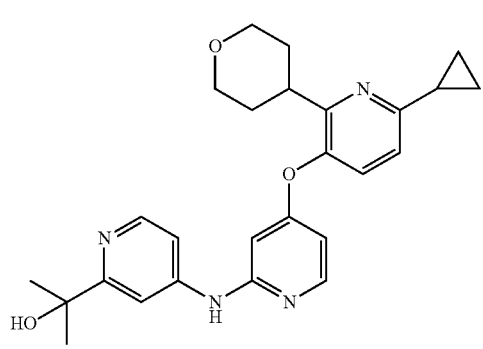
62
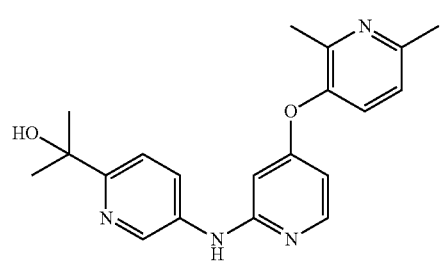
63
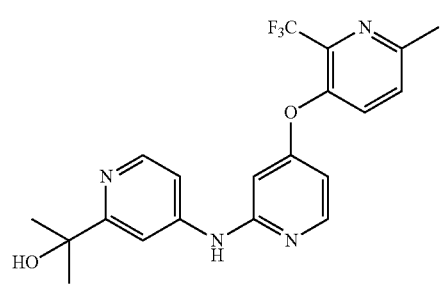
64
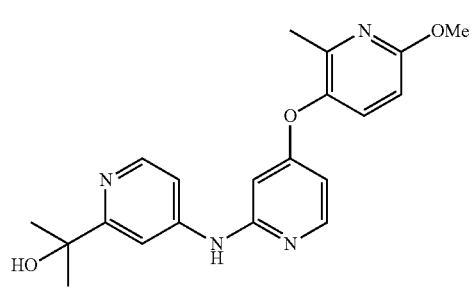
65
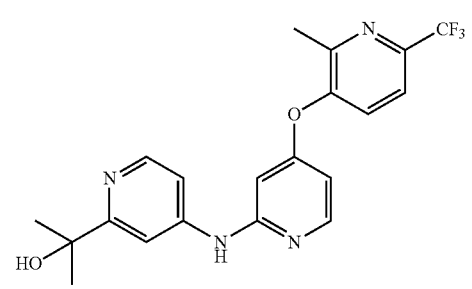
66
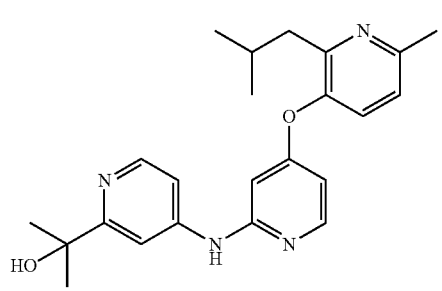
67
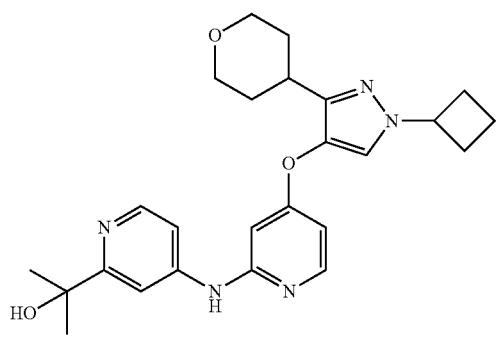
68
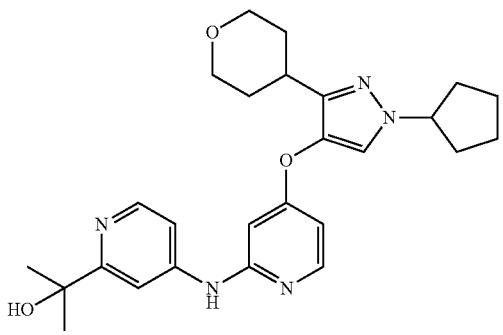
69
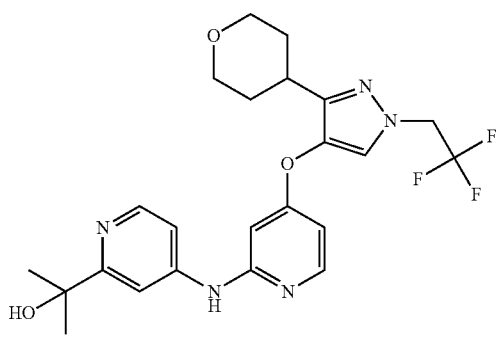
70
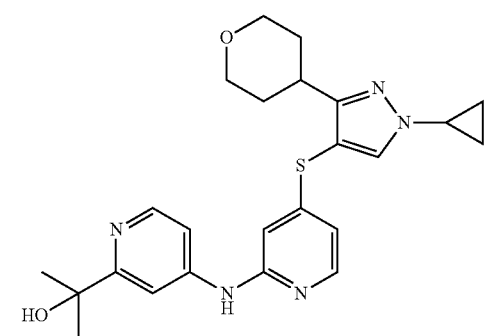

| 49 | 50 |
|---|---|
| -continued | -continued |
| 71 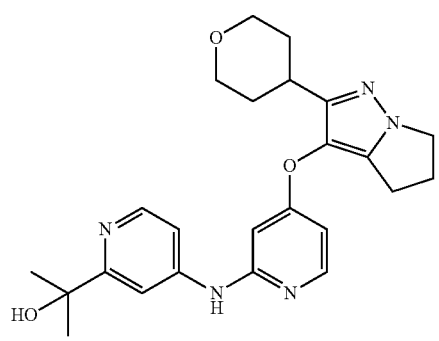 | 75 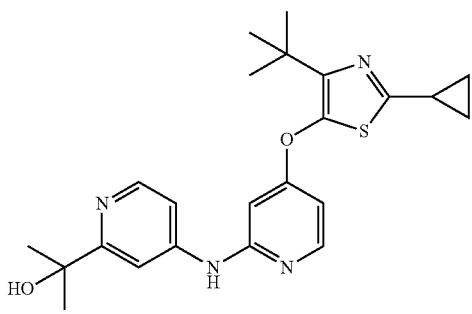 |
| 72 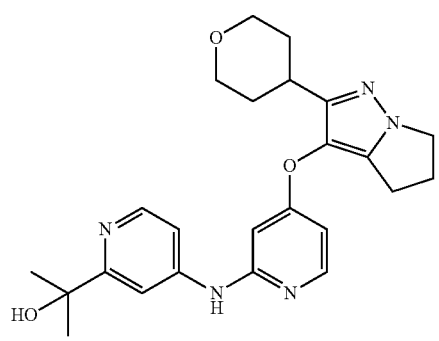 | 76 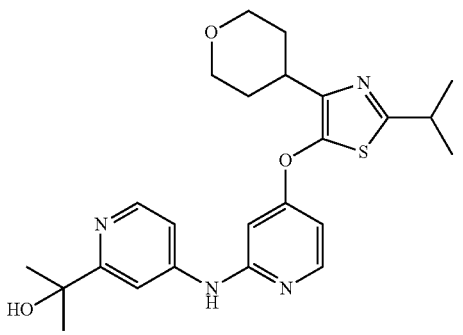 |
| 73 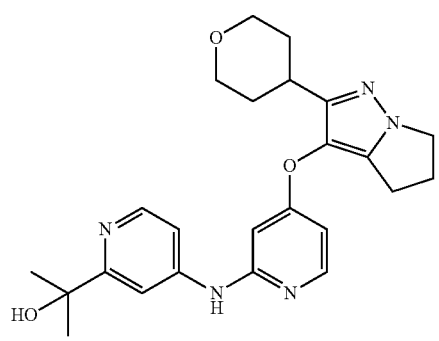 | 77 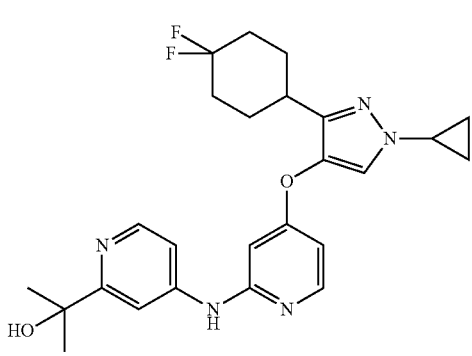 |
| 74 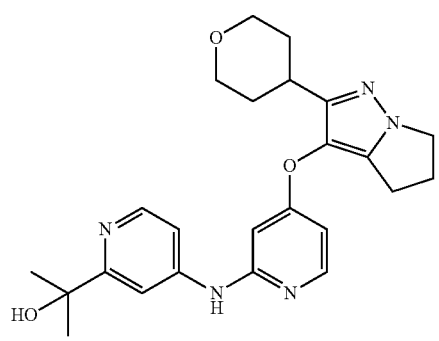 | 78 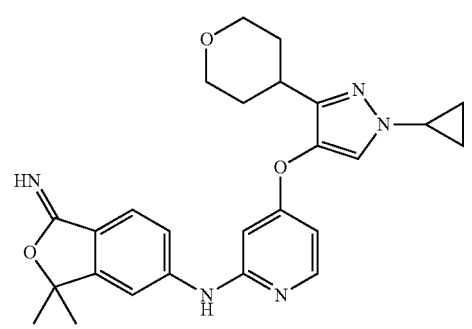 |
|  | 79 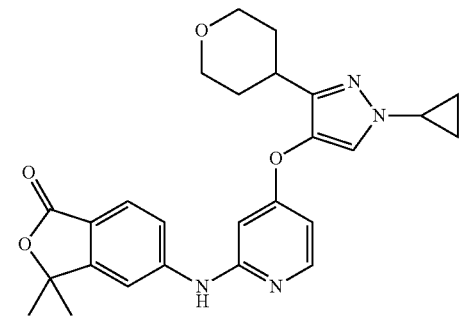 |

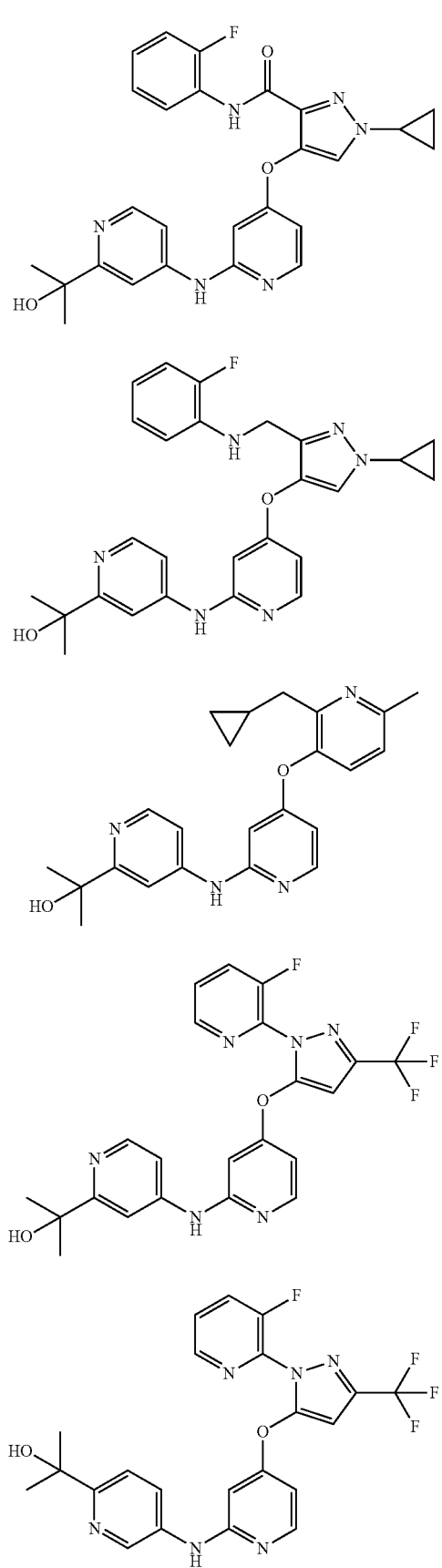
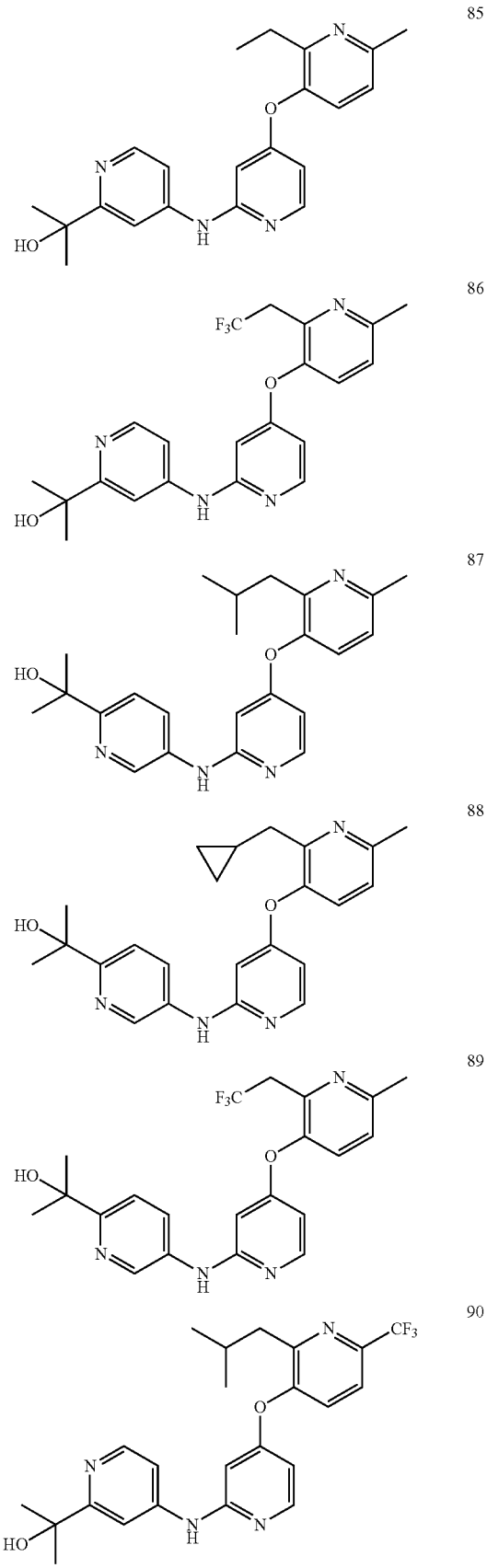

Method of Synthesis

The compounds of the present disclosure can be readily synthesized by those skilled in the art in view of the present disclosure. Exemplified synthesis are also shown in the Examples section. Some embodiments of the present disclosure are also directed to such synthetic methods and synthetic intermediates.

The synthesis of compounds of Formula I-1 as shown in Scheme 1 is a representative method for the preparation of compounds herein. Although the core structures of Formula II, III, or IV are different, similar methods and sequences can also be applied for the synthesis of those compounds.

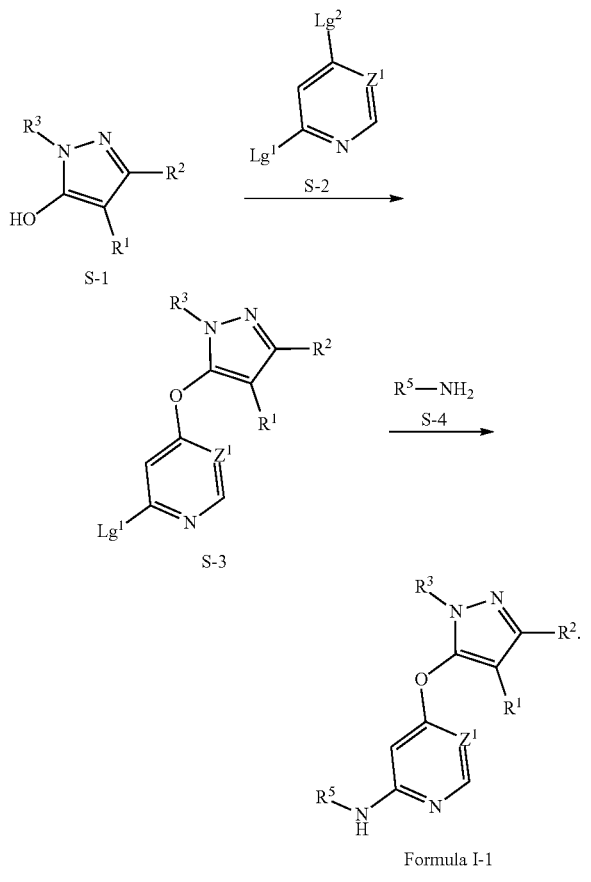

Scheme 1

Thus, a pyrrazole starting material of S-1 can react with a pyridinyl or pyrimidinyl compound of S-2 to form a compound of S-3, which can react with an amine S-4 to form the compound of Formula I-1. Typically, the $Lg^1$ and $Lg^2$ in S-2 are different leaving groups, with $Lg^2$ having a better reactivity towards S-1. For example, in some embodiments, $Lg^1$ can be Cl, and $Lg^2$ can be F. The reaction of amine S-4 with the compound of S-3 can proceed under any suitable cross-coupling reaction conditions, for example, such transformation can be carried out under the catalysis of palladium or copper. The variables $R^1$, $R^2$, $R^3$, $Z^1$, and $R^5$ in Scheme 1 are defined herein.

In some embodiments, the introduction of $R^3$ groups on Formula I-1 can be carried out at a later stage. For example, as shown in Scheme 2, a protected pyrrazole starting material of S-5 can react with a pyridinyl or pyrimidinyl compound of S-2 to form a compound of S-6, which can react with an amine S-4 to form the compound of S-7, which is analogous to the method described above for Scheme 1. The protecting group $Pg^1$ can be any of those suitable nitrogen protecting groups for protecting a pyrazole, such as a tert-butyl group. After which, a deprotection step can convert compound S-7 into compound S-8, which can react with a suitable $R^3$ donor, such as a compound of S-9, wherein $Lg^3$ is a leaving group, to provide the compound of Formula I-1. Other $R^3$ donors can also be used. For example, in some embodiments, $R^3$ donors can be a boronic acid or ester derivative that can react with compound S-8 under copper catalyzed amination reaction conditions. See Example 8. $Lg^3$ in S-9 can be any of those suitable leaving groups, such as a mesylate. The variables $R^1$, $R^2$, $R^3$, $Z^1$, and $R^5$ in Scheme 2 are defined herein.

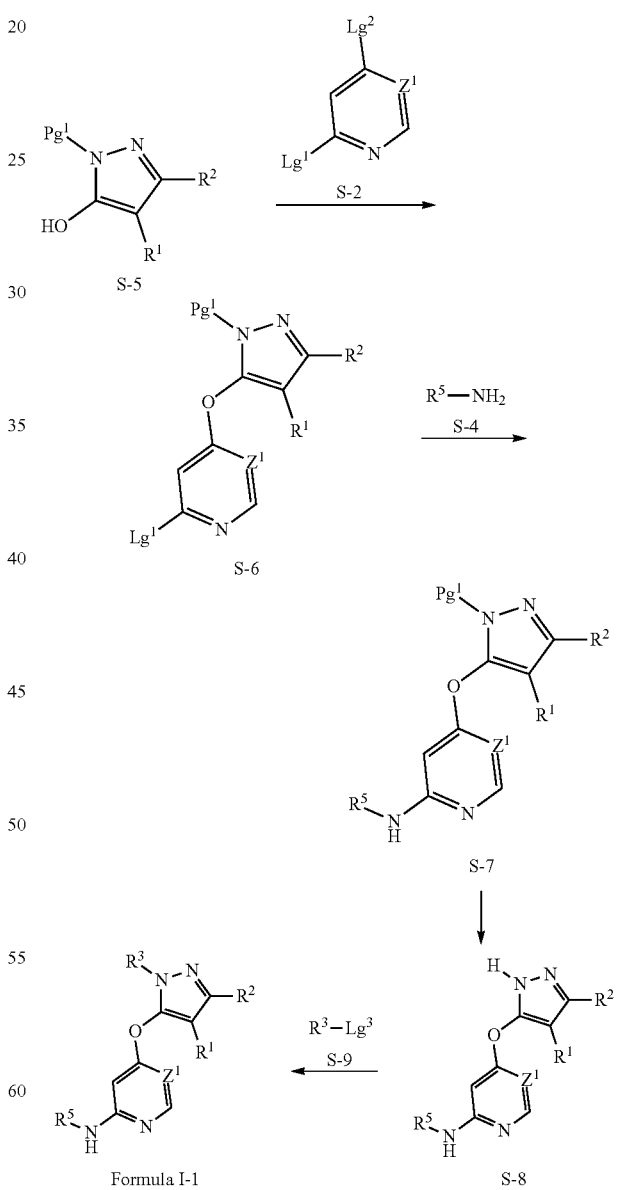

Scheme 2

The pyrrazole compounds such as S-1 or S-5 used for the synthetic processes herein can generally be prepared through a pyrrazole synthesis, such as similar procedures described in Examples. Those skilled in the art would also understand that in some cases, functional group transformations of one compound of the present disclosure, e.g., having a Formula I-1, can lead to another compound of the present disclosure, e.g., having a Formula I-1. For example, as shown in Example 9, a palladium catalyzed cyanation reaction can convert a compound with chlorophenyl as $R^3$ into a compound with cyanophenyl as $R^3$. Other types of cross-coupling can also be used which can lead to various compounds of the present disclosure. Further, those skilled in the art would also know that the synthetic sequences described herein that involve a cross coupling reaction can be modified to use an alternative cross coupling reaction, for example, by switching the roles of the cross coupling partners.

Compounds of Formulae II, II-S, III, III-S, and IV can be prepared similarly. WO 2016/057278 and WO2009/022171 describe synthetic processes that can be adapted for the synthesis herein.

As will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in "Protective Groups in Organic Synthesis", $4^{th}$ ed. P. G. M. Wuts; T. W. Greene, John Wiley, 2007, and references cited therein. The reagents for the reactions described herein are generally known compounds or can be prepared by known procedures or obvious modifications thereof. For example, many of the reagents are available from commercial suppliers such as Aldrich Chemical Co. (Milwaukee, Wis., USA), Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplemental (Elsevier Science Publishers, 1989), Organic Reactions, Volumes 1-40 (John Wiley and Sons, 1991), March's Advanced Organic Chemistry, (Wiley, $7^{th}$ Edition), and Larock's Comprehensive Organic Transformations (Wiley-VCH, 1999), and any of available updates as of this filing.

Pharmaceutical Compositions

Certain embodiments are directed to a pharmaceutical composition comprising one or more of the compounds of the present disclosure.

The pharmaceutical composition can optionally contain a pharmaceutically acceptable excipient. In some embodiments, the pharmaceutical composition comprises a compound of the present disclosure (e.g., a compound of Formula I (e.g., Formula I-1, I-2, I-3, I-4, or I-5), Formula II (e.g., Formula II-1, II-2, II-3, II-4, II-5, II-6, or II-7), Formula II-S, Formula III (e.g., Formula III-1, III-2, or III-3), Formula III-S, Formula IV, or any of Compound Nos. 1-90, or a pharmaceutically acceptable salt thereof) and a pharmaceutically acceptable excipient. Pharmaceutically acceptable excipients are known in the art. Non-limiting suitable excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. See also Remington's The Science and Practice of Pharmacy, 21st Edition, A. R. Gennaro (Lippincott, Williams & Wilkins, Baltimore, Md., 2005; incorporated herein by reference), which discloses various excipients used in formulating pharmaceutical compositions and known techniques for the preparation thereof.

The pharmaceutical composition can include any one or more of the compounds of the present disclosure. For example, in some embodiments, the pharmaceutical composition comprises a compound of any of Formula I (e.g., Formula I-1, I-2, I-3, I-4, or I-5), Formula II (e.g., Formula II-1, II-2, II-3, II-4, II-5, II-6, or II-7), Formula II-S, Formula III (e.g., Formula III-1, III-2, or III-3), Formula III-S, Formula IV, or any of Compound Nos. 1-90, or a pharmaceutically acceptable salt thereof, e.g., in a therapeutically effective amount. In any of the embodiments described herein, the pharmaceutical composition can comprise a therapeutically effective amount of a compound selected from Compound Nos. 1-90, or a pharmaceutically acceptable salt thereof.

The pharmaceutical composition can also be formulated for delivery via any of the known routes of delivery, which include but are not limited to oral, parenteral, inhalation, etc.

In some embodiments, the pharmaceutical composition can be formulated for oral administration. The oral formulations can be presented in discrete units, such as capsules, pills, cachets, lozenges, or tablets, each containing a predetermined amount of the active compound; as a powder or granules; as a solution or a suspension in an aqueous or non-aqueous liquid; or as an oil-in-water or water-in-oil emulsion. Excipients for the preparation of compositions for oral administration are known in the art. Non-limiting suitable excipients include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof.

In some embodiments, the pharmaceutical composition is formulated for parenteral administration (such as intravenous injection or infusion, subcutaneous or intramuscular injection). The parenteral formulations can be, for example, an aqueous solution, a suspension, or an emulsion. Excipients for the preparation of parenteral formulations are known in the art. Non-limiting suitable excipients include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof.

In some embodiments, the pharmaceutical composition is formulated for inhalation. The inhalable formulations can be, for example, formulated as a nasal spray, dry powder, or an aerosol administrable through a metered-dose inhaler. Excipients for preparing formulations for inhalation are known in the art. Non-limiting suitable excipients include, for example, lactose, talc, silicic acid, aluminum hydroxide, calcium silicates and polyamide powder, and mixtures of these substances. Sprays can additionally contain propellants, such as chlorofluorohydrocarbons and volatile unsubstituted hydrocarbons, such as butane and propane.

The pharmaceutical composition can include various amounts of the compounds of the present disclosure, depending on various factors such as the intended use and potency and selectivity of the compounds. In some embodiments, the pharmaceutical composition comprises a therapeutically effective amount of a compound of the present disclosure. In some embodiments, the pharmaceutical composition comprises a therapeutically effective amount of the compound of the present disclosure and a pharmaceutically acceptable excipient. As used herein, a therapeutically effective amount of a compound of the present disclosure is an amount effective to treat a disease or disorder as described herein, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

Method of Treatment

Compounds of the present disclosure have various utilities. For example, compounds of the present disclosure can be used as therapeutic active substances for the treatment and/or prophylaxis of diseases or disorders that are modulated by TGF-beta signaling. It's been shown that increased TGFβ in the tumor microenvironment is a primary mechanism of immune evasion by excluding CD8$^+$ T cells from the tumor. TGFβ-inhibitor agent and anti-PD-L1 antibodies reduced TGFβ signaling in stromal cells, facilitated CD8$^+$ T cells penetration into the tumors, and resulting in profound anti-tumor immunity and tumor regression (Mariathasan, et al., 2018, *Nature*, 554:544-548, Tauriello, et al., 2018, *Nature*, 554:538-543). Compounds of the present disclosure, which can for example inhibit TGFβ type I receptor (TGFβ-RI), are useful in treating or preventing diseases or disorders related to aberrant TGFβ regulation such as cancer, fibrosis and immune related diseases.

In some embodiments, the present disclosure provides a method of treating a disease or disorder (e.g., cancer, fibrosis, or immune related diseases) in a subject in need thereof. In some embodiments, the method comprises administering a therapeutically effective amount of a compound of the present disclosure (e.g., a compound of any of Formula I (e.g., Formula I-1, I-2, I-3, I-4, or I-5), Formula II (e.g., Formula II-1, II-2, II-3, II-4, II-5, II-6, or II-7), Formula II-S, Formula III (e.g., Formula III-1, III-2, or III-3), Formula III-S, Formula IV, or any of Compound Nos. 1-90, or a pharmaceutically acceptable salt thereof) or a therapeutically effective amount of a pharmaceutical composition described herein.

The administering herein is not limited to any particular route of administration. For example, in some embodiments, the administering can be orally, nasally, transdermally, pulmonary, inhalationally, buccally, sublingually, intraperintoneally, subcutaneously, intramuscularly, intravenously, rectally, intrapleurally, intrathecally and parenterally. In some embodiments, the administering is orally.

Various diseases or disorders can be treated by the methods herein. Non-limiting examples include cancer, such as colon cancer, melanoma, hepatocellular carcinoma (HCC), renal cancer, glioblastoma (GBM), pancreatic cancer, myelodysplastic syndrome (MDS), lung cancer, and gastric cancer, and fibrosis, such as liver fibrosis and chronic kidney disease. In some embodiments, the cancer can be melanoma, papillary thyroid tumours, cholangiocarcinomas, colon cancer, ovarian cancer, lung cancer, leukaemias, lymphoid malignancies, multiple myeloma, carcinomas and sarcomas in the liver, kidney, bladder, prostate, breast and pancreas, and primary and recurrent solid tumours of the skin, colon, thyroid, lungs and ovaries.

In some embodiments, the method is for treating cancer, which method comprises administering to a subject in need thereof a therapeutically effective amount of a compound of the present disclosure (e.g., a compound of any of Formula I (e.g., Formula I-1, I-2, I-3, I-4, or I-5), Formula II (e.g., Formula II-1, II-2, II-3, II-4, II-5, II-6, or II-7), Formula II-S, Formula III (e.g., Formula III-1, III-2, or III-3), Formula III-S, Formula IV, or any of Compound Nos. 1-90, or a pharmaceutically acceptable salt thereof) or a pharmaceutical composition described herein. In some embodiments, the cancer is colon cancer, melanoma, hepatocellular carcinoma (HCC), renal cancer, glioblastoma (GBM), pancreatic cancer, myelodysplastic syndrome (MDS), lung cancer, and/or gastric cancer. In some embodiments, the cancer can be melanoma, papillary thyroid tumours, cholangiocarcinomas, colon cancer, ovarian cancer, lung cancer, leukaemias, lymphoid malignancies, multiple myeloma, carcinomas and sarcomas in the liver, kidney, bladder, prostate, breast and pancreas, and primary and recurrent solid tumours of the skin, colon, thyroid, lungs and ovaries.

In some embodiments, the present disclosure provides a method of treating a fibrosis (e.g., liver fibrosis) in a subject in need thereof. In some embodiments, the method comprises administering to the subject a therapeutically effective amount of a compound of the present disclosure (e.g., a compound of any of any of Formula I (e.g., Formula I-1, I-2, I-3, I-4, or I-5), Formula II (e.g., Formula II-1, II-2, II-3, II-4, II-5, II-6, or II-7), Formula II-S, Formula III (e.g., Formula III-1, III-2, or III-3), Formula III-S, Formula IV, or any of Compound Nos. 1-90, or a pharmaceutically acceptable salt thereof) or a pharmaceutical composition described herein.

In some embodiments, the present disclosure also provides a method of inhibiting TGF-beta signaling, e.g., selectively inhibiting TGFβ type I receptor (TGFβ-RI) over TGFβ type II receptor (TGFβ-RII), in a subject in need thereof. In some embodiments, the method comprises administering an effective amount of a compound of the present disclosure (e.g., a compound of any of Formula I (e.g., Formula I-1, I-2, I-3, I-4, or I-5), Formula II (e.g., Formula II-1, II-2, II-3, II-4, II-5, II-6, or II-7), Formula II-S, Formula III (e.g., Formula III-1, III-2, or III-3), Formula III-S, Formula IV, or any of Compound Nos. 1-90, or a pharmaceutically acceptable salt thereof) or an effective amount of a pharmaceutical composition described herein. In some embodiments, the subject suffers from cancer (e.g., as described herein). In some embodiments, the subject suffers from fibrosis (e.g., as described herein). In some embodiments, the subject suffers from an immune disease or disorder.

Compounds of the present disclosure can be used as a monotherapy or in a combination therapy. In some embodiments, compounds of the present disclosure can be administered as the only active ingredient(s). In some embodiments, compounds of the present disclosure can be used in combination with conventional surgery or radiotherapy, immunotherapy, cell therapy, therapeutic antibodies, or chemotherapy. In some embodiments, compounds of the present disclosure can also be co-administered with an additional pharmaceutically active compound, either concurrently or sequentially in any order, to the subject in need thereof. In some embodiments, the additional pharmaceutically active compound can be a chemotherapeutic agent, a therapeutic antibody, etc. Any of the known chemotherapeutics, immunotherapy, cell therapy, or therapeutic antibodies can be used in combination with the compounds of the present disclosure. Some examples of such additional pharmaceutically active compounds, such as chemotherapeutics, are described in U.S. Patent Publication No. 20090048269. Some examples of such additional pharmaceutically active compounds also include immunotherapy agents, which can be an anti-PD-1 antibody and/or anti-PD-L1 antibody, including any of those known in the art, such as Keytruda (pembrolizumab), Opdivo (nivolumab), etc.

Dosing regimen including doses can vary and be adjusted, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

Definitions

It is meant to be understood that proper valences are maintained for all moieties and combinations thereof.

It is also meant to be understood that a specific embodiment of a variable moiety herein can be the same or different as another specific embodiment having the same identifier.

Suitable groups for in compounds of Formula I, II, II-S, III, III-S, or IV, or subformula thereof, as applicable, are independently selected. The described embodiments of the present invention can be combined. Such combination is contemplated and within the scope of the present invention. For example, it is contemplated that embodiments defined for any of $R^1$, $R^2$, $R^3$, $R^4$, A, Het of Formula I can be combined with embodiments defined for any other of $R^1$, $R^2$, $R^3$, $R^4$, A, Het of Formula I, as applicable. Combinations of other variables for other Formulae should be understood similarly.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high performance liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers including racemic mixtures.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

As used herein, the term "compound(s) of the present disclosure" or "compound(s) of the present invention" refers to any of the compounds described herein according to Formula I (e.g., Formula I-1, I-2, I-3, I-4, or I-5), Formula II (e.g., Formula II-1, II-2, II-3, II-4, II-5, II-6, or II-7), Formula II-S, Formula III (e.g., Formula III-1, III-2, or III-3), Formula III-S, Formula IV, or any of Compound Nos. 1-90, isotopically labeled compound(s) thereof (such as a deuterated analog wherein one of the hydrogen atoms is substituted with a deuterium atom with an abundance above its natural abundance), possible stereoisomers thereof (including diastereoisomers, enantiomers, and racemic mixtures), tautomers thereof, conformational isomers thereof, and/or pharmaceutically acceptable salts thereof (e.g., acid addition salt such as HCl salt or base addition salt such as Na salt). Hydrates and solvates of the compounds of the present disclosure are considered compositions of the present disclosure, wherein the compound(s) is in association with water or solvent, respectively.

Compounds of the present disclosure can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

As used herein, the phrase "administration" of a compound, "administering" a compound, or other variants thereof means providing the compound or a prodrug of the compound to the individual in need of treatment.

As used herein, the term "alkyl" as used by itself or as part of another group refers to a straight- or branched-chain aliphatic saturated hydrocarbon. In some embodiments, the alkyl which can include one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is a straight chain $C_{1-10}$ alkyl group. In another embodiment, the alkyl group is a branched chain $C_{3-10}$ alkyl group. In another embodiment, the alkyl group is a straight chain $C_{1-6}$ alkyl group. In another embodiment, the alkyl group is a branched chain $C_{3-6}$ alkyl group. In another embodiment, the alkyl group is a straight chain $C_{1-4}$ alkyl group. For example, a $C_{1-4}$ alkyl group as used herein refers to a group selected from methyl, ethyl, propyl (n-propyl), isopropyl, butyl (n-butyl), sec-butyl, tert-butyl, and isobutyl. An optionally substituted $C_{1-4}$ alkyl group refers to the $C_{1-4}$ alkyl group as defined, optionally substituted with one or more permissible substituents as described herein.

As used herein, the term "alkenyl" as used by itself or as part of another group refers to an alkyl group as defined above containing one, two or three carbon-to-carbon double bonds. In one embodiment, the alkenyl group is a $C_{2-6}$ alkenyl group. In another embodiment, the alkenyl group is a $C_{2-6}$ alkenyl group. Non-limiting exemplary alkenyl groups include ethenyl, propenyl, isopropenyl, butenyl, sec-butenyl, pentenyl, and hexenyl.

As used herein, the term "alkynyl" as used by itself or as part of another group refers to an alkyl group as defined above containing one to three carbon-to-carbon triple bonds. In one embodiment, the alkynyl has one carbon-carbon triple bond. In one embodiment, the alkynyl group is a $C_{2-6}$ alkynyl group. In another embodiment, the alkynyl group is a $C_{2-4}$ alkynyl group. Non-limiting exemplary alkynyl groups include ethynyl, propynyl, butynyl, 2-butynyl, pentynyl, and hexynyl groups.

As used herein, the term "alkoxy" as used by itself or as part of another group refers to a radical of the formula $OR^{a1}$, wherein $R^{a1}$ is an alkyl.

As used herein, the term "cycloalkoxy" as used by itself or as part of another group refers to a radical of the formula $OR^{a1}$, wherein $R^{a1}$ is a cycloalkyl.

As used herein, the term "haloalkyl" as used by itself or as part of another group refers to an alkyl substituted with one or more fluorine, chlorine, bromine and/or iodine atoms. In preferred embodiments, the haloalkyl is an alkyl group substituted with one, two, or three fluorine atoms. In one embodiment, the haloalkyl group is a $C_{1-10}$ haloalkyl group. In one embodiment, the haloalkyl group is a $C_{1-6}$ haloalkyl group. In one embodiment, the haloalkyl group is a $C_{1-4}$ haloalkyl group.

"Carbocyclyl" or "carbocyclic" as used by itself or as part of another group refers to a radical of a non-aromatic cyclic hydrocarbon group having from 3 to 10 ring carbon atoms ("$C_{3-10}$ carbocyclyl") and zero heteroatoms in the non-aromatic ring system. The carbocyclyl group can be either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Non-limiting exemplary carbocyclyl groups include cyclopropyl, cyclobutyl, cyclopentyl, cyclohexyl, cycloheptyl, cyclooctyl, norbornyl, decalin, adamantyl, cyclopentenyl, and cyclohexenyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-4}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl").

"Heterocyclyl" or "heterocyclic" as used by itself or as part of another group refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" as used by itself or as part of another group refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system.

"Aralkyl" as used by itself or as part of another group refers to an alkyl substituted with one or more aryl groups, preferably, substituted with one aryl group. Examples of aralkyl include benzyl, phenethyl, etc. When an aralkyl is said to be optionally substituted, either the alkyl portion or the aryl portion of the aralkyl can be optionally substituted.

"Heteroaryl" as used by itself or as part of another group refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" as used by itself or as part of another group refers to an alkyl substituted with one or more heteroaryl groups, preferably, substituted with one heteroaryl group. When a heteroaralkyl is said to be optionally substituted, either the alkyl portion or the heteroaryl portion of the heteroaralkyl can be optionally substituted.

An "optionally substituted" group, such as an optionally substituted alkyl, optionally substituted alkenyl, optionally substituted alkynyl, optionally substituted carbocyclyl, optionally substituted heterocyclyl, optionally substituted aryl, and optionally substituted heteroaryl groups, refers to the respective group that is unsubstituted or substituted. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent can be the same or different at each position. Typically, when substituted, the optionally substituted groups herein can be substituted with 1-5 substituents. Substituents can be a carbon atom substituent, a nitrogen atom substituent, an oxygen atom substituent or a sulfur atom substituent, as applicable.

Unless expressly stated to the contrary, combinations of substituents and/or variables are allowable only if such combinations are chemically allowed and result in a stable compound. A "stable" compound is a compound that can be prepared and isolated and whose structure and properties remain or can be caused to remain essentially unchanged for a period of time sufficient to allow use of the compound for the purposes described herein (e.g., therapeutic administration to a subject).

In some embodiments, the "optionally substituted" non-aromatic group herein can be unsubstituted or substituted with 1, 2, or 3 substituents independently selected from F, Cl, —OH, oxo (as applicable), $C_{1-4}$ alkyl, $C_{2-4}$ alkenyl, $C_{2-4}$ alkynyl, $C_{1-4}$ alkoxy, $C_{3-4}$ cycloalkyl, $C_{3-6}$ cycloalkoxy, phenyl, 5 or 6 membered heteroaryl containing 1, 2, or 3 ring heteroatoms independently selected from O, S, and N, 4-7 membered heterocyclyl containing 1 or 2 ring heteroatoms independently selected from O, S, and N, wherein each of the alkyl, alkenyl, alkynyl, alkoxy, cycloalkyl, cycloalkoxy phenyl, heteroaryl, and heterocyclyl, is optionally substituted with 1, 2, or 3 substituents independently selected from F, —OH, oxo (as applicable), $C_{1-4}$ alkyl, fluoro-substituted $C_{1-4}$ alkyl (e.g., $CF_3$), $C_{1-4}$ alkoxy and fluoro-substituted $C_{1-4}$ alkoxy. In some embodiments, the "optionally substituted" aromatic group (including aryl and heteroaryl groups) herein can be unsubstituted or substituted with 1, 2, or 3 substituents independently selected from F, Cl, —OH, —CN, $C_{1-4}$ alkyl, $C_{2-4}$ alkenyl, $C_{2-4}$ alkynyl, $C_{1-4}$ alkoxy, $C_{3-4}$ cycloalkyl, $C_{3-4}$ cycloalkoxy, phenyl, 5 or 6 membered heteroaryl containing 1, 2 or 3 ring heteroatoms independently selected from O, S, and N, 4-7 membered heterocyclyl containing 1 or 2 ring heteroatoms independently selected from O, S, and N, wherein each of the alkyl, alkenyl, alkynyl, alkoxy, cycloalkyl, cycloalkoxy, phenyl, heteroaryl, and heterocyclyl, is optionally substituted with 1, 2, or 3 substituents independently selected from F, —OH, oxo (as applicable), $C_{1-4}$ alkyl, fluoro-substituted $C_{1-4}$ alkyl, $C_{1-4}$ alkoxy and fluoro-substituted $C_{1-4}$ alkoxy.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{aa}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^{-z}$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^{aa}$ is, independently, selected from $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups; each instance of R$^{ff}$ is, independently, selected from hydrogen, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal RU substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $BPh_4^-$, $Al(OC(CF_3)_3)_4^-$, and a carborane anion (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^-$, $SO_4^{2-}$, $S_2O_3^{2-}$ carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2R^{aa}$, —C(=O)N($R^{bb}$)$_2$, —C(=NR$^{bb}$)$R^{aa}$, —C(=NR$^{bb}$)OR$^{aa}$, —C(=NR$^{bb}$)N(R$^{bb}$)$_2$, —C(=O)NR$^{bb}$SO$_2R^{aa}$, —C(=S)N(R$^{bb}$)$_2$, —C(=O)SR$^{aa}$, or —C(=S)SR$^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2R^{aa}$, —SO$_2R^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2R^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2R^{aa}$, —SO$_2R^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2R^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl, ar-$C_{1-10}$ alkyl, heteroar-$C_{1-10}$ alkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protective Groups in Organic Synthesis*, T. W. Greene and P. G. M. Wuts, 3$^{rd}$ edition, John Wiley & Sons, 1999, incorporated by reference herein.

Exemplary oxygen atom substituents include, but are not limited to, —R$^{aa}$, —C(=O)SR$^{aa}$, —C(=O)R$^{aa}$, —CO$_2R^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2R^{aa}$, —Si(R$^{aa}$)$_3$, —P(R$^{cc}$)$_2$, —P(R$^{cc}$)$_3^+$X$^-$, —P(OR$^{cc}$)$_2$, —P(OR$^{cc}$)$_3^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protective Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, alkyl ethers or substituted alkyl ethers such as methyl, allyl, benzyl, substituted benzyls such as 4-methoxybenzyl, methoxylmethyl (MOM), benzyloxymethyl (BOM), 2-methoxyethoxymethyl (MEM), etc., silyl ethers such as trymethylsilyl (TMS), triethylsilyl (TES), triisopropylsilyl (TIPS), t-butyldimethylsilyl (TBDMS), etc., acetals or ketals, such as tetrahydropyranyl (THP), esters such as formate, acetate, chloroacetate, dichloroacetate, trichloroacetate, trifluoroacetate, methoxyacetate, etc., carbonates, sulfonates such as methanesulfonate (mesylate), benzylsulfonate, and tosylate (Ts), etc.

The term "leaving group" is given its ordinary meaning in the art of synthetic organic chemistry, for example, it can refer to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

The term "subject" (alternatively referred to herein as "patient") as used herein, refers to an animal, preferably a mammal, most preferably a human, who has been the object of treatment, observation or experiment.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound described herein to a subject in need of such treatment.

EXAMPLES

The various starting materials, intermediates, and compounds of the preferred embodiments can be isolated and purified where appropriate using conventional techniques such as precipitation, filtration, crystallization, evaporation, distillation, and chromatography. Characterization of these compounds can be performed using conventional methods such as by melting point, mass spectrum, nuclear magnetic resonance, and various other spectroscopic analyses. Exemplary embodiments of steps for performing the synthesis of products described herein are described in greater detail infra.

Example 1. Synthesis of Compound 6

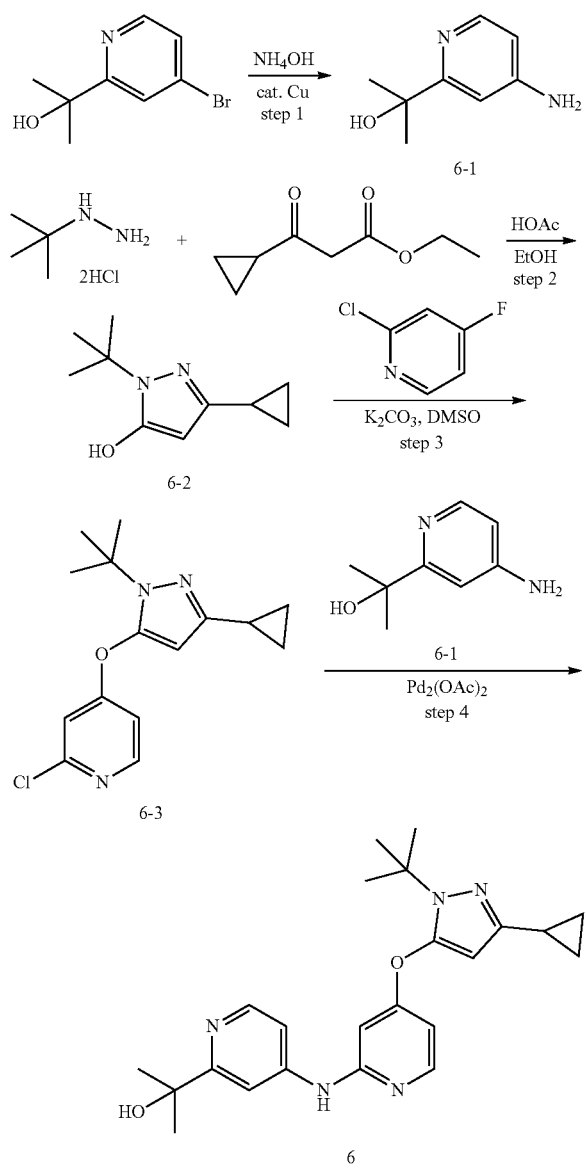

Step 1: To a solution of 2-(4-bromopyridin-2-yl)propan-2-ol (2 g, 9.26 mmol) in ammonia hydroxide (80 mL) was added Cu powder (297 mg, 4.67 mmol), and the mixture was stirred at room temperature for 30 minutes and then heated to 100° C. in a sealed tube overnight. The reaction mixture was cooled to room temperature and extracted with 2-methyl tetrahydrofuran. The combined organic layer was dried with $Na_2SO_4$, filtered and concentrated to give a residue which was purified by column chromatography (MeOH/$CH_2Cl_2$, 0 to 2%) to afford 6-1.

Step 2: A solution of t-butylhydrazine dihydrochlride (600 mg, 3.72 mmol), ethyl 3-cyclopropyl-3-oxopropanoate (1.06 g, 6.79 mmol) and HOAc (817 mg, 13.60 mmol) in EtOH (20 mL) was heated at 80° C. overnight. The resulting mixture was then concentrated and diluted with water and EtOAc. The mixture was neutralized to pH 7 with saturated aqueous $NaHCO_3$ solution and extracted with EtOAc. The combined organic layer was washed with brine, dried and concentrated. The residue was purified by column chromatography (hexane/EtOAc=1/1) to afford 6-2.

Step 3: To a mixture of 6-2 (380 mg, 2.11 mmol) and $K_2CO_3$ (583 mg, 4.22 mmol) in DMSO (10 mL) was added 2-chloro-4-fluoropyridine (305 mg, 2.32 mmol) drop wise at room temperature. The mixture was heated at 80° C. for 2 hours. The resulting mixture was diluted with EtOAc and washed with water. The combined organic layer was washed with brine, dried and concentrated. The residue was purified by prep-TLC (hexane/EtOAc=5/1) to afford 6-3.

Step 4: To a solution of 6-3 (150 mg, 0.51 mmol) and 6-1 (78 mg, 0.51 mmol) in dioxane (3 mL) was added $Cs_2CO_3$ (251 mg, 0.77 mmol), XantPhos (59 mg, 0.10 mmol) and Pd(OAc)$_2$ (11 mg, 0.05 mmol) at room temperature. The mixture was heated at 100° C. for 18 hours under nitrogen atmosphere. Then the mixture was cooled and filtered. The filter cake was washed with dichloromethane, and the filtrate was concentrated under reduced pressure. The residue was purified by a prep-HPLC (aqueous $NH_4HCO_3$ (10 mmol/L)/ acetonitrile (44%-53%) to afford 6. LCMS (ES, m/z): [M+H]$^+$=408.4; HNMR (400 MHz, DMSO-$d_6$, ppm): δ 9.57 (s, 1H), 8.23 (d, J=5.2 Hz, 1H), 8.21 (d, J=6.0 Hz, 1H), 7.73-7.69 (m, 2H), 6.68 (dd, J=5.6, 2.4 Hz, 1H), 6.55 (d, J=2.4 Hz, 1H), 5.74 (s, 1H), 5.11 (s, 1H), 1.87-1.80 (m, 1H), 1.48 (s, 9H), 1.41 (s, 6H), 0.90-0.81 (m, 2H), 0.68-0.60 (m, 2H).

Example 2. Synthesis of Compound 1

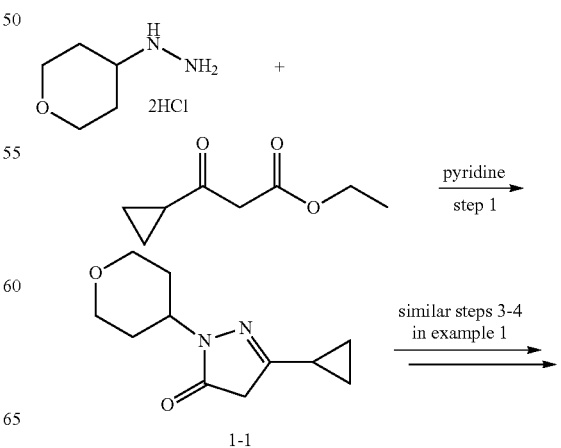

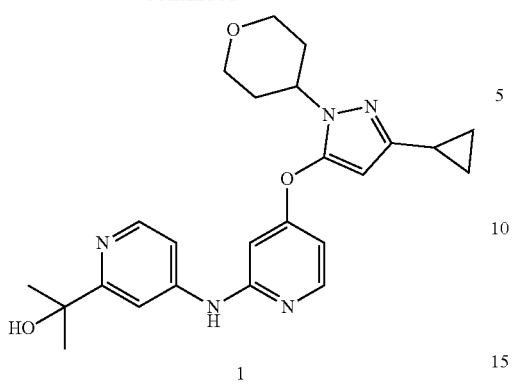

1

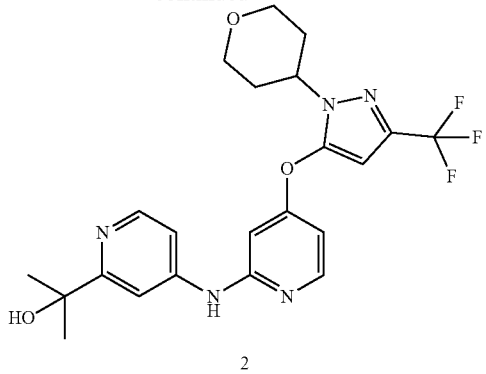

2

Step 1: To solution of (tetrahydropyran-4-yl)-hydrazine dihydrochloride (3.5 g, 18.51 mmol) was added ethyl 3-cyclopropyl-3-oxopropanoate (2.42 g, 15.49 mmol), and the mixture was stirred at room temperature overnight. The reaction was diluted with water and EtOAc. The aqueous phase was separated and extracted with EtOAc. The combined organic layer was washed with HCl (M) and brine, dried with Na$_2$SO$_4$, filtered and concentrated to give a residue which was purified by column chromatography (petroleum ether/EtOAc=1/1) to afford 1-1.

Followed the similar steps in example 1 to synthesize 1. LCMS (ES, m/z): [M+H]$^+$=436.2; HNMR (300 MHz, DMSO-d$_6$, ppm): δ 9.63 (s, 1H), 8.22 (d, J=4.5 Hz, 2H), 7.72 (d, J=1.5 Hz, 2H), 6.69 (dd, J=4.5, 1.5 Hz, 1H), 6.47 (s, 1H), 5.76 (s, 1H), 5.11 (s, 1H), 4.18-4.20 (m, 1H), 3.90 (dd, J=2.7, 8.7 Hz, 2H), 3.33-3.40 (m, 2H), 1.96-2.02 (m, 2H), 1.89-1.85 (m, 1H), 1.73-1.69 (m, 2H), 1.41 (s, 6H), 0.90-0.85 (m, 2H), 0.69-0.64 (m, 2H).

Step 1: A mixture of (tetrahydropyran-4-yl)hydrazine dihydrochloride (1.50 g, 7.93 mmol) and ethyl 4,4,4-trifluoro-3-oxobutanoate (1.97 g, 10.70 mmol) in HOAc (15 mL) was irradiated under microwave at 120° C. for 1.5 hours. The reaction mixture was cooled, diluted with water and extracted with EtOAc. The combined organic layer was dried over anhydrous Na$_2$SO$_4$, filtered and concentrated to give a residue which was purified by a prep-TLC (petroleum ether/EtOAc=1:1) to afford 2-1.

Followed the similar steps in example 1 to synthesize 2. LCMS (ES, m/z): [M+H]$^+$=464.3; HNMR (400 MHz, DMSO-d$_6$, ppm): δ 9.62 (s, 1H), 8.28 (d, J=5.6 Hz, 1H), 8.24 (d, J=5.6 Hz, 1H), 7.74-7.71 (m, 2H), 6.77 (dd, J=6.0, 2.4 Hz, 1H), 6.71 (s, 1H), 6.54 (d, J=2.4 Hz, 1H), 5.11 (bs, 1H), 4.55-4.49 (m, 1H), 3.96-3.92 (m, 2H), 3.42-3.47 (m, 2H), 2.06-1.96 (m, 2H), 1.86-1.83 (m, 2H), 1.42 (s, 6H); FNMR (376 MHz, DMSO-d$_6$, ppm): δ −61.25.

Example 3. Synthesis of Compound 2

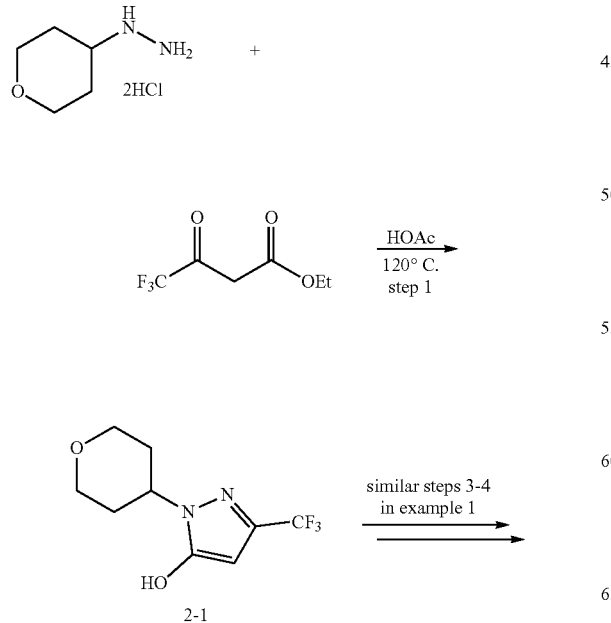

Example 4. Synthesis of Compound 4

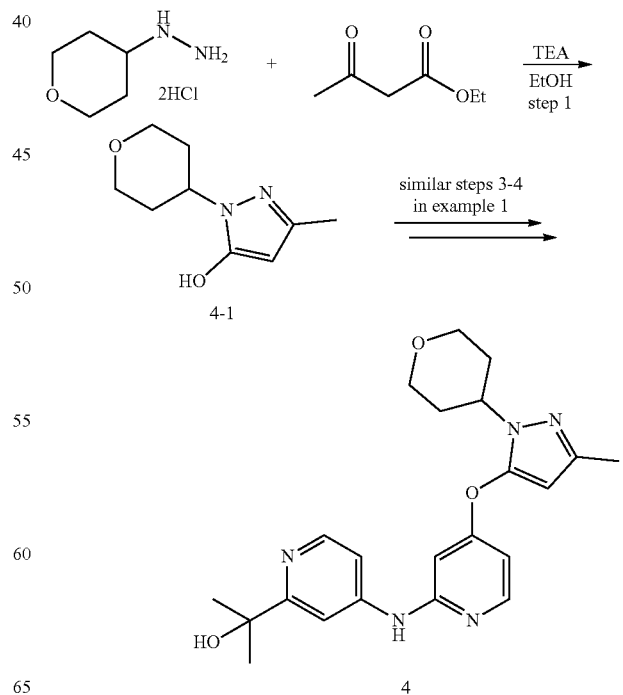

Step 1: To a mixture of (tetrahydropyran-4-yl)hydrazine dihydrochloride (5.00 g, 26.44 mmol) and ethyl acetoacetate (4.65 g, 35.73 mmol) in EtOH (100 mL) was added TEA (10.89 g, 107.62 mmol) dropwise at room temperature, and the mixture was heated at 80° C. for 4 hours under nitrogen atmosphere. The mixture was cooled to room temperature and concentrated to afford 4-1.

Followed the similar steps in example 1 to synthesize 4 as a mono formic acid salt. LCMS (ES, m/z): [M+H]$^+$=410.3; HNMR (300 MHz, DMSO-d$_6$, ppm): δ 9.60 (s, 1H), 8.23 (d, J=5.7 Hz, 2H), 8.16 (s, 1H), 7.72 (s, 1H), 7.69-7.70 (m, 1H), 6.70 (dd, J=5.7, 2.4 Hz, 1H), 6.51 (d, J=2.4 Hz, 1H), 5.87 (s, 1H), 5.11 (bs, 1H), 4.25-4.17 (m, 1H), 3.91 (dd, J=11.7, 3.9 Hz, 2H), 3.38 (t, J=11.7 Hz, 2H), 2.19 (s, 3H), 2.07-1.94 (m, 2H), 1.78-1.65 (m, 2H), 1.41 (s, 6H).

Example 5. Synthesis of Compounds 18 and 19

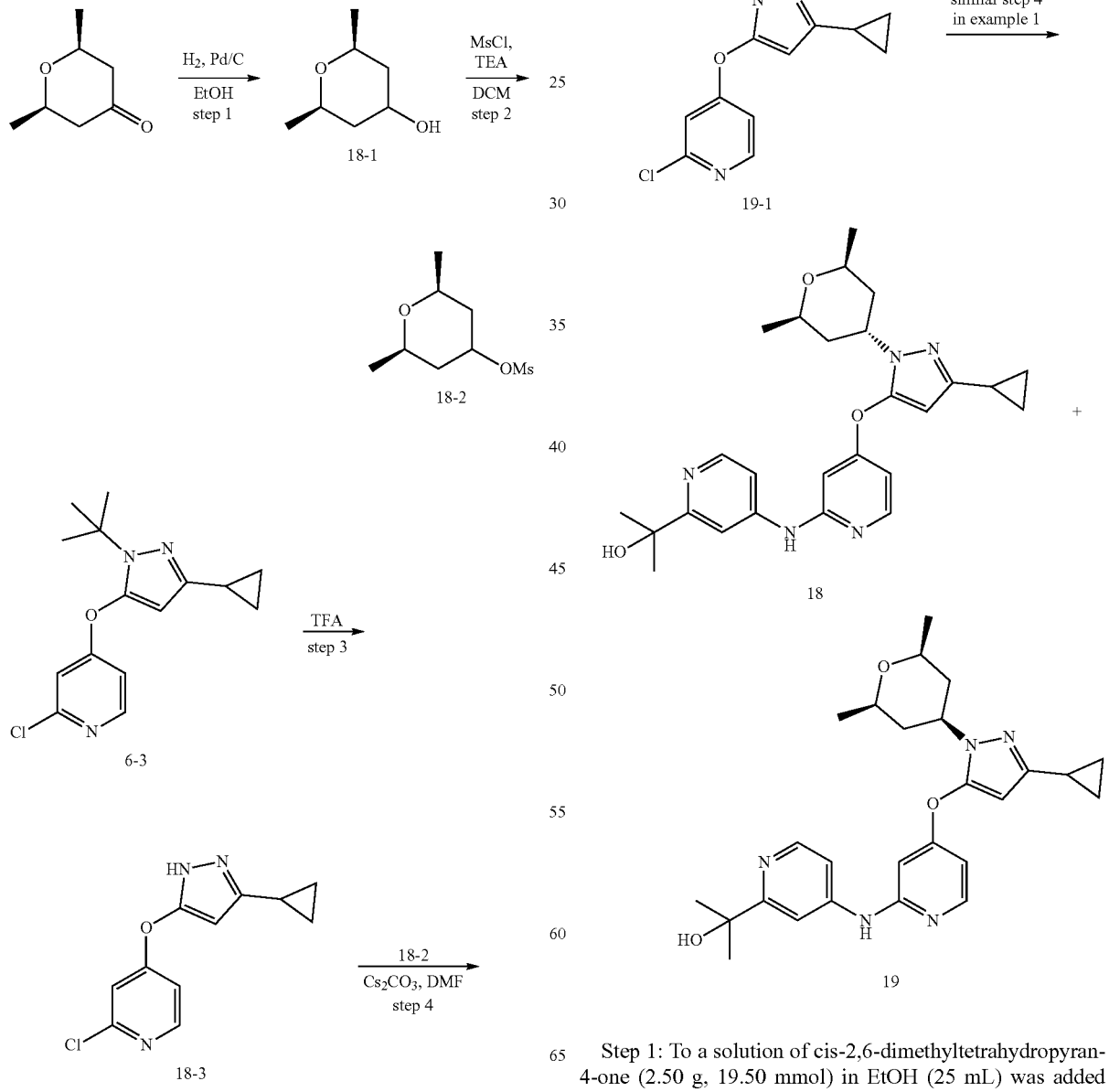

Step 1: To a solution of cis-2,6-dimethyltetrahydropyran-4-one (2.50 g, 19.50 mmol) in EtOH (25 mL) was added Pd/C (10%, 250 mg), and the mixture was stirred at 35° C.

under H₂ atmosphere for 18 hours. The mixture was filtered through Celite and the filtrate was concentrated to afford 18-1.

Step 2: To a solution of 18-1 (1.00 g, 7.68 mmol) and TEA (2.33 g, 23.02 mmol) in DCM (20 mL) was added methanesulfonyl chloride (1.32 g, 11.52 mmol) at 0° C. The mixture was stirred at room temperature for 3 hours, and then concentrated to afford 18-2, which was used in next step without further purification.

Step 3: A solution of 6-3 (4.4 g, 15.08 mmol) in TFA (20 mL) was heated at 80° C. for 8 hours. The resulting mixture was then concentrated under vacuum, and the residue was neutralized to pH 7 with saturated aqueous Na₂CO₃ solution. The mixture was extracted with EtOAc, and the combined organic layer was washed with brine, dried over anhydrous Na₂SO₄, filtered and concentrated. The residue was purified by column chromatography (petroleum ether/EtOAc=5/1 to 2/1) to afford 18-3.

Step 4: A mixture of 18-3 (200 mg, 0.85 mmol), 18-2 (300 mg, 1.44 mmol) and Cs₂CO₃ (829 mg, 2.54 mmol) in DMF (4 mL) was stirred at room temperature for 3 hours. The mixture was diluted with water and extracted with EtOAc. The combined organic layer was washed with brine, dried over anhydrous Na₂SO₄, filtered and concentrated. The residue was purified by C18 silica gel column chromatography (MeCN in water, 50% to 70%) to afford 18-4 and 19-1, respectively.

Followed the similar step in example 1 to synthesize 18 and 19, respectively. 18 LCMS (ES, m/z): [M+H]⁺=464.3; HNMR (400 MHz, DMSO-d₆, ppm): δ 9.62 (bs, 1H), 8.20 (d, J=6.0 Hz, 1H), 8.18 (d, J=6.0 Hz, 1H), 7.69-7.80 (m, 2H), 6.61 (d, J=6.0 Hz, 1H), 6.50-6.52 (m, 1H), 5.77 (s, 1H), 5.20-5.30 (m, 1H), 4.89-4.93 (m, 1H), 4.02-4.12 (m, 2H), 2.02-1.83 (m, 3H), 1.73-1.55 (m, 2H), 1.43 (s, 6H), 1.06 (d, J=6.4 Hz, 6H), 1.01-0.94 (m, 2H), 0.76-0.66 (m, 2H). 19 LCMS (ES, m/z): [M+H]⁺=464.5; HNMR (300 MHz, DMSO-d₆, ppm): δ 9.49 (s, 1H), 8.22 (d, J=6.0 Hz, 1H), 8.15 (d, J=6.0 Hz, 1H), 7.69-7.71 (m, 2H), 6.54-6.57 (m, 1H), 6.49 (s, 1H), 5.71 (s, 1H), 5.12 (s, 1H), 4.70-4.62 (m, 1H), 3.66-3.62 (m, 2H), 2.09-1.96 (m, 1H), 1.92-1.88 (m, 2H), 1.66-1.54 (m, 2H), 1.41 (s, 6H), 1.16 (d, J=6.3 Hz, 6H), 1.02-0.92 (m, 2H), 0.69-0.62 (m, 2H).

Example 6 Synthesis of Compound 26

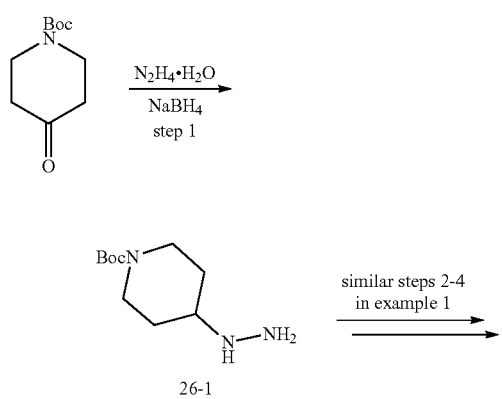

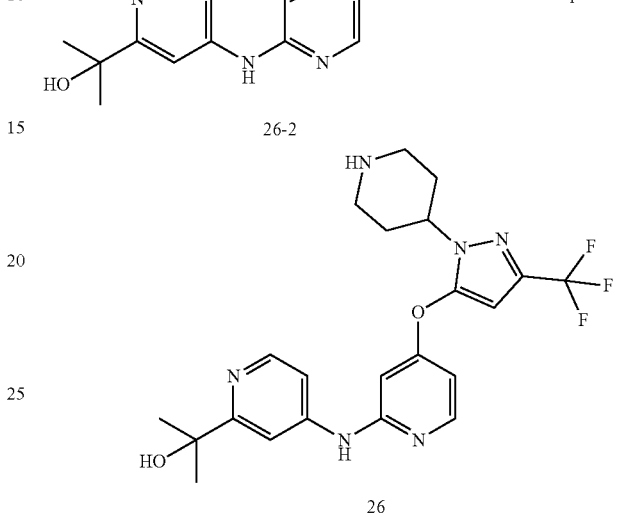

Step 1: A mixture of t-butyl 4-oxo-1-piperidinecarboxylate (1.0 g, 5.02 mmol) and hydrazine hydrate (160 mg, 3.20 mmol) in MeOH (6 mL) was stirred at room temperature for 2 hours. NaBH₄ (630 mg, 16.65 mmol) was then added. The reaction was stirred at room temperature overnight, and then was concentrated to afford 26-1 which was used directly to next step without further purification.

Followed the similar steps in example 1 to synthesize 26-2.

Step 2: To a solution of 26-2 (150 mg, 0.27 mmol) in DCM (3.0 mL) was add TFA (1.0 mL). Then the mixture was stirred overnight and concentrated. The residue was purified by a prep-HPLC (acetonitrile with 0.05% of aqueous TFA: 20% to 45%) to give 26. LCMS (ES, m/z): [M+H]⁺=463.1; HNMR (400 MHz, DMSO-d₆, ppm): δ 9.65 (s, 1H), 8.22 (d, J=6.0 Hz, 1H), 8.19 (d, J=5.2 Hz, 1H), 7.70-7.68 (m, 2H), 6.72-6.70 (m, 1H), 6.65 (s, 1H), 6.50 (d, J=2.0 Hz, 1H), 5.11 (s, 1H), 4.28-4.23 (m, 1H), 3.01-2.97 (m, 2H), 2.55-2.49 (m, 2H), 1.86-1.75 (m, 4H), 1.37 (s, 6H).

Example 7 Synthesis of Compound 39

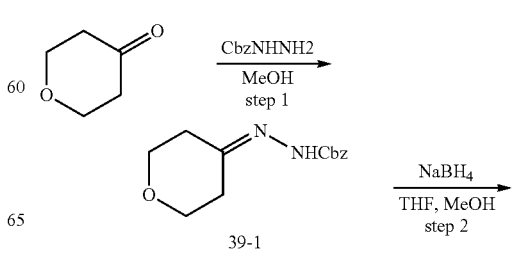

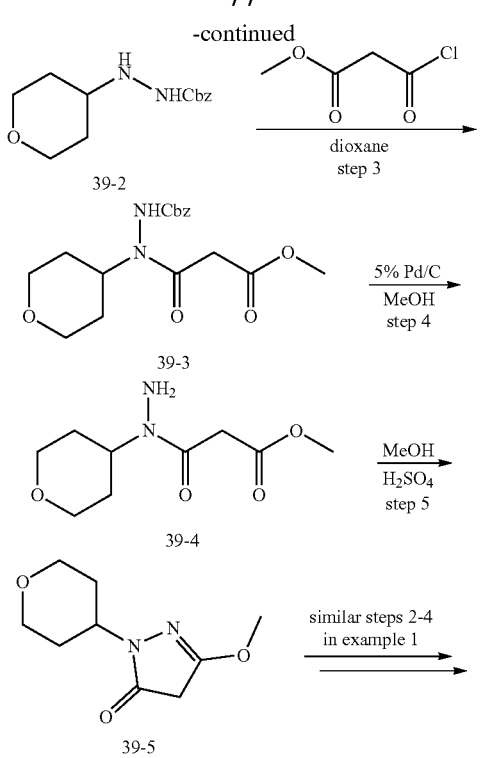

ethyl acetate. The combined organic layer was washed with brine, dried over sodium sulfate, filtered and concentrated. The residue was purified by column chromatography on silica gel (petroleum ether:EtOAc/petroleum ether=1/1) to afford 39-3.

Step 4: To a solution of 39-3 (430 mg, 1.23 mmol) in methanol (20 mL) was added 5% Pd/C (110 mg). Then the mixture was stirred under $H_2$ atmosphere for 2 hours. The mixture was filtered, and the filtrate was concentrated to afford 39-4.

Step 5: To a solution of 39-4 (900 mg, 4.16 mmol) in methanol (20 mL) was added conc. $H_2SO_4$ (2.7 g, 27.00 mmol). The mixture was stirred at room temperature for 1 hour and then heated at 70° C. for 60 hours under $N_2$ atmosphere. The mixture was concentrated, diluted with water and extracted with ethyl acetate. The combined organic layer was washed with brine, dried over sodium sulfate, filtered and concentrated to afford 39-5.

Followed the similar steps in example 1 to synthesize 39. LCMS (ES, m/z): [M+H]$^+$=426.1; HNMR (400 MHz, DMSO-d$_6$, ppm): δ 9.57 (s, 1H), 8.20-8.18 (m, 2H), 7.69-7.67 (m, 2H), 6.68 (dd, J=5.6, 2.4 Hz, 1H), 6.50 (d, J=2.0 Hz, 1H), 5.56 (s, 1H), 5.10 (s, 1H), 4.17-4.15 (m, 1H), 3.88-3.84 (m, 2H), 3.75 (s, 3H), 3.36-3.31 (m, 2H), 1.96-1.92 (m, 2H), 1.67-1.65 (m, 2H), 1.19 (s, 6H).

Example 8 Synthesis of Compound 42

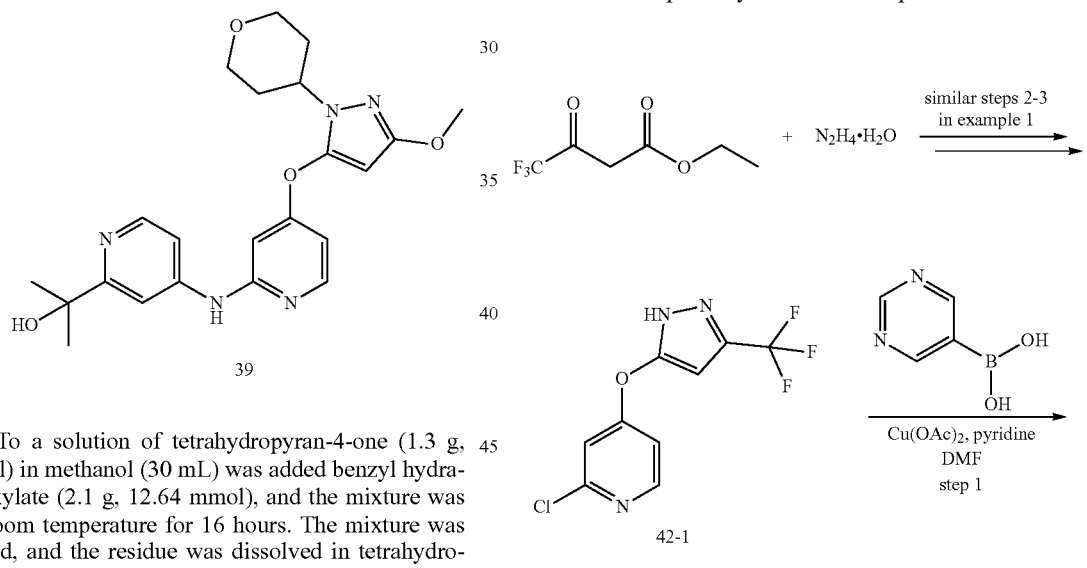

Step 1: To a solution of tetrahydropyran-4-one (1.3 g, 12.98 mmol) in methanol (30 mL) was added benzyl hydrazine carboxylate (2.1 g, 12.64 mmol), and the mixture was stirred at room temperature for 16 hours. The mixture was concentrated, and the residue was dissolved in tetrahydrofuran and then concentrated to give 39-1 which was used in next step without further purification.

Step 2: To a solution of 39-1 (3.5 g, 14.10 mmol) in tetrahydrofuran (30 mL) was added NaBH$_4$ (0.95 g, 25.11 mmol) at room temperature, and the mixture was stirred for 15 minutes. Then methanol (5 mL) was added dropwise at 0° C., and the reaction mixture was stirred at room temperature for 16 hours. Water was added dropwise at 0° C., and the mixture was stirred for 1.5 hours at room temperature. The reaction was diluted with water, and extracted with ethyl acetate. The combined organic layer was washed with brine, dried over sodium sulfate, filtered and concentrated to give 39-2.

Step 3: To a solution of 39-2 (2.6 g, 10.39 mmol) in 1,4-dioxane (50 mL) was added methyl 3-chloro-3-oxopropanoate (1.5 g, 10.99 mmol), and the mixture was heated at 100° C. for 3 hours. The reaction was quenched with saturated sodium bicarbonate solution and extracted with

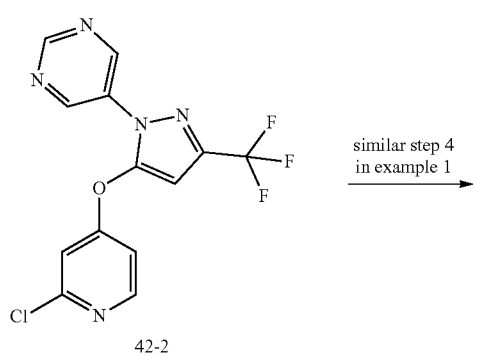

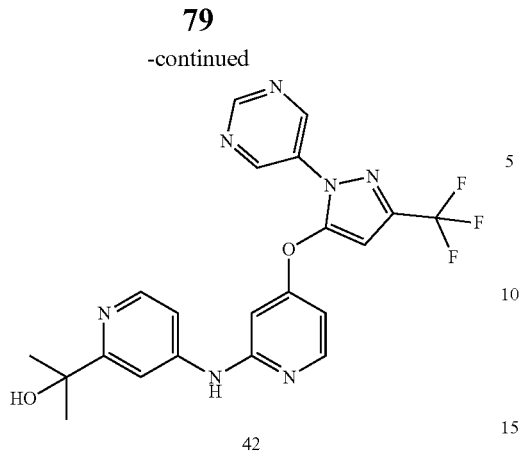

42

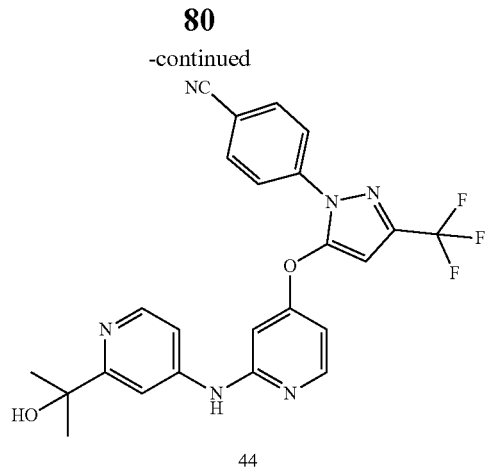

44

Followed the similar steps in example 1 to synthesize 42-1.

Step 1: To a mixture of 42-1 (352 mg, 1.34 mmol) and 5-pyrimidinylboronic acid (332 mg, 2.68 mmol) in NN-dimethylformamide (5 mL) was added cupric acetate (366 mg, 2.01 mmol) and pyridine (212 mg, 2.68 mmol) at room temperature. The mixture was heated at 40° C. for 48 hours under air atmosphere. After cooling to room temperature, the mixture was treated with saturated aqueous sodium bicarbonate solution and extracted with dichloromethane. The combined organic layer was washed with brine, dried over sodium sulfate, filtered and concentrated. The residue was purified by column chromatography on silica gel (petroleum ether to ethyl acetate/petroleum ether=1/1) to afford 42-2.

Followed the similar step in example 1 to synthesize 42. LCMS (ES, m/z): [M+H]$^+$=458.0; HNMR (400 MHz, CD$_3$OD, ppm): δ 9.19 (s, 3H), 8.26 (d, J=6.0 Hz, 1H), 8.19 (d, J=6.0 Hz, 1H), 7.85 (d, J=2.0 Hz, 1H), 7.66 (dd, J=6.0, 2.0 Hz, 1H), 6.79 (dd, J=6.0, 2.0 Hz, 1H), 6.67-6.66 (m, 2H), 1.50 (s, 6H). FNMR (376 MHz, CD$_3$OD, ppm): δ −65.11.

A mixture of 43 (60 mg, 0.12 mmol), zinc cyanide (22 mg, 0.19 mmol), zinc powder (2 mg, 0.03 mmol), 1,1'-bis(diphenylphosphino)ferrocene (26 mg, 0.047 mmol) and tris(dibenzylideneacetone)-dipalladium(0) (22 mg, 0.024 mmol) in dimethylacetamide (2 mL) was heated at 150° C. for 2 hours under microwave condition. Then the mixture was cooled and filtered. The filtrate was purified by a prep-HPLC (acetonitrile with 0.05% of aqueous TFA: 15% to 95%) to afford 44. LCMS (ES, m/z): [M+H]$^+$=481.1; HNMR (400 MHz, CD$_3$OD, ppm): δ 8.39 (d, J=6.0 Hz, 1H), 8.22 (d, J=6.8 Hz, 1H), 8.17-7.96 (m, 2H), 7.93-7.87 (m, 4H), 6.98 (dd, J=5.6, 2.0 Hz, 1H), 6.76 (d, J=2.0 Hz, 1H), 6.70 (s, 1H), 1.61 (s, 6H). FNMR (376 MHz, CD$_3$OD, ppm): δ −65.04.

Example 10 Synthesis of Compounds 46 and 47

Example 9 Synthesis of Compound 44

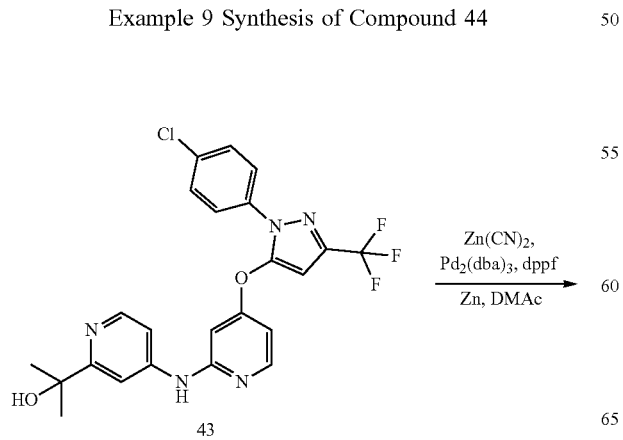

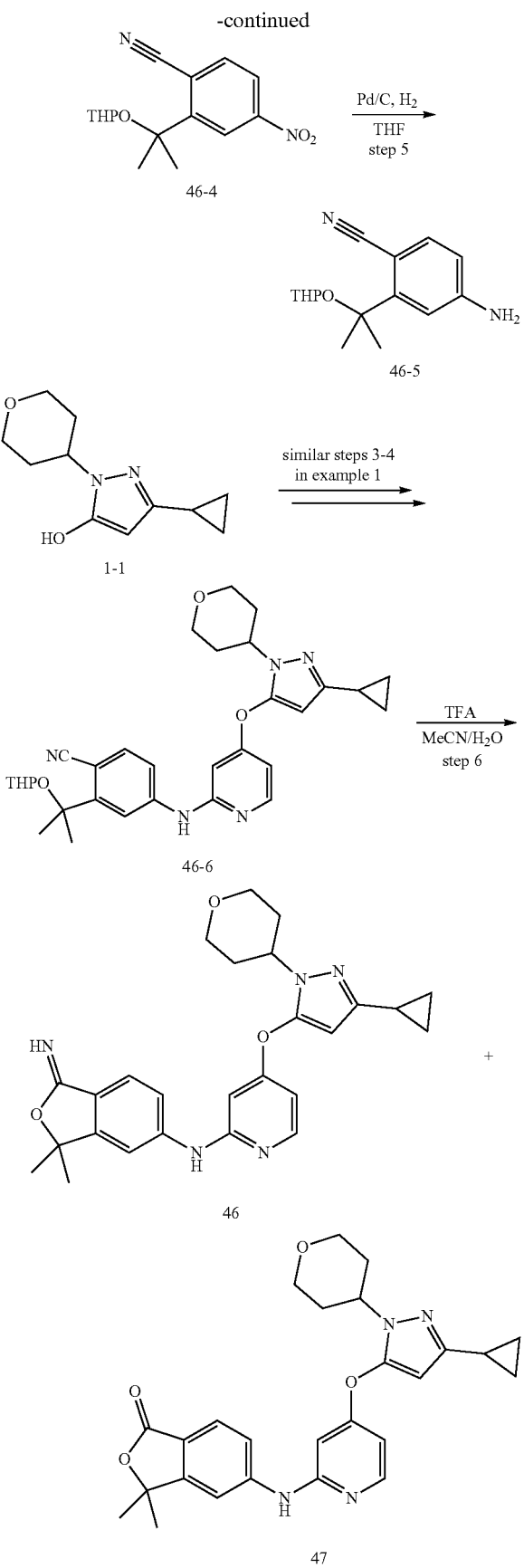

Step 1: To a solution of potassium nitrate (5.05 g, 49.95 mmol) in conc. sulfuric acid (50 mL) was added 2'-bromoacetophenone (8.0 g, 40.19 mmol) portion wise at −10° C. The mixture was stirred at 0° C. for 1 hour. Then the mixture was poured into ice-water and filtered. The filter cake was washed with water and purified by column chromatography on silica gel (petroleum ether:petroleum ether/ethyl acetate=8/1) to afford 46-1.

Step 2: To a solution of 46-1 (2.43 g, 9.96 mmol) in dichloromethane (20 mL) was added trimethylaluminium (2.0 M in toluene, 10 mL, 20 mmol) drop wise at 0° C. under $N_2$ atmosphere. The mixture was stirred at 0° C. for 1 hour, followed by quenching with aqueous ammonium chloride. The mixture was extracted with dichloromethane, and the combined organic layer was dried over sodium sulfate, filtered and concentrated. The residue was purified by column chromatography on silica gel (petroleum ether to EtOAc/petroleum ether=1/4) to afford 46-2.

Step 3: To a solution of 46-2 (777 mg, 2.99 mmol) in dichloromethane (20 mL) was added dihydropyran (504 mg, 5.99 mmol) and PPTS (75 mg, 0.30 mmol), and the mixture was stirred at room temperature for 16 hours. The mixture was concentrated and the residue was purified by column chromatography on silica gel (petroleum ether to EtOAc/petroleum ether=1/4) to afford 46-3.

Step 4: To a solution of 46-3 (892 mg, 2.59 mmol) in dimethylformamide (10 mL) was added zinc cyanide (1.17 g, 9.96 mmol), tris(dibenzylideneacetone)dipalladium (238 mg, 0.26 mmol) and 1,1'-bis(diphenylphosphino)ferrocene (288 mg, 0.52 mmol) at room temperature, and the mixture was heated at 110° C. for 16 hours under $N_2$ atmosphere. After cooling to room temperature, the reaction mixture was diluted with ethyl acetate, and washed with water and brine. The organic layer was dried over sodium sulfate, filtered and concentrated. The residue was purified by column chromatography on silica gel (petroleum ether to EtOAc/petroleum ether=1/5) to give 46-4.

Step 5: To a solution of 46-4 (260 mg, 0.90 mmol) in tetrahydrofuran (20 mL) was added 10% Pd/C (52 mg) at room temperature. The mixture was stirred for 3 hours under $H_2$ atmosphere. After filtration, the filtrate was concentrated and purified by column chromatography on silica gel (petroleum ether to EtOAc/petroleum ether=1/1) to give 46-5.

Followed the similar steps in example 1 to synthesize 46-7.

Step 6: To a solution of 46-7 (80 mg, 0.15 mmol) in $H_2O$ (1 mL) and MCN (3 mL) was added TFA (0.5 mL). The mixture was stirred at room temperature for 2 days and then concentrated. Then residue was purified by a prep-HPLC (acetonitrile with 0.05% of aqueous TFA: 25% to 70%) to afford 46 and 47. 46 (TFA salt). LCMS (ES, m/z): [M+H]$^+$=460.1; HNMR (400 MHz, DMSO-$d_6$, ppm): δ 11.20 (s, 1H), 10.96 (s, 1H), 10.15 (s, 1H), 8.25 (d, J=6.0 Hz, 1H), 8.09 (d, J=1.2 Hz, 1H), 8.04 (d, J=8.8 Hz, 1H), 7.78-7.75 (dd, J=8.8, 1.6 Hz, 1H), 6.77 (dd, J=6.0, 2.4 Hz, 1H), 6.53 (d, J=2.4 Hz, 1H), 5.75 (s, 1H), 4.19-4.12 (m, 1H), 3.88-3.84 (m, 2H), 3.36-3.30 (m, 2H), 2.00-1.91 (m, 2H), 1.87-1.80 (m, 1H), 1.71 (s, 6H), 1.69-1.65 (m, 2H), 0.85-0.83 (m, 2H), 0.63-0.65 (m, 2H). 47. LCMS (ES, m/z): [M+H]$^+$=461.1; HNMR (400 MHz, DMSO-$d_6$, ppm): δ 9.78 (s, 1H), 8.20 (d, J=5.6 Hz, 1H), 7.95 (d, J=1.2 Hz, 1H), 7.66-7.61 (m, 2H), 6.69 (dd, J=6.0, 2.4 Hz, 1H), 6.46 (d, J=2.0 Hz, 1H), 5.74 (s, 1H), 4.18-4.12 (m, 1H), 3.86 (dd, J=11.2, 3.2 Hz, 2H), 3.33 (t, J=11.2 Hz, 2H), 1.98-1.91 (m, 2H), 1.85-1.81 (m, 1H), 1.68-1.66 (m, 2H), 1.54 (s, 6H), 0.85-0.82 (m, 2H), 0.63-0.61 (m, 2H).

Example 11 Synthesis of Compound 56

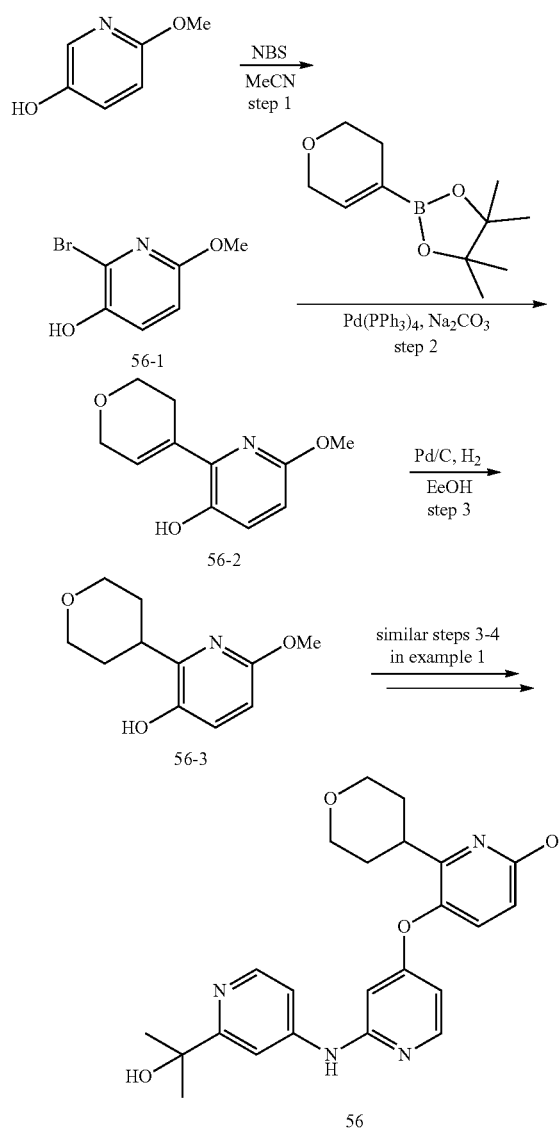

Step 1: To a solution of 5-hydroxy-2-methoxylpyridine (500 mg, 4.00 mmol) in acetonitrile (20 mL) was added N-bromosuccinimide (783 mg, 4.4 mmol) at room temperature. The mixture was stirred for 20 minutes under $N_2$ atmosphere, followed by quenching with water. The solution was extracted with ethyl acetate. The combined organic layer was washed with brine, dried over sodium sulfate, filtered and concentrated to give 56-1 which was used in next step without further purification.

Step 2: To a mixture of 56-1 (610 mg, 3.0 mmol) and 3,6-dihydro-2H-pyran-4-boronic acid pinacol ester (757 mg, 3.6 mmol) in 1,4-dioxane (20 mL) was added a solution of sodium carbonate (795 mg, 7.5 mmol) in water (5 mL) at room temperature. To above mixture was added tetrakis-(triphenylphosphine)palladium (173 mg, 0.15 mmol), and the mixture was heated at 90° C. for 3 hours under $N_2$ atmosphere. After the solvent was removed, and the residue was dissolved in ethyl acetate and washed with water and brine, dried over sodium sulfate, filtered and concentrated. The residue was purified by column chromatography on silica gel (petroleum ether to EtOAc/petroleum ether=1/1) to give 56-2.

Step 3: To a solution of 56-2 (400 mg, 1.93 mmol) in ethanol (40 mL) was added 5% Pd/C (400 mg). The mixture was stirred at room temperature for overnight under $H_2$ atmosphere. After filtration, the filtrate was concentrated to afford 56-3.

Followed the similar steps in example 1 to synthesize 56. LCMS (ES, m/z): $[M+H]^+$=437.5; HNMR (400 MHz, DMSO-$d_6$, ppm): δ 9.39 (s, 1H), 8.16 (d, J=5.6 Hz, 1H), 8.12 (d, J=6.0 Hz, 1H), 7.65-7.64 (m, 2H), 7.53 (d, J=8.8 Hz, 1H), 6.76 (d, J=8.4 Hz, 1H), 6.55 (dd, J=5.6, 2.0 Hz, 1H), 6.15 (d, J=2.0 Hz, 1H), 5.07 (s, 1H), 3.87-3.84 (m, 5H), 3.27-3.25 (m, 2H), 2.99-2.92 (m, 1H), 1.93-1.82 (m, 2H), 1.50-1.47 (m, 2H), 1.36 (s, 6H).

Example 12 Synthesis of Compound 60

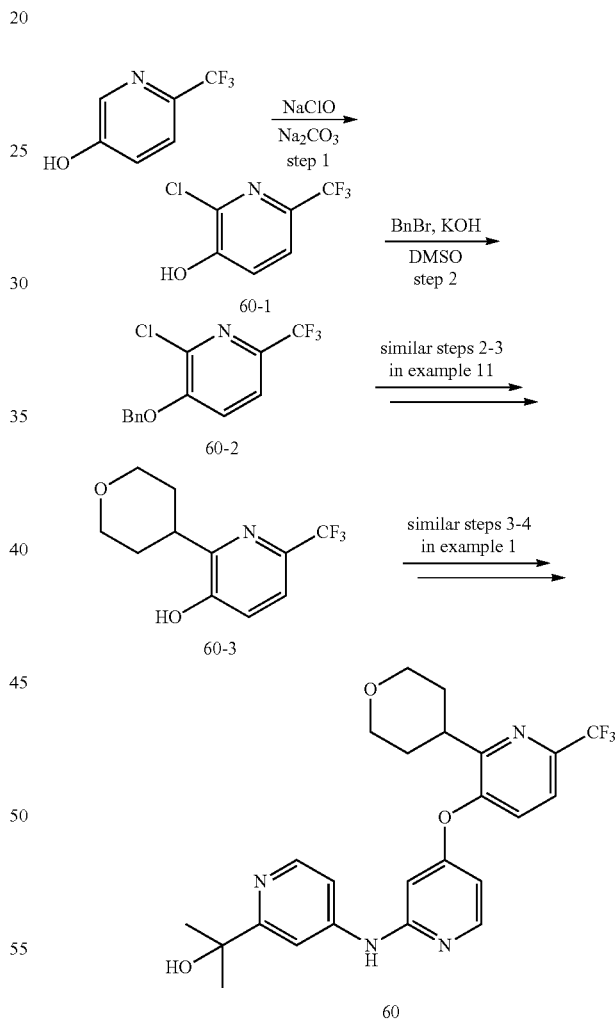

Step 1: To a solution of 6-(trifluoromethyl)pyridine-3-ol (2.00 g, 12.26 mmol) and $Na_2CO_3$ (1.36 g, 12.83 mmol) in water (60 mL) was added an aqueous NaClO solution (0.7 N, 18.0 mL, 12.60 mmol) portion wise at 0° C., and the mixture was stirred at 0° C. for 2 hours. The mixture was neutralized with acetic acid and extracted with EtOAc. The combined organic layer was washed with brine, dried over anhydrous $Na_2SO_4$, filtered and concentrated. The residue was purified by reverse phase flash column (MeCN with 0.1% of aqueous formic acid, 10% to 50%) to afford 60-1.

Step 2: A mixture of 60-1 (900 mg, 4.56 mmol) and KOH (1.02 g, 18.18 mmol) in DMSO (10 mL) was stirred at room temperature for 15 minutes. To the above mixture was added benzyl bromide (935 mg, 5.47 mmol) dropwise at room temperature, and the mixture was stirred for 2 hours. The mixture was diluted with water and extracted with EtOAc. The combined organic layer was washed with brine, dried over anhydrous Na$_2$SO$_4$, filtered and concentrated. The residue was purified by silica gel column chromatography (petroleum ether/EtOAc=20/1) to 60-2.

Followed the similar steps in example 11 to synthesize 60-3.

Followed the similar steps in example 1 to synthesize 60. LCMS (ES, m/z): [M+H]$^+$=475.3; HNMR (400 MHz, DMSO-d$_6$, ppm): δ 9.49 (s, 1H), 8.25 (d, J=5.6 Hz, 1H), 8.23 (d, J=4.8 Hz, 1H), 7.96-7.86 (m, 2H), 7.71-7.69 (m, 2H), 6.70 (dd, J=6.0, 2.4 Hz, 1H), 6.35 (d, J=2.4 Hz, 1H), 5.11 (s, 1H), 3.95-3.91 (m, 2H), 3.43-3.37 (m, 2H), 3.30-3.23 (m, 1H), 1.93-1.82 (m, 2H), 1.72-1.60 (m, 2H), 1.41 (s, 6H).

Example 13 Synthesis of Compound 61

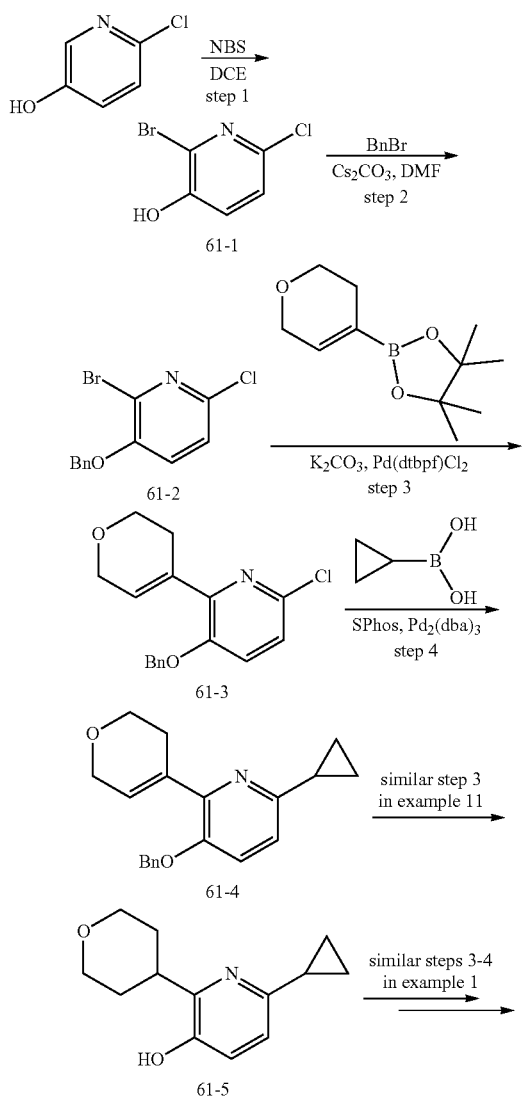

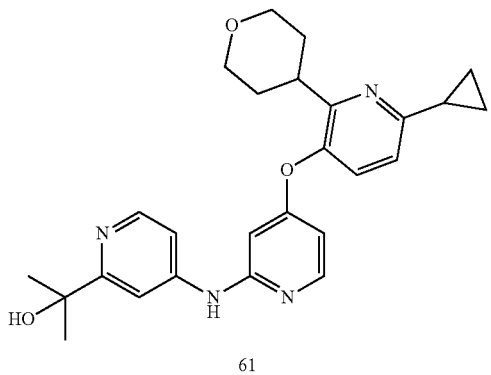

61

Step 1: A solution of 6-chloropyridin-3-ol (5.00 g, 38.60 mmol) and NBS (7.21 g, 40.51 mmol) in DCE (50 mL) was stirred at 0° C. for 2 hours. The resulting mixture was diluted with water and extracted with EtOAc. The combined organic layer was washed with brine, dried over anhydrous Na$_2$SO$_4$, filtered and concentrated. The residue was purified by reverse phase flash column (0.1% aqueous formic acid/ACN) to afford 61-1.

Step 2: A solution of 61-1 (3.40 g, 16.31 mmol), BnBr (3.35 g, 19.59 mmol) and Cs$_2$CO$_3$ (7.97 g, 24.46 mmol) in DMF (40 mL) was heated at 80° C. for 3 hours. The resulting mixture was cooled, diluted with water and extracted with EtOAc. The combined organic layer was washed with brine, dried over anhydrous Na$_2$SO$_4$, filtered and concentrated. The residue was purified by column chromatography on silica gel (petroleum ether/EtOAc=3/1) to afford 61-2.

Step 3: A solution of 61-2 (4.15 g, 13.90 mmol), 3,6-dihydro-2H-pyran-4-boronic acid pinacol ester (2.77 g, 13.19 mmol), K$_2$CO$_3$ (5.76 g, 41.68 mmol) and Pd(dtbpf)Cl$_2$ (0.45 g, 0.69 mmol) in THF (50 mL) was heated at 50° C. for 2 hours. The resulting mixture was concentrated, and the residue was diluted with water and extracted with EtOAc. The combined organic layer was washed with brine, dried over anhydrous Na$_2$SO$_4$, filtered and concentrated. The residue was purified by column chromatography on silica gel (petroleum ether/EtOAc=10/1) to afford 61-3.

Step 4: A solution of 61-3 (1.00 g, 3.31 mmol), cyclopropylboronic acid (0.43 g, 5.00 mmol), Pd$_2$(dba)$_3$ (0.30 g, 0.33 mmol), SPhos (0.27 g, 0.66 mmol) and Na$_2$CO$_3$ (0.53 g, 5.00 mmol) in toluene/H$_2$O (5:1, 12 mL) was heated at 80° C. under nitrogen atmosphere for overnight. The resulting mixture was cooled, diluted with water and extracted with EtOAc. The combined organic layer was washed with brine, dried over anhydrous Na$_2$SO$_4$, filtered and concentrated. The residue was purified by a prep-TLC (petroleum ether/EtOAc=4/1) to afford 61-4.

Followed the similar step in example 11 to synthesize 61-5.

Followed the similar steps in example 1 to synthesize 61. LCMS (ES, m/z): [M+H]$^+$=447.3; HNMR (300 MHz, DMSO-d$_6$, ppm): δ 9.44 (s, 1H), 8.20 (d, J=6.3 Hz, 1H), 8.17 (d, J=6.0 Hz, 1H), 7.69-7.67 (m, 2H), 7.46 (d, J=8.1 Hz, 1H), 7.28 (d, J=8.4 Hz, 1H), 6.60 (dd, J=5.7, 2.1 Hz, 1H), 6.18 (d, J=2.4 Hz, 1H), 5.09 (s, 1H), 3.91-3.84 (m, 2H), 3.36-3.26 (m, 2H), 3.05-2.97 (m, 1H), 2.18-2.14 (m, 1H), 1.91-1.77 (m, 2H), 1.55-1.47 (m, 2H), 1.40 (s, 6H), 1.02-0.92 (m, 4H).

Example 14 Synthesis of Compound 64

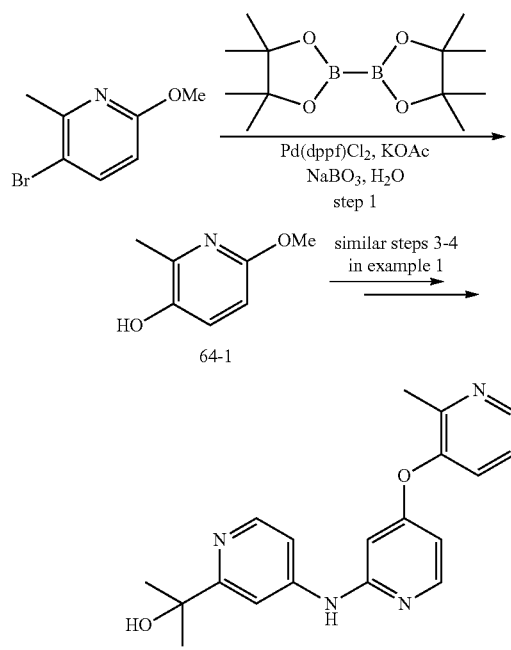

Step 1: To a solution of 3-bromo-6-methoxy-2-methylpyridine (4.0 g, 19.80 mmol) in dioxane (100 mL) was added potassium acetate (3.96 g, 40.35 mmol), bis(pinacolato)diboron (7.62 g, 30.00 mmol) and Pd(dppf)Cl$_2$ dichloromethane complex (816 mg, 1.00 mmol) under N$_2$ atmosphere, and the mixture was heated at 100° C. for 16 hours. After the reaction mixture was cooled to room temperature, a solution of sodium perborate (3.28 g, 40.10 mmol) in water (20 mL) was added. The mixture was stirred for another 2 hours at room temperature, diluted with water and extracted with ethyl acetate. The combined organic layer was dried over sodium sulfate, filtrated and concentrated. The residue was purified by column chromatography on silica gel (petroleum ether to petroleum ether/ethyl acetate=4/1) to give 64-1.

Followed the similar steps in example 1 to synthesize 64. LCMS (ES, m/z): [M+H]$^+$=367.1; HNMR (400 MHz, CD$_3$OD, ppm): δ 8.15 (d, J=6.0 Hz, 1H), 8.11 (d, J=6.0 Hz, 1H), 7.78-7.76 (m, 1H), 7.56 (dd, J=5.6, 2.0 Hz, 1H), 7.39 (d, J=8.4 Hz, 1H), 6.69 (d, J=8.8 Hz, 1H), 6.48 (dd, J=6.0, 2.0 Hz, 1H), 6.21 (d, J=2.0 Hz, 1H), 3.89 (s, 3H), 2.26 (s, 3H), 1.49 (s, 6H).

Example 15 Synthesis of Compound 65

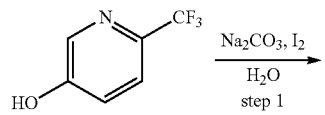

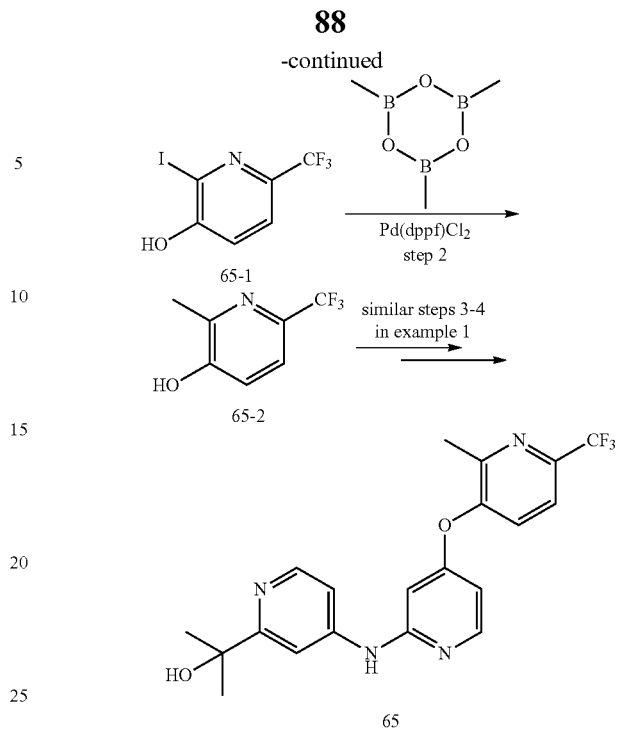

Step 1: To a mixture of sodium carbonate (1.40 g, 13.21 mmol) and 6-(trifluoromethyl)pyridin-3-ol (0.98 g, 6.01 mmol) in water (20 mL) was added iodine (1.54 g, 6.07 mmol), and the reaction mixture was stirred at room temperature overnight. The reaction was neutralized to pH 6 with 1M HCl and then extracted with ethyl acetate. The combined organic layer was washed with brine, dried over sodium sulfate, filtered and concentrated. The residue was purified by column chromatography on silica gel (petroleum ether to ethyl acetate/petroleum ether=1/3) to give 65-1.

Step 2: To a mixture of 65-1 (620 mg, 2.15 mmol) and trimethylboroxine (2.2 mL, 3.5M in THF, 7.7 mmol) in 1,4-dioxane (16 mL) was added potassium carbonate (890 mg, 6.44 mmol) and Pd(dppf)Cl$_2$ (174 mg, 0.21 mmol) at room temperature, the mixture was heated at 90° C. for 25 minutes under microwave. After cooling to room temperature, the reaction was neutralized to pH 6 with 1M HCl and extracted with ethyl acetate. The combined organic layer was washed with brine, dried over sodium sulfate, filtered and concentrated. The residue was purified by column chromatography on silica gel (petroleum ether to ethyl acetate/petroleum ether=1/3) to afford 65-2.

Followed the similar steps in example 1 to synthesize 65. LCMS (ES, m/z): [M+H]$^+$=405.0; HNMR (400 MHz, DMSO-d$_6$, ppm): δ 9.46 (s, 1H), 8.20-8.17 (m, 2H), 7.87-7.83 (m, 2H), 7.66-7.64 (m, 2H), 6.62 (dd, J=6.0, 2.4 Hz, 1H), 6.28 (d, J=2.4 Hz, 1H), 5.09 (s, 1H), 2.42 (s, 3H), 1.37 (s, 6H).

Example 16 Synthesis of Compound 66

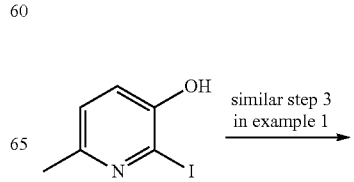

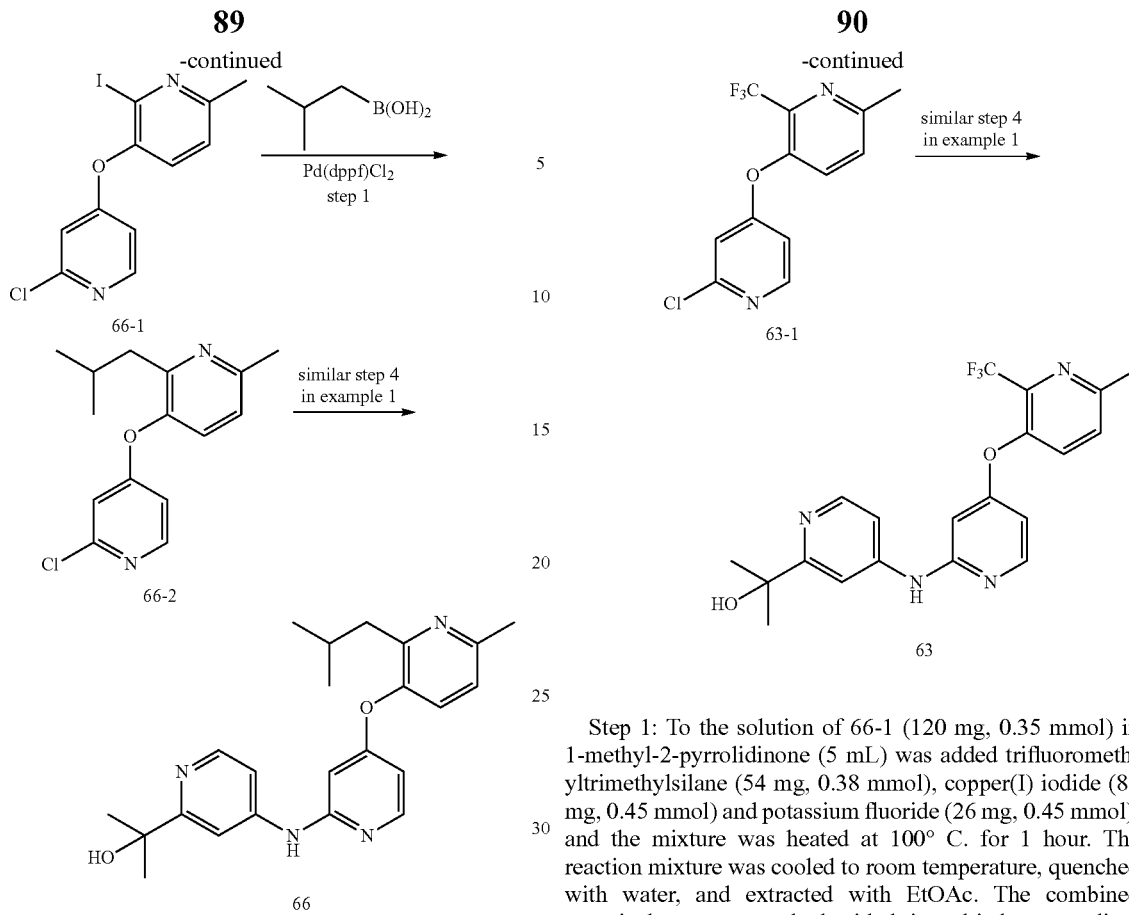

Followed the similar step in example 1 to synthesize 66-1.

Step 1: To a mixture of 66-1 (200 mg, 0.56 mmol), isobutylboronic acid (71 mg, 0.70 mmol), potassium carbonate (240 mg, 1.74 mmol) and Ag$_2$O (336 mg, 1.45 mmol) in THF (10 mL) was added Pd(dppf)Cl2 (49 mg, 0.06 mmol). The reaction mixture was refluxed for 4 hours under N$_2$ atmosphere, cooled to room temperature and filtered. The filtrate was concentrated to give a residue which was purified by column chromatography on silica gel (petroleum ether to ethyl acetate/petroleum ether=1/3) to afford 66-2.

Followed the similar step in example 1 to synthesize 66. LCMS (ES, m/z): [M+H]$^+$=393.1; HNMR (400 MHz, CD$_3$OD, ppm): δ 8.17-8.14 (m, 2H), 7.79 (d, J=2.0 Hz, 1H), 7.58 (dd, J=6.0, 2.0 Hz, 1H), 7.44 (d, J=8.4 Hz, 1H), 7.21 (d, J=8.4 Hz, 1H), 6.50 (d, J=6.0, 2.0 Hz, 1H), 6.27 (d, J=2.4 Hz, 1H), 2.57 (d, J=7.2 Hz, 2H), 2.53 (s, 3H), 2.09-1.99 (m, 1H), 1.50 (s, 6H), 0.88 (d, J=7.2 Hz, 6H).

Example 17 Synthesis of Compound 63

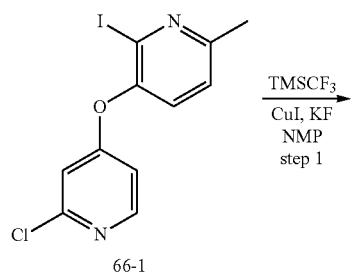

Step 1: To the solution of 66-1 (120 mg, 0.35 mmol) in 1-methyl-2-pyrrolidinone (5 mL) was added trifluoromethyltrimethylsilane (54 mg, 0.38 mmol), copper(I) iodide (85 mg, 0.45 mmol) and potassium fluoride (26 mg, 0.45 mmol), and the mixture was heated at 100° C. for 1 hour. The reaction mixture was cooled to room temperature, quenched with water, and extracted with EtOAc. The combined organic layer was washed with brine, dried over sodium sulfate, filtered and concentrated. The residue was purified by column chromatography on silica gel (petroleum ether/EtOAc=4/1 to 1/1) to afford 63-1.

Followed the similar step in example 1 to synthesize 63. LCMS (ES, m/z): [M+H]$^+$=405.1; HNMR (400 MHz, DMSO-d$_6$, ppm): δ 9.43 (s, 1H), 8.19-8.16 (m, 2H), 7.87 (d, J=8.8 Hz, 1H), 7.71 (d, J=8.8 Hz, 1H), 7.65-7.63 (m, 2H), 6.58 (dd, J=5.6, 2.0 Hz, 1H), 6.28 (d, J=2.0 Hz, 1H), 5.07 (s, 1H), 2.56 (s, 3H), 1.36 (s, 6H).

Example 18 Synthesis of Compound 73

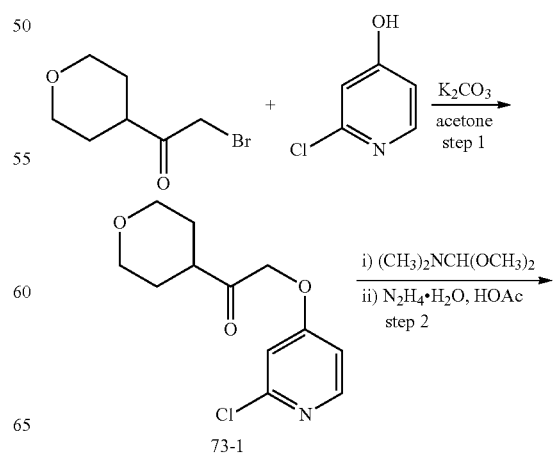

-continued

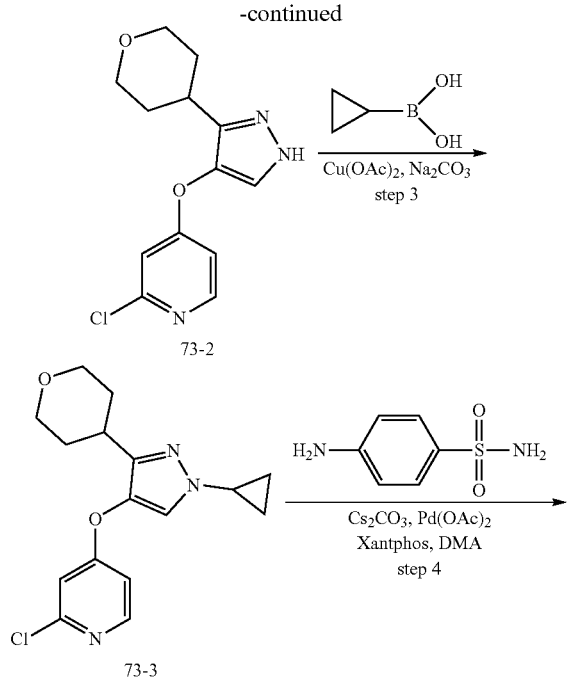

and then cooled to room temperature. To the mixture was added 73-2 (300 mg, 1.07 mmol), cyclopropylboronic acid (230 mg, 2.68 mmol) and Na₂CO₃ (284 mg, 2.68 mmol), and the mixture was heated at 75° C. overnight. The mixture was cooled and filtered. The filter cake was washed with EtOAc, and the combined filtrate was concentrated. The residue was purified by a prep-TLC (petroleum ether/EtOAc=1/1) to afford 73-3.

Step 4: A solution of 73-3 (200 mg, 0.63 mmol), sulfanilamide (140 mg, 0.81 mmol), Cs₂CO₃ (304 mg, 0.93 mmol), Pd(OAc)₂ (14 mg, 0.06 mmol) and Xantphos (72 mg, 0.12 mmol) in DMAc (3 mL) was stirred at room temperature for 0.5 hour under nitrogen atmosphere. The reaction mixture was then irradiated with microwave for 30 min at 150° C. The crude product was purified by a prep-HPLC (MeCN/aqueous NH₄HCO₃ (10 mmol/L), 37 to 43%) to afford 73. LCMS (ES, m/z): [M+H]⁺=456.3; HNMR (300 MHz, DMSO-d₆, ppm): δ 9.46 (s, 1H), 8.11 (d, J=5.7 Hz, 1H), 7.88 (s, 1H), 7.81 (d, J=8.7 Hz, 2H), 7.68 (d, J=8.7 Hz, 2H), 7.13 (s, 2H), 6.57 (dd, J=6.0, 2.1 Hz, 1H), 6.34 (d, J=2.1 Hz, 1H), 3.85-3.81 (m, 2H), 3.70-3.65 (m, 1H), 2.74-2.70 (m, 1H), 1.69-1.63 (m, 4H), 1.08-1.01 (m, 4H).

Example 19 Synthesis of Compound 70

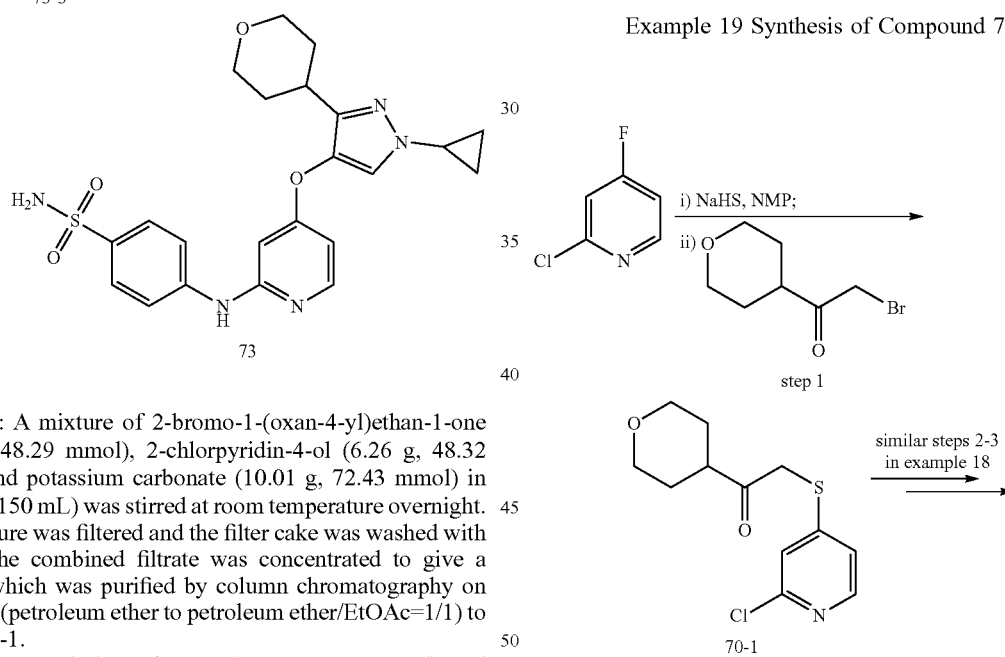

Step 1: A mixture of 2-bromo-1-(oxan-4-yl)ethan-1-one (10.0 g, 48.29 mmol), 2-chlorpyridin-4-ol (6.26 g, 48.32 mmol) and potassium carbonate (10.01 g, 72.43 mmol) in acetone (150 mL) was stirred at room temperature overnight. The mixture was filtered and the filter cake was washed with DCM. The combined filtrate was concentrated to give a residue which was purified by column chromatography on silica gel (petroleum ether to petroleum ether/EtOAc=1/1) to afford 73-1.

Step 2: A solution of 73-1 (9.9 g, 38.72 mmol) and N,N-dimethylformamide dimethylacetal (20 mL) was heated at 100° C. for 2 hours. The mixture was cooled to room temperature, diluted with water and extracted with EtOAc. The combined organic layer was washed with brine, dried over sodium sulfate, filtered and concentrated to give a brown solid. The brown solid was dissolved in HOAc (100 mL), and N₂H₄H₂O (5.65 mL) was added at 0° C. The mixture was stirred at room temperature overnight, and then poured into ice-water and extracted with EtOAc. The combined organic layer was washed with brine, dried over sodium sulfate, filtered and concentrated. The residue was purified by column chromatography on silica gel (petroleum ether to petroleum ether/EtOAc=1/1) to afford 73-2.

Step 3: To a solution of Cu(OAc)₂ (214 mg, 1.18 mmol) in DCE (6 mL) was added 2,2'-bipyridine (156 mg, 1.00 mmol), and the mixture was heated at 75° C. for 25 minutes

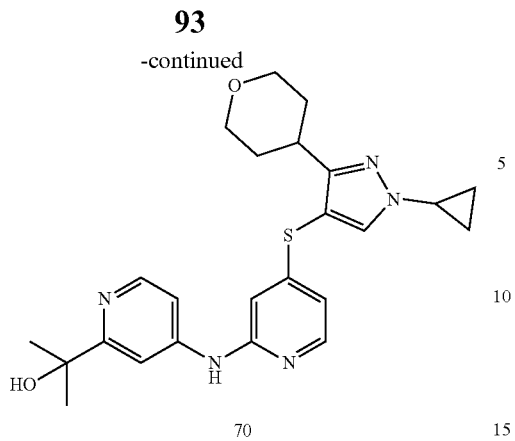

Step 1: To a solution of sodium hydrosulfide (1.28 g, 22.83 mmol) in NMP (40 mL) was added a solution of 2-chloro-4-fluoropyridine (2.00 g, 15.21 mmol) in NMP (10 mL) drop wise, and the mixture was stirred at room temperature for 2 hours. Then NMP (10 mL), DIEA (4.50 mL, 27.23 mmol) and 2-bromo-1-(oxan-4-yl)ethan-1-one (4.27 g, 20.63 mmol) were added. The resulting mixture was stirred at room temperature for 2 hours, followed by quenching with water. The solution was extracted with ethyl acetate, and the combined organic layer was washed with brine, dried over sodium sulfate, filtered and concentrated.

The residue was purified by column chromatography on silica gel to afford 70-1.

Followed the similar steps in example 18 to synthesize 70-2.

Followed the similar step in example 1 to synthesize 70. LCMS (ES, m/z): [M+H]$^+$=452.3; HNMR (400 MHz, DMSO-d$_6$, ppm): 9.48 (s, 1H), 8.19 (d, J=6.0 Hz, 1H), 8.12 (s, 1H), 8.04 (d, J=5.6 Hz, 1H), 7.73 (dd, J=5.6, 2.0 Hz, 1H), 7.67 (d, J=2.0 Hz, 1H), 6.60 (dd, J=5.6, 1.2 Hz, 1H), 6.39 (d, J=1.2 Hz, 1H), 3.89-3.80 (m, 2H), 3.78-3.70 (m, 1H), 3.34-3.29 (m, 2H), 2.90-2.80 (m, 1H), 1.81-1.68 (m, 2H), 1.68-1.60 (m, 2H), 1.40 (s, 6H), 1.11-1.09 (m, 2H), 1.01-0.95 (m, 2H).

Example 20 Synthesis of Compound 71

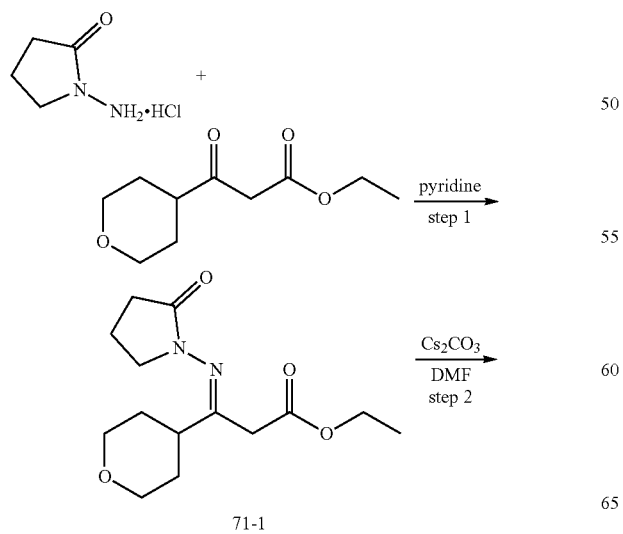

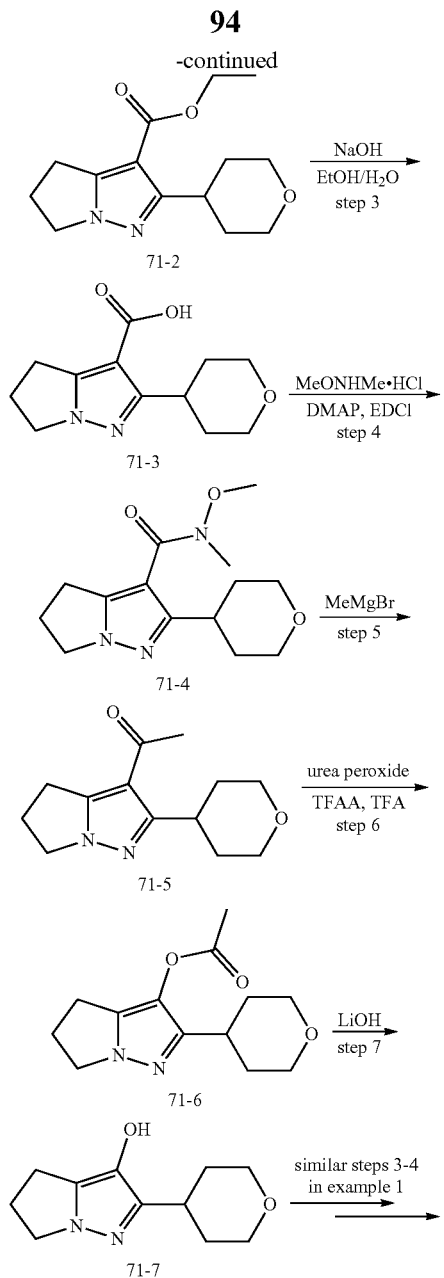

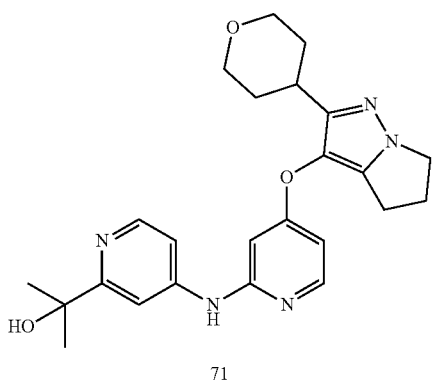

Step 1: A mixture of 1-aminopyrrolidin-2-one hydrochloride (2.0 g, 14.64 mmol) and ethyl 3-(oxan-4-yl)-3-oxopropanoate (3.52 g, 17.58 mmol) in pyridine (60 mL) was heated at 50° C. overnight under nitrogen atmosphere. The mixture was concentrated to give a residue which was purified by column chromatography on silica gel (DCM/MeOH=50/1) to afford 71-1.

Step 2: A mixture of 71-1 (2.0 g, 7.08 mmol) and Cs$_2$CO$_3$ (4.63 g, 14.21 mmol) in DMF (150 mL) was heated at 100° C. overnight under nitrogen atmosphere. The reaction was quenched with water and extracted with EtOAc. The combined organic layer was washed with brine, dried over anhydrous Na$_2$SO$_4$, filtered and concentrated. The residue was purified by column chromatography on silica gel (petroleum ether/EtOAc=7/1) to afford 71-2.

Step 3: To a stirred solution of 71-2 (1.0 g, 3.78 mmol) in EtOH (5 mL) and H$_2$O (10 mL) was added NaOH (0.98 g, 24.50 mmol) in portions at room temperature. The resulting mixture was heated at 100° C. for 2 hours. The mixture was concentrated, and the residue was neutralized to pH 5 to 7 with hydrogen chloride. Filtered and the filter cake was dried to afford 71-3.

Step 4: A mixture of 71-3 (350 mg, 1.48 mmol), methoxy(methyl)amine hydrochloride (217 mg, 2.22 mmol), DMAP (217 mg, 1.78 mmol) and EDCI (341 mg, 1.78 mmol) in DCM (10 mL) was stirred at room temperature for 4 hours under nitrogen atmosphere. The mixture was concentrated, and the residue was purified by a prep-TLC (EtOAc) to afford 71-4.

Step 5: To a stirred solution of 71-4 (153 mg, 0.55 mmol) in THF (4 mL) was added methyl magnesium bromide (1.65 mL, 1 M) drop wise at −78° C. under nitrogen atmosphere, and the mixture was stirred at room temperature overnight, followed by quenching with aqueous NH$_4$Cl at 0° C. The resulting mixture was extracted with EtOAc, and the combined organic layer was dried over anhydrous Na$_2$SO$_4$, filtered and concentrated. The residue was purified by a prep-TLC (EtOAc) to afford 71-5.

Step 6: To a stirred solution of urea peroxide (193 mg, 2.05 mmol) in CF$_3$COOH (4 mL) was added trifluoroacetic anhydride (242 mg, 1.15 mmol) drop wise at 0° C. under nitrogen atmosphere, and the mixture was stirred at 0° C. for 30 minutes. A solution of 71-5 (60 mg, 0.26 mmol) in CF$_3$COOH (2 mL) was added and the mixture was stirred at room temperature overnight. The mixture was concentrated under reduced pressure, followed by quenching with NaHSO$_3$. The mixture was diluted with a saturated aqueous NaHCO$_3$ solution and extracted with CH$_2$Cl$_2$. The combined organic layer was concentrated to afford 71-6.

Step 7: To a stirred solution of 71-6 (40 mg, 0.16 mmol) in MeOH (1 mL) was added a solution of lithium hydroxide (12 mg, 0.50 mmol) in H$_2$O (0.2 mL) in portions at room temperature, and the resulting mixture was stirred at room temperature for 2 hours under nitrogen atmosphere. The mixture was extracted with EtOAc, and the combined organic layer was washed with brine, dried over anhydrous Na$_2$SO$_4$, filtered and concentrated. The residue was purified by a prep-TLC (EtOAc) to afford 71-7.

Followed the similar steps in example 1 to synthesize 71. LCMS (ES, m/z): [M+H]$^+$=436.3; HNMR (400 MHz, DMSO-d$_6$, ppm): δ 9.49 (s, 1H), 8.21 (d, J=5.6 Hz, 1H), 8.14 (d, J=6.0 Hz, 1H), 7.76-7.64 (m, 2H), 6.59 (dd, J=6.0, 2.0 Hz, 1H), 6.39 (d, J=2.0 Hz, 1H), 5.13 (s, 1H), 4.07 (t, J=7.2 Hz, 2H), 3.85-3.82 (m, 2H), 3.38-3.26 (m, 2H), 2.78-2.64 (m, 3H), 2.50-2.60 (m, 1H), 1.62-1.72 (m, 4H), 1.40 (s, 6H), 1.30-1.21 (s, 1H).

Example 21 Synthesis of Compound 72

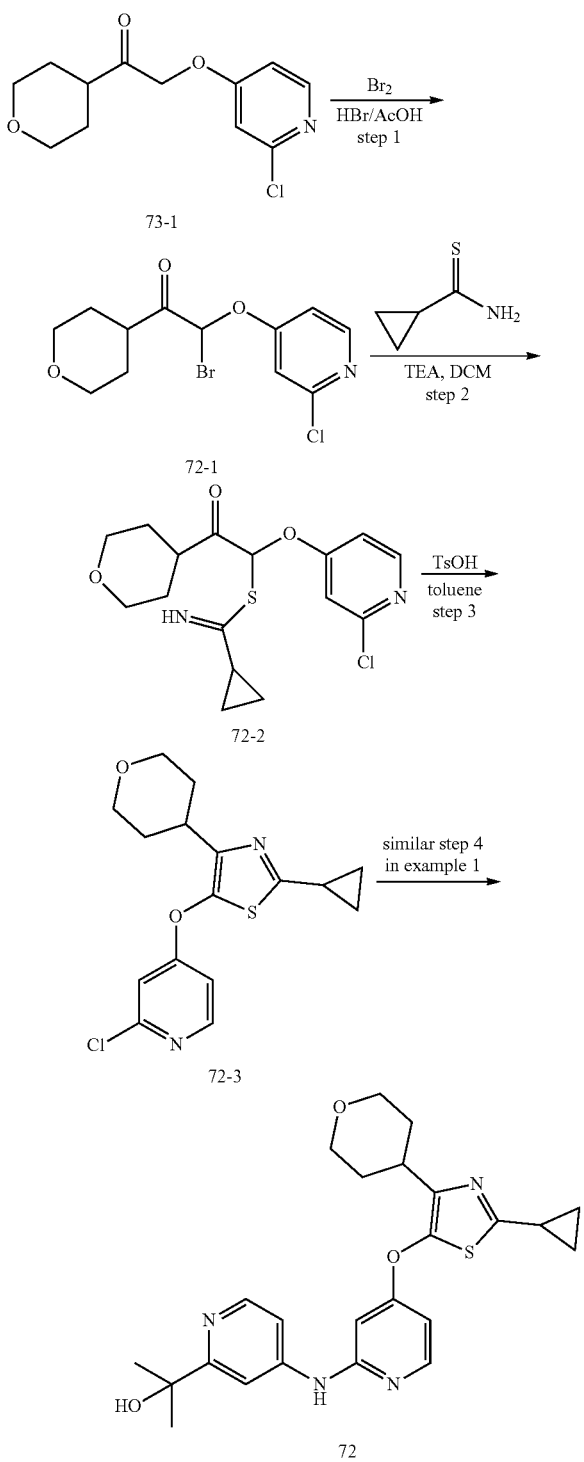

Step 1: To a solution of 73-1 (2.5 g, 9.78 mmol) in chloroform (35 mL) and HBr (33% in HOAc, 10 mL) was added dropwise a solution of Br$_2$ (1.6 g, 10.01 mmol) in HOAc (5 mL) at 0° C., and the mixture was stirred at 0° C. for 30 minutes, followed by quenching with H$_2$O. The mixture was extracted with dichloromethane, and the organic layer was washed with saturated aqueous sodium bicarbonate and brine, dried over sodium sulfate, filtered and concentrated below 10° C. to give a crude 72-1.

Step 2: To a solution of 72-1 (2.1 g, 6.28 mmol) and cyclopropanecarbothioamide (700 mg, 6.92 mmol) in dichloromethane (60 mL) was added trimethylamine (1.6 g, 15.81 mmol) at 0° C., and the mixture was stirred at room temperature for 1 hour. The reaction solution was concentrated below 10° C., and the residue was purified by column chromatography on silica gel (petroleum ether to ethyl acetate/petroleum ether=1/1) to afford 72-2.

Step 3: To a solution of 72-2 (1.0 g, 2.82 mmol) in dry toluene (15 mL) was added p-TSA (17 mg, 0.1 mmol), and the mixture was heated at 120° C. for 2 hours under $N_2$ atmosphere. After cooling to room temperature, the mixture was quenched with water and extracted with ethyl acetate. The combined organic layer was washed with brine, dried over sodium sulfate, filtered and concentrated. The residue was purified by column chromatography on silica gel (petroleum ether to ethyl acetate/petroleum ether=1/1) to give 72-3.

Followed the similar step in example 1 to synthesize 72. LCMS (ES, m/z): [M+H]$^+$=453.4; HNMR (400 MHz, CD$_3$OD, ppm): δ 8.20-8.17 (m, 2H), 7.86 (s, 1H), 7.66 (d, J=4.8 Hz, 1H), 6.65 (dd, J=6.0, 2.0 Hz, 1H), 6.46 (d, J=2.0 Hz, 1H), 3.95-3.92 (m, 2H), 3.44-3.38 (m, 2H), 2.88-2.82 (m, 1H), 2.28-2.40 (m, 1H), 1.99-1.88 (m, 2H), 1.62-1.58 (m, 2H), 1.52 (s, 6H), 1.13-1.10 (m, 2H), 0.99-0.97 (m, 2H).

Example 22 Synthesis of Compound 74

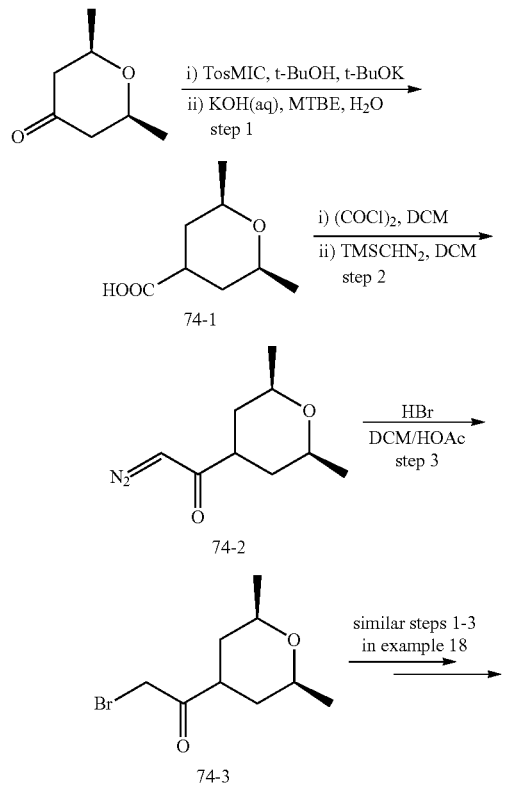

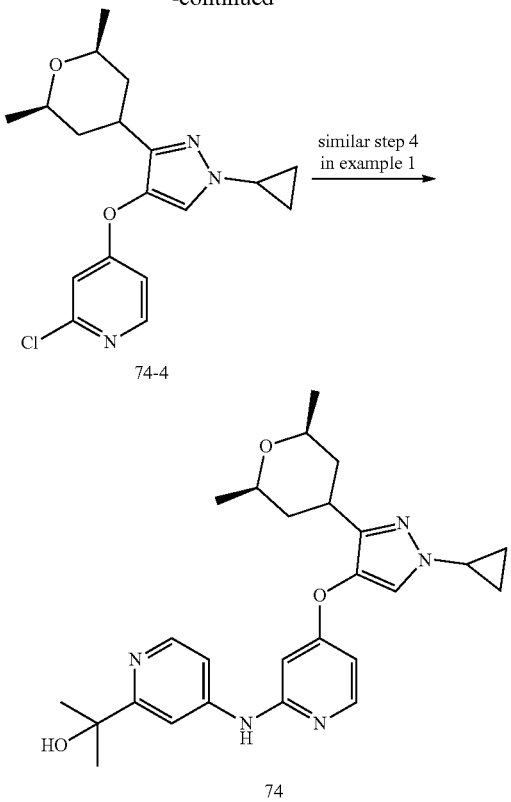

Step 1: To a solution of cis-2,6-dimethyloxan-4-one (2.00 g, 15.60 mmol), TosMIC (3.96 g, 20.28 mmol) and t-BuOH (1.97 g, 26.58 mmol) in DME (30 mL) was added t-BuOK (4.38 g, 39.03 mmol) at 0° C., and the mixture was stirred at 35° C. for 18 hours. The mixture was filtered and the filter cake was washed with MTBE. To the combined filtrate was added a solution of KOH (13.13 g, 234.00 mmol) in water (50 mL), and the resulting solution was heated at 80° C. for 48 hours. The mixture was cooled to room temperature, diluted with MTBE, and filtered. The filtrate was concentrated to afford 74-1.

Step 2: To a solution of 74-1 (700 mg, 4.42 mmol) in DCM (10 mL) was added oxalyl chloride (730 mg, 5.75 mmol) and DMF (2 drops) at 0° C., and the mixture was stirred at room temperature for 3 hours. After concentration, the mixture was diluted with DCM (10 mL), and TMSCHN$_2$ (9 mL, 2 M in hexane) was added at −10° C. The resulting solution was stirred at room temperature for 16 hours, followed by quenching with HOAc. The resulting mixture was concentrated, and the residue was purified by column chromatography on silica gel to afford 74-2.

Step 3: To a mixture of 74-2 (400 mg, 2.20 mmol) in DCM (9 mL) and HOAc (1 mL) was added aqueous hydrogen bromide (48%, 710 mg, 4.21 mmol) dropwise at −10° C., and the resulting solution was stirred at room temperature for 3 hours, followed by quenching with ice-water. The mixture was extracted with DCM, and the combined organic layer was washed with saturated aqueous Na$_2$CO$_3$ and brine, dried over anhydrous sodium sulfate, filtered and concentrated to afford 74-3.

Followed the similar steps in example 18 and example 1 to synthesize 74. LCMS (ES, m/z): [M+H]$^+$=464.4; HNMR (300 MHz, DMSO-d$_6$, ppm): δ 9.50 (s, 1H), 8.21 (d, J=6.3 Hz, 1H), 8.14 (d, J=6.0 Hz, 1H), 7.86 (s, 1H), 7.71-7.62 (m, 2H), 6.58 (dd, J=6.0, 2.4 Hz, 1H), 6.38 (d, J=2.4 Hz, 1H), 5.12 (s, 1H), 3.72-3.60 (m, 1H), 3.49-3.41 (m, 2H), 2.81-2.69 (m, 1H), 1.75-1.69 (m, 2H), 1.40 (s, 6H), 1.24 (q, J=12.3 Hz, 2H), 1.01-1.07 (m, 8H), 0.91-0.98 (m, 2H).

Example 23 Synthesis of Compound 75

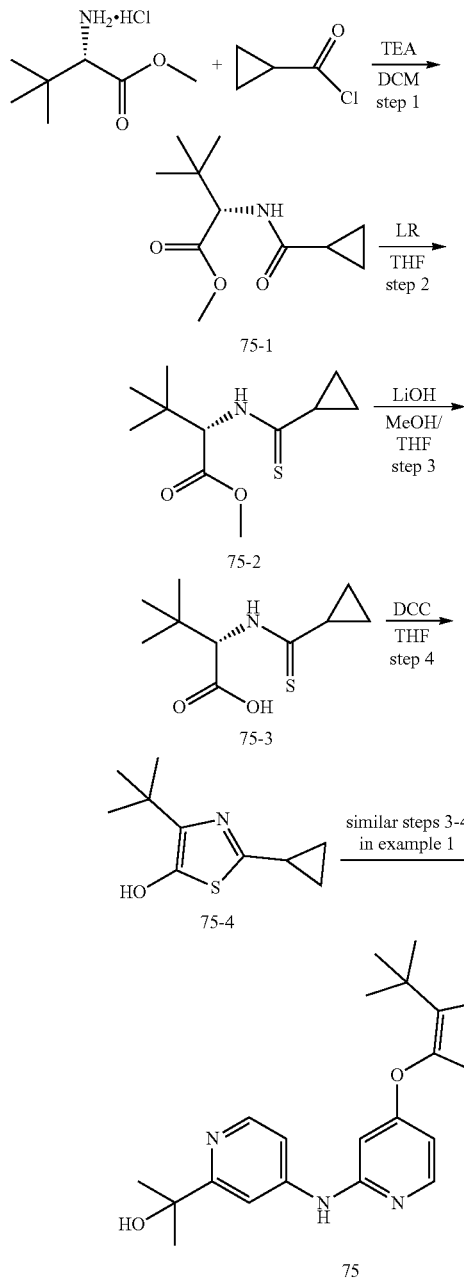

Step 1: To a suspension of methyl (S)-2-amino-3,3-dimethylbutanoate hydrochloride (5.0 g, 27.52 mmol) in dichloromethane (150 mL) was added triethylamine (7 g, 69 mmol) and the mixture was stirred at room temperature for 30 minutes, and then cyclopropanecarbonyl chloride (3.4 g, 32.54 mmol) in dichloromethane (20 mL) was added dropwise at 0° C. The reaction mixture was stirred at room temperature for 16 hours. The mixture was washed with water, 1N hydrochloric acid and aqueous sodium bicarbonate solution, and the organic phase was concentrated to afford 75-1.

Step 2: To a solution of 75-1 (849 mg, 3.98 mmol) in tetrahydrofuran (15 mL) was added Lawesson's reagent (888 mg, 2.20 mmol), and the mixture was heated at 70° C. for 1.5 hours under $N_2$ atmosphere. The mixture was concentrated, and the residue was purified by column chromatography on silica gel (petroleum ether to ethyl acetate/petroleum ether=1/3) to afford 75-2.

Step 3: To a solution of 75-2 (500 mg, 2.18 mmol) in methanol (3 mL) and tetrahydrofuran (3 mL) was added an aqueous lithium hydroxide solution (3 mL, 1 M), and the mixture was stirred for 16 hours. Then the mixture was concentrated and extracted with tert-butyl methyl ether. The aqueous phase was neutralized to pH 4 with hydrochloric acid (1 M) and then extracted with ethyl acetate. The combined organic layer was dried over anhydrous sodium sulfate, filtered and concentrated to afford 75-3.

Step 4: To a solution of 75-3 (300 mg, 1.39 mmol) in tetrahydrofuran (15 mL) was added dicyclohexylcarbodiimide (450 mg, 2.18 mmol), and the mixture was heated at 60° C. for 1 hour under $N_2$ atmosphere. The mixture was cooled and filtered, and the filtrate was concentrated to give a residue which was purified by column chromatography on silica gel (petroleum ether to ethyl acetate/petroleum ether=1/2) to afford 75-4.

Followed the similar steps in example 1 to synthesize 75. LCMS (ES, m/z): $[M+H]^+$=425.5; HNMR (400 MHz, DMSO-$d_6$, ppm): δ 9.53 (s, 1H), 8.18 (d, J=5.6 Hz, 1H), 8.08 (d, J=5.6 Hz, 1H), 7.71 (dd, J=5.6, 2.0 Hz, 1H), 7.62 (d, J=2.0 Hz, 1H), 6.60 (dd, J=5.6, 1.6 Hz, 1H), 6.39 (d, J=1.6 Hz, 1H), 5.08 (s, 1H), 2.13-2.10 (m, 1H), 1.36 (s, 6H), 1.29 (s, 9H), 1.07-1.03 (m, 2H), 0.96-0.93 (m, 2H).

Example 24 Synthesis of Compound 80

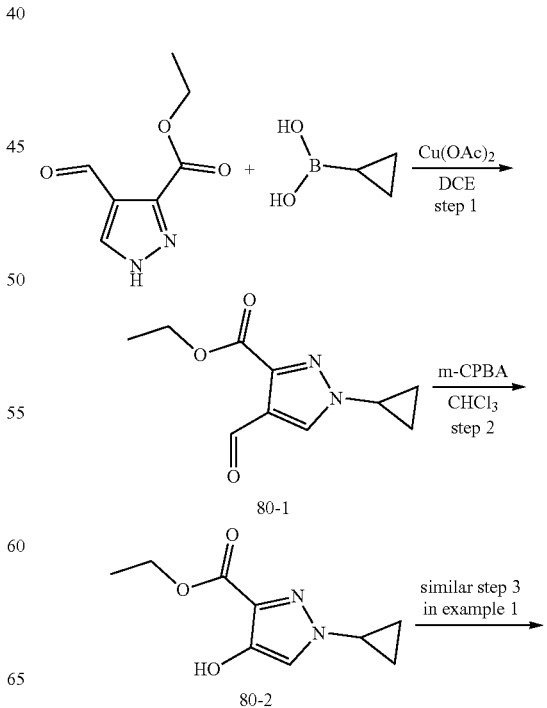

-continued

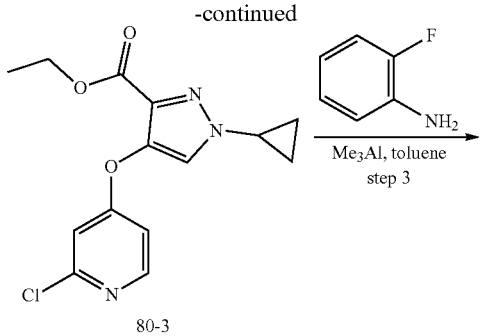

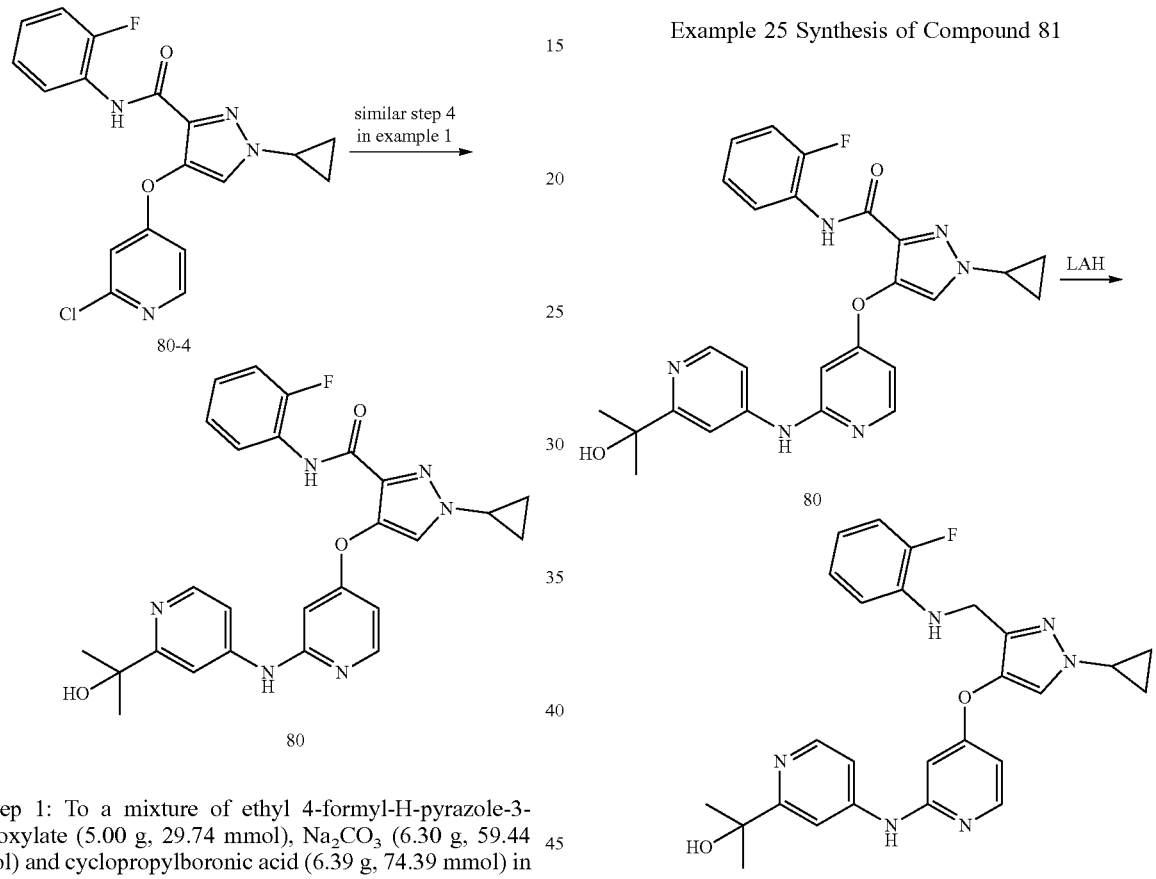

Step 1: To a mixture of ethyl 4-formyl-H-pyrazole-3-carboxylate (5.00 g, 29.74 mmol), Na$_2$CO$_3$ (6.30 g, 59.44 mmol) and cyclopropylboronic acid (6.39 g, 74.39 mmol) in DCE (160 ml) was added pyridine (11.76 g, 148.67 mmol) and Cu(OAc)$_2$ (8.10 g, 44.60 mmol), and the mixture was heated at 70° C. under air overnight. The mixture was cooled, quenched with saturated aqueous NaHCO$_3$ and extracted with EtOAc. The combined organic layer was dried over anhydrous sodium sulfate, filtered and concentrated. The residue was purified by flash chromatography on silica gel (petroleum ether/EtOAc=10/1 to 3/1) to afford 80-1.

Step 2: To a solution of 80-1 (1.20 g, 5.76 mmol) in chloroform (40.00 mL) was added m-CPBA (1.59 g, 9.21 mmol), and the mixture was stirred at room temperature overnight. The reaction mixture was quenched with aqueous NaHCO$_3$ at 0° C. and extracted with EtOAc. The combined organic layer was dried over anhydrous sodium sulfate, filtered and concentrated. The residue was purified by column chromatography on silica gel (hexane/EtOAc=2/1) to afford 80-2.

Followed the similar step in example 1 to synthesize 80-3.

Step 3: To a solution of 80-3 (500 mg, 1.62 mmol) in dry toluene (5 mL) was added 2-fluoroaniline (217 mg, 1.95 mmol) and Me$_3$Al (2 M in heptane, 1 mL), and the resulting mixture was heated at 110° C. for 1 hour. The mixture was cooled and quenched with 1 M HCl. The layers were separated and the aqueous layer was extracted with EtOAc. The combined organic layer was dried over anhydrous sodium sulfate, filtered and concentrated.

The residue was purified by a prep-TLC (petroleum ether/EtOAc=1/1) to afford 80-4. Followed the similar step in example 1 to afford 80. LCMS (ES, m/z): [M+H]$^+$=489.2; HNMR (300 MHz, DMSO-d$_6$, ppm): δ 9.57 (s, 1H), 9.43 (s, 1H), 8.22 (s, 1H), 8.19 (d, J=6.3 Hz, 2H), 8.12 (d, J=6.0 Hz, 1H), 7.75-7.65 (m, 3H), 7.29-7.11 (m, 3H), 6.56 (dd, J=6.0, 2.1 Hz, 1H), 6.37 (d, J=2.1 Hz, 1H), 5.11 (s, 1H), 3.95-3.89 (m, 1H), 1.40 (s, 6H), 1.27-1.17 (m, 4H), 1.12-1.03 (m, 2H). FNMR (282 MHz, DMSO-d$_6$, ppm): δ −124.23.

Example 25 Synthesis of Compound 81

To a solution of 80 (44 mg, 0.09 mmol) in THF (2 mL) was added LiAlH$_4$ (17 mg, 0.45 mmol) under N$_2$ atmosphere, and the mixture was heated at 40° C. for 48 hours. The reaction was quenched with saturated aqueous NH$_4$Cl at 0° C. and extracted with EtOAc. The combined organic layer was washed with brine, dried over anhydrous Na$_2$SO$_4$, filtered and concentrated. The residue was purified by a prep-HPLC (MeCN/aqueous NH$_4$HCO$_3$ (10 mmol/L), 45 to 51%) to afford 81. LCMS (ES, m/z): [M+H]*=475.3; HNMR (300 MHz, DMSO-d$_6$, ppm): δ 9.41 (s, 1H), 8.21-8.19 (m, 1H), 8.10 (d, J=6.0 Hz, 1H), 7.92 (s, 1H), 7.75-7.62 (m, 2H), 6.99-6.82 (m, 2H), 6.77-6.71 (m, 1H), 6.57-6.45 (m, 2H), 6.38 (s, 1H), 5.46 (s, 1H), 5.12 (s, 1H), 4.13 (d, J=5.7 Hz, 2H), 3.73-3.67 (m, 1H), 1.41 (s, 6H), 1.08-1.04 (s, 2H), 1.02-0.95 (m, 2H). FNMR (282 MHz, DMSO-d$_6$, ppm): δ −135.17.

Further exemplary compounds as described herein can be prepared following similar methods and techniques herein. Characterization of the compounds are provided in Table 1 below

TABLE 1

Characterization of Selected Compounds

| Compound No. | Structure | [M + H]⁺ | ¹H- and ¹⁹F-NMR |
|---|---|---|---|
| 3 | 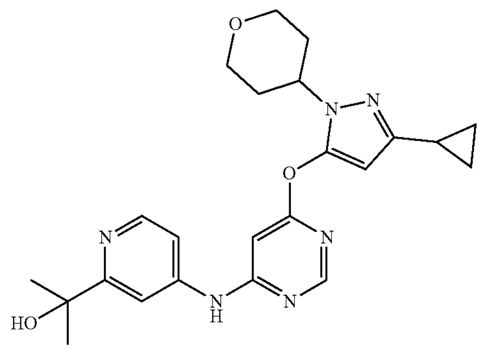 [SMILES: CC(C)(O)c1cc(Nc2cc(Oc3cc(C4CC4)nn3C3CCOCC3)ncn2)ccn1] | 437.3 | HNMR (300 MHz, DMSO-d₆, ppm): δ 10.13 (s, 1H), 8.54 (s, 1H), 8.33 (d, J = 5.7 Hz, 1H), 7.80 (d, J = 2.1 Hz, 1H), 7.70 (dd, J = 5.7, 2.1 Hz, 1H), 6.42 (s, 1H), 5.78 (s, 1H), 5.19 (s, 1H), 4.20-4.13 (m, 1H), 3.92-3.87 (m, 2H), 3.41-3.30 (m, 2H), 2.06-1.98 (m, 2H), 1.89-1.83 (m, 1H), 1.74-1.71 (m, 2H), 1.43 (s, 6H), 0.90-0.83 (m, 2H), 0.67-0.62 (m, 2H). |
| 5 | 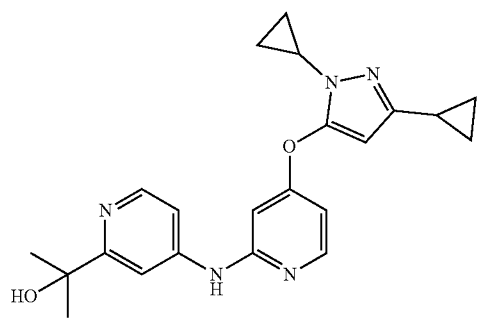 [SMILES: CC(C)(O)c1cc(Nc2cc(Oc3cc(C4CC4)nn3C3CC3)ccn2)ccn1] | 392.3 | HNMR (300 MHz, DMSO-d₆, ppm): δ 9.57 (s, 1H), 8.22 (d, J = 4.5 Hz, 2H), 7.72-7.69 (m, 2H), 6.67 (dd, J = 5.7, 2.4 Hz, 1H), 6.46 (d, J = 2.4 Hz, 1H), 5.79 (s, 1H), 5.11 (s, 1H), 3.30-3.25 (m, 1H), 1.75-1.90 (m, 1H), 1.41 (s, 6H), 0.95-0.93 (m, 2H), 0.88-0.82 (m, 4H), 0.59-0.71 (m, 2H). |
| 7 | 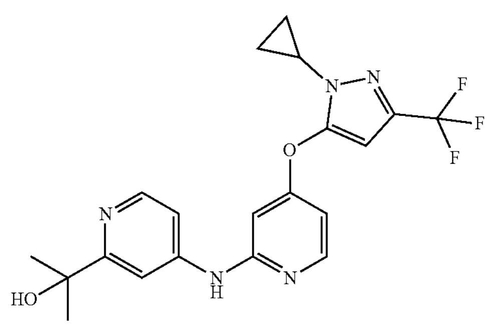 [SMILES: CC(C)(O)c1cc(Nc2cc(Oc3cc(C(F)(F)F)nn3C3CC3)ccn2)ccn1] | 420.2 | HNMR (300 MHz, DMSO-d₆, ppm): δ 9.61 (s, 1H), 8.28-8.23 (m, 2H), 7.73-7.71 (m, 2H), 6.76 (dd, J = 5.7, 2.1 Hz, 1H), 6.71 (s, 1H), 6.52 (d, J = 2.1 Hz, 1H), 5.13 (s, 1H), 3.57-3.54 (m, 1H), 1.41 (s, 6H), 1.08-1.05 (m, 2H), 0.98-1.03 (m, 2H).<br>FNMR (282 MHz, DMSO-d₆, ppm): δ −61.06. |
| 8 | 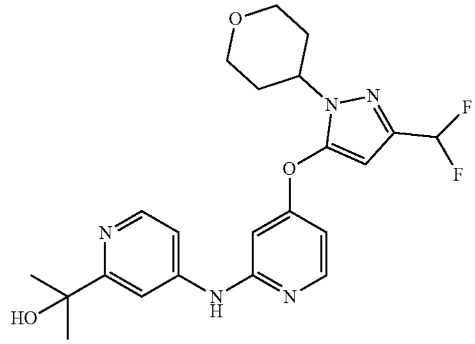 [SMILES: CC(C)(O)c1cc(Nc2cc(Oc3cc(C(F)F)nn3C3CCOCC3)ccn2)ccn1] | 446.5 | HNMR (400 MHz, DMSO-d₆, ppm): δ 9.69 (s, 1H), 8.23 (d, J = 6.0 Hz, 1H), 8.20 (d, J = 5.6 Hz, 1H), 7.71-7.69 (m, 2H), 6.95 (t, J = 54.4 Hz, 1H), 6.72 (dd, J = 6.0, 2.0 Hz, 1H), 6.50 (d, J = 2.0 Hz, 1H), 6.39 (s, 1H), 5.17 (s, 1H), 4.41-4.35 (m, 1H), 3.91-3.87 (m, 2H), 3.42-3.36 (m, 2H), 2.01-1.91 (m, 2H), 1.79-1.75 (m, 2H), 1.38 (s, 6H).<br>FNMR (376 MHz, DMSO-d₆, ppm): δ −111.23, −111.37. |

TABLE 1-continued

Characterization of Selected Compounds

| Compound No. | Structure | [M + H]⁺ | ¹H- and ¹⁹F-NMR |
|---|---|---|---|
| 9 | 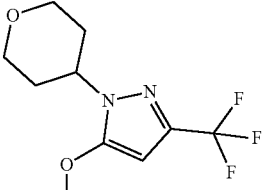 | 430.2 | HNMR (400 MHz, DMSO-d$_6$, ppm): δ 9.56 (s, 1H), 8.34 (t, J = 2.0 Hz, 1H), 8.26 (d, J = 6.0 Hz, 1H), 7.79-7.76 (m, 1H), 7.47 (t, J = 8.0 Hz, 1H), 7.34 (dt, J = 8.0, 1.2 Hz, 1H), 6.75 (dd, J = 5.6, 2.4 Hz, 1H), 6.71 (s, 1H), 6.47 (d, J = 2.0 Hz, 1H), 4.53-4.51 (m, 1H), 3.96-3.92 (m, 2H), 3.47-3.42 (m, 2H), 2.03-1.97 (m, 2H), 1.87-1.83 (m, 2H).<br>FNMR (376 MHz, DMSO-d$_6$, ppm): δ −61.24 |
| 10 | 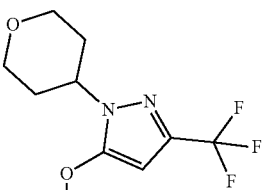 | 430.1 | HNMR (300 MHz, DMSO-d$_6$, ppm): δ 9.74 (s, 1H), 8.27 (d, J = 5.7 Hz, 1H), 7.87 (d, J = 8.7 Hz, 2H), 7.70 (d, J = 8.7 Hz, 2H), 6.80 (dd, J = 6.0, 2.4 Hz, 1H), 6.72 (s, 1H), 6.54 (d, J = 2.4 Hz, 1H), 4.57-4.47 (m, 1H), 3.96-3.91 (m, 2H), 3.48-3.40 (m, 2H), 2.08-1.94 (m, 2H), 1.91-1.80 (m, 2H).<br>FNMR (376 MHz, DMSO-d$_6$, ppm): δ −61.25 |
| 11 | 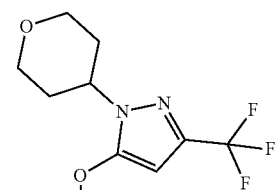 | 464.4 | HNMR (400 MHz, DMSO-d$_6$, ppm): δ 9.29 (s, 1H), 8.63 (d, J = 2.8 Hz, 1H), 8.17 (d, J = 6.0 Hz, 1H), 8.11 (dd, J = 8.4, 2.8 Hz, 1H), 7.54 (d, J = 8.4 Hz, 1H), 6.69 (s, 1H), 6.67 (dd, J = 6.0, 2.0 Hz, 1H), 6.44 (d, J = 2.0 Hz, 1H), 5.09 (bs, 1H), 4.55-4.48 (m, 1H), 3.94 (dd, J = 11.6, 3.6 Hz, 2H), 3.48-3.42 (m, 2H), 2.06-1.96 (m, 2H), 1.87-1.83 (m, 2H), 1.42 (s, 6H).<br>FNMR (376 MHz, DMSO-d$_6$, ppm): δ −61.29. |
| 12 | 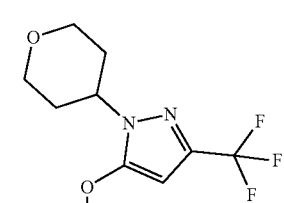 | 484.2 | HNMR (300 MHz, DMSO-d$_6$, ppm): δ 9.59 (s, 1H), 8.25 (d, J = 6.0 Hz, 1H), 7.82 (d, J = 8.7 Hz, 2H), 7.70 (d, J = 8.7 Hz, 2H), 7.15 (s, 2H), 6.77-6.74 (m, 1H), 6.71 (s, 1H), 6.52 (d, J = 2.4 Hz, 1H), 4.55-4.48 (m, 1H), 3.96-3.91 (m, 2H), 3.48-3.41 (m, 2H), 2.08-1.94 (m, 2H), 1.88-1.84 (m, 2H).<br>FNMR (282 MHz, DMSO-d$_6$, ppm): δ −61.23. |

TABLE 1-continued

Characterization of Selected Compounds

| Compound No. | Structure | [M + H]+ | 1H- and 19F-NMR |
|---|---|---|---|
| 13 | 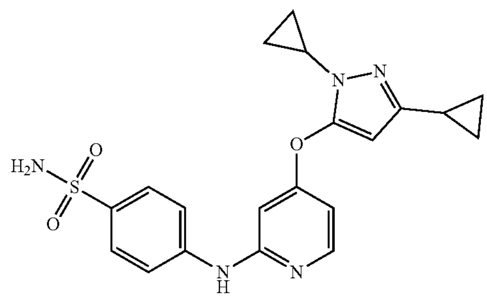 [SMILES: NS(=O)(=O)c1ccc(Nc2cc(Oc3cc(C4CC4)nn3C3CC3)ccn2)cc1] | 412.2 | HNMR (400 MHz, DMSO-d$_6$, ppm): δ 9.55 (s, 1H), 8.19 (d, J = 5.6 Hz, 1H), 7.82 (d, J = 8.8 Hz, 2H), 7.69 (d, J = 8.8 Hz, 2H), 7.15 (s, 2H), 6.65 (dd, J = 5.6, 2.4 Hz, 1H), 6.42 (d, J = 2.4 Hz, 1H), 5.79 (s, 1H), 3.28-3.24 (m, 1H), 1.84-1.82 (m, 1H), 0.97-0.92 (m, 2H), 0.90-0.83 (m, 4H), 0.67-0.63 (m, 2H). |
| 14 | 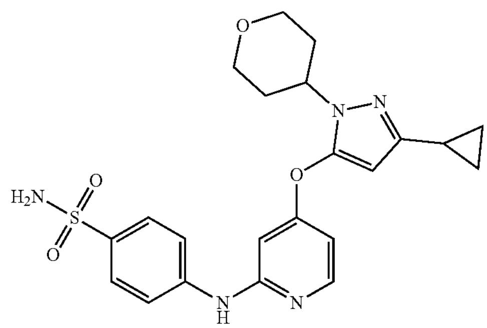 [SMILES: NS(=O)(=O)c1ccc(Nc2cc(Oc3cc(C4CC4)nn3C3CCOCC3)ccn2)cc1] | 456.3 | HNMR (300 MHz, DMSO-d$_6$, ppm): δ 9.58 (s, 1H), 8.19 (d, J = 5.7 Hz, 1H), 7.82 (d, J = 8.7 Hz, 2H), 7.69 (d, J = 8.7 Hz, 2H), 7.15 (s, 2H), 6.68-6.66 (m, 1H), 6.45 (s, 1H), 5.77 (s, 1H), 4.23-4.20 (m, 2H), 3.92-3.89 (m, 2H), 2.05-1.95 (m, 2H), 1.94-1.80 (m, 2H), 1.74-1.70 (m, 2H), 0.89-0.86 (m, 2H), 0.68-0.65 (m, 2H). |
| 15 | 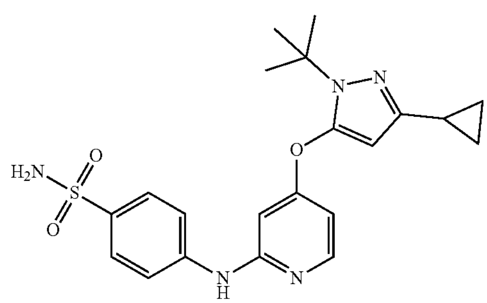 [SMILES: CC(C)(C)n1nc(C2CC2)cc1Oc1ccnc(Nc2ccc(S(N)(=O)=O)cc2)c1] | 428.2 | HNMR (400 MHz, DMSO-d$_6$, ppm): δ 9.55 (s, 1H), 8.18 (d, J = 5.6 Hz, 1H), 7.81 (d, J = 8.8 Hz, 2H), 7.69 (d, J = 8.8 Hz, 2H), 7.14 (s, 2H), 6.70-6.64 (m, 1H), 6.51 (d, J = 2.4 Hz, 1H), 5.74 (s, 1H), 1.88-1.80 (m, 1H), 1.48 (s, 9H), 0.86-0.84 (m, 2H), 0.65-0.63 (m, 2H). |
| 16 | 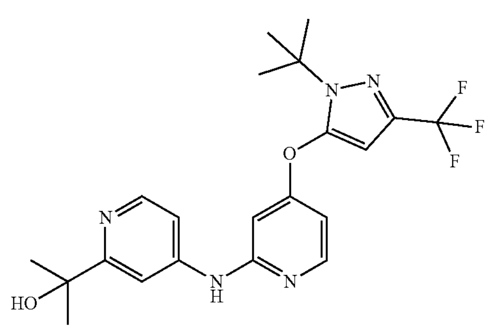 [SMILES: CC(C)(O)c1cc(Nc2cc(Oc3cc(C(F)(F)F)nn3C(C)(C)C)ccn2)ccn1] | 436.5 | HNMR (400 MHz, DMSO-d$_6$, ppm): δ 9.59 (s, 1H), 8.23 (d, J = 6.0 Hz, 1H), 8.19 (d, J = 6.0 Hz, 1H), 7.70-7.65 (m, 2H), 6.73 (dd, J = 5.6, 2.4 Hz, 1H), 6.67 (s, 1H), 6.55 (d, J = 2.0 Hz, 1H), 5.11 (s, 1H), 1.53 (s, 9H), 1.37 (s, 6H).<br>FNMR (376 MHz, DMSO-d$_6$, ppm): δ −61.13. |

TABLE 1-continued

Characterization of Selected Compounds

| Compound No. | Structure | [M + H]⁺ | ¹H- and ¹⁹F-NMR |
|---|---|---|---|
| 17 | 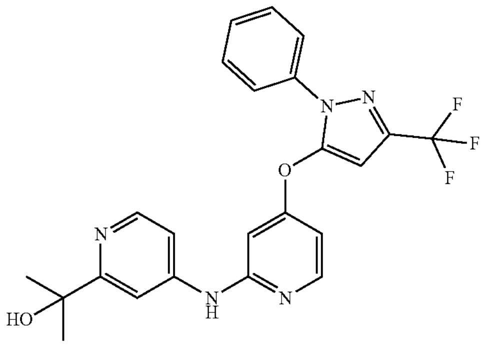 [SMILES: CC(C)(O)c1cc(Nc2cc(Oc3cc(C(F)(F)F)nn3-c3ccccc3)ccn2)ccn1] | 456.5 | HNMR (400 MHz, DMSO-d$_6$, ppm): δ 9.61 (s, 1H), 8.19 (d, J = 5.6 Hz, 2H), 7.70-7.63 (m, 2H), 7.62-7.57 (m, 2H), 7.55-7.50 (m, 2H), 7.45-7.42 (m, 1H), 6.95 (s, 1H), 6.72-6.71 (m, 1H), 6.53 (d, J = 2.0 Hz, 1H), 5.13 (s, 1H), 1.37 (s, 6H). |
| 20 | 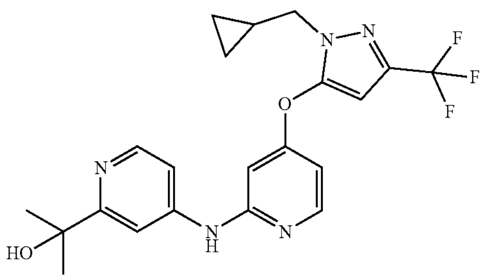 [SMILES: CC(C)(O)c1cc(Nc2cc(Oc3cc(C(F)(F)F)nn3CC3CC3)ccn2)ccn1] | 434.2 | HNMR (300 MHz, DMSO-d$_6$, ppm): δ 9.64 (s, 1H), 8.24-8.28 (m, 2H), 7.74-7.70 (m, 2H), 6.75 (dd, J = 5.7, 2.4 Hz, 1H), 6.72 (s, 1H), 6.57 (d, J = 2.4 Hz, 1H), 5.13 (s, 1H), 3.97 (d, J = 7.2 Hz, 2H), 1.41 (s, 6H), 1.26-1.12 (m, 1H), 0.50-0.45 (m, 2H), 0.35-0.31 (m, 2H). FNMR (282 MHz, DMSO-d$_6$, ppm): δ -61.22. |
| 21 | 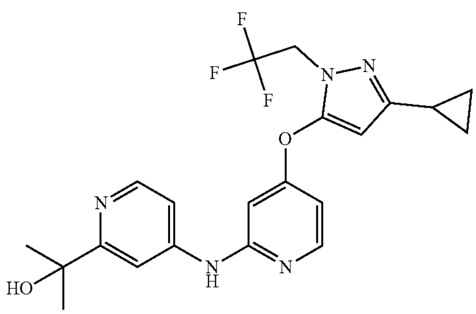 [SMILES: CC(C)(O)c1cc(Nc2cc(Oc3cc(C4CC4)nn3CC(F)(F)F)ccn2)ccn1] | 434.2 | HNMR (400 MHz, DMSO-d$_6$, ppm): δ 9.61 (s, 1H), 8.25-8.24 (m, 2H), 7.73-7.70 (m, 2H), 6.73-6.71 (m, 1H), 6.62 (d, J = 2.4 Hz, 1H), 5.91 (s, 1H), 5.13 (s, 1H), 4.93-4.86 (m, 2H), 1.91-1.86 (m, 1H), 1.42 (s, 6H), 0.94-0.86 (m, 2H), 0.74-0.65 (m, 2H). FNMR (376 MHz, DMSO-d$_6$, ppm): δ -61.65. |
| 22 | 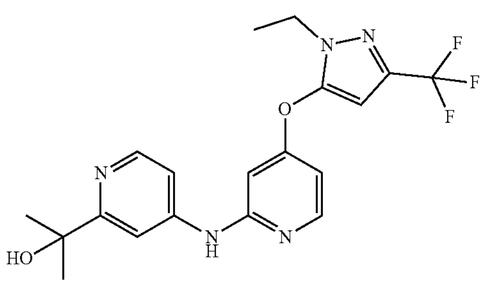 [SMILES: CCn1nc(C(F)(F)F)cc1Oc1ccnc(Nc2ccnc(C(C)(C)O)c2)c1] | 408.3 | HNMR (300 MHz, DMSO-d$_6$, ppm): δ 9.67 (s, 1H), 8.29-8.23 (m, 2H), 7.75-7.72 (m, 2H), 6.77-6.75 (m, 1H), 6.71 (s, 1H), 6.54 (d, J = 2.1 Hz, 1H), 5.16 (s, 1H), 4.09 (q, J = 7.2 Hz, 2H), 1.42 (s, 6H), 1.33 (t, J = 7.2 Hz, 3H). FNMR (282 MHz, DMSO-d$_6$, ppm): δ -61.26. |
| 23 | 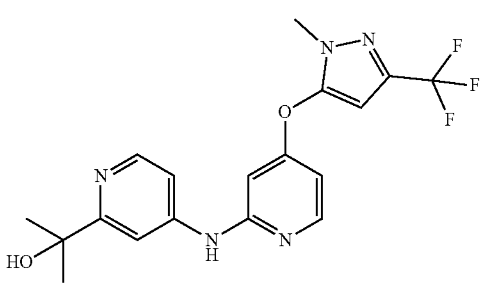 [SMILES: Cn1nc(C(F)(F)F)cc1Oc1ccnc(Nc2ccnc(C(C)(C)O)c2)c1] | 394.3 | HNMR (300 MHz, DMSO-d$_6$, ppm): δ 9.62 (s, 1H), 8.28-8.23 (m, 2H), 7.74-7.71 (m, 2H), 6.74 (dd, J = 5.7, 2.4 Hz, 1H), 6.70 (s, 1H), 6.53 (d, J = 2.4 Hz, 1H), 5.13 (s, 1H), 3.76 (s, 3H), 1.42 (s, 6H). FNMR (282 MHz, DMSO-d$_6$, ppm): δ -61.33. |

TABLE 1-continued

Characterization of Selected Compounds

| Compound No. | Structure | [M + H]⁺ | ¹H- and ¹⁹F-NMR |
|---|---|---|---|
| 24 | 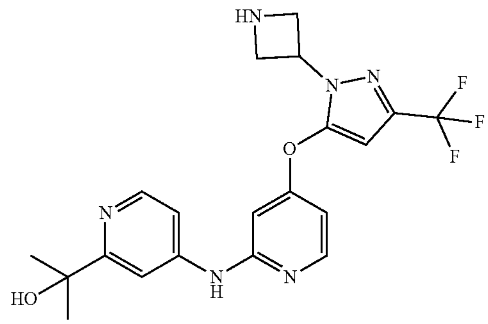 [SMILES: CC(C)(O)c1cc(Nc2cc(Oc3cc(C(F)(F)F)nn3C3CNC3)ccn2)ccn1] | 435.2 | HNMR (400 MHz, CD₃OD, ppm): δ 8.24 (d, J = 6.0 Hz, 1H), 8.19 (d, J = 5.6 Hz, 1H), 7.84 (d, J = 2.0 Hz, 1H), 7.65 (dd, J = 5.6, 2.0 Hz, 1H), 6.66 (dd, J = 6.0, 2.0 Hz, 1H), 6.49 (d, J = 2.4 Hz, 1H), 6.40 (s, 1H), 5.32-5.23 (m, 1H), 4.17 (dd, J = 9.6, 7.6 Hz, 2H), 3.83 (dd, J = 9.6, 8.4 Hz, 2H), 1.50 (s, 6H)<br>FNMR (376 MHz, CD₃OD, ppm): δ −64.62. |
| 25 | 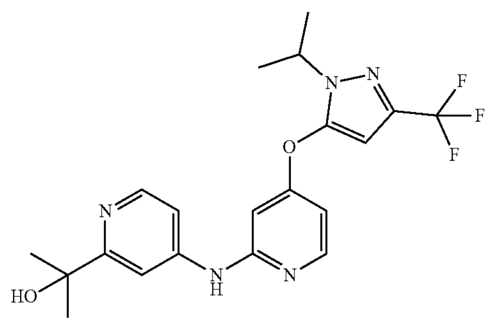 [SMILES: CC(C)n1nc(C(F)(F)F)cc1Oc1ccnc(Nc2ccnc(C(C)(C)O)c2)c1] | 422.1 | HNMR (400 MHz, DMSO-d₆, ppm): δ 9.62 (s, 1H), 8.22 (d, J = 5.6 Hz, 1H), 8.19 (d, J = 5.2 Hz, 1H), 7.70-7.67 (m, 2H), 6.72 (dd, J = 6.0, 2.4 Hz, 1H), 6.65 (s, 1H), 6.46 (d, J = 2.0 Hz, 1H), 5.12 (s, 1H), 4.53-4.46 (m, 1H), 1.38-1.32 (m, 12H).<br>FNMR (376 MHz, DMSO-d₆, ppm): δ −61.18. |
| 27 | 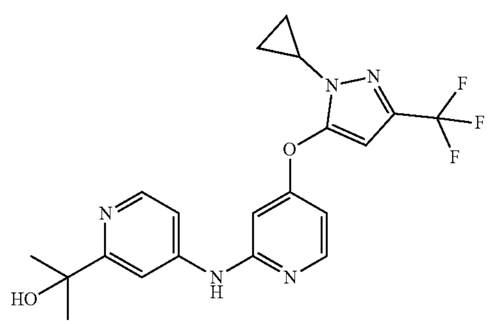 [SMILES: CC(C)(O)c1cc(Nc2cc(Oc3cc(C(F)(F)F)nn3C3CC3)ccn2)ccn1] | 420.1 | HNMR (400 MHz, DMSO-d₆, ppm): δ 9.58 (s, 1H), 8.23 (d, J = 5.6 Hz, 1H), 8.20 (d, J = 5.6 Hz, 1H), 7.70-7.66 (m, 2H), 6.72 (dd, J = 5.6, 2.0 Hz, 1H), 6.67 (s, 1H), 6.47 (d, J = 2.0 Hz, 1H), 5.10 (s, 1H), 3.54-3.50 (m, 1H), 1.37 (s, 6H), 1.07-1.01 (m, 2H), 0.98-0.92 (m, 2H).<br>FNMR (376 MHz, DMSO-d₆, ppm): δ −61.39. |
| 28<br>Relative configuration | | 462.4 | HNMR (400 MHz, DMSO-d₆, ppm): δ 9.60 (s, 1H), 8.4-8.21 (m, 2H), 7.73-7.71 (m, 2H), 6.67 (dd, J = 7.6, 2.8 Hz, 1H), 6.47 (d, J = 2.8 Hz, 1H), 5.81 (s, 1H), 5.12 (s, 1H), 4.39-4.27 (m, 2H), 4.26-4.17 (m, 1H), 2.28-2.17 (m, 2H), 1.92-1.77 (m, 7H), 1.41 (s, 6H), 0.96-0.80 (m, 2H), 0.76-0.60 (m, 2H). |

TABLE 1-continued

Characterization of Selected Compounds

| Compound No. | Structure | [M + H]+ | 1H- and 19F-NMR |
|---|---|---|---|
| 29 Relative configuration | 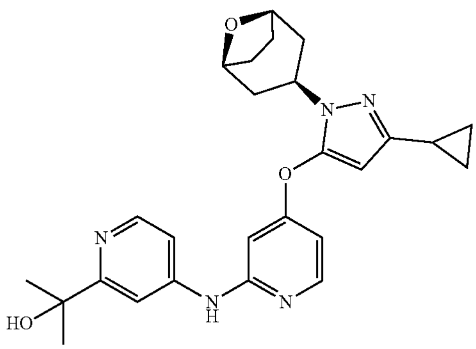 [SMILES: CC(C)(O)c1cc(Nc2cc(Oc3cc(C4CC4)nn3[C@@H]3C[C@H]4CC[C@@H](C3)O4)ccn2)ccn1] | 462.4 | HNMR (400 MHz, DMSO-d6, ppm): δ 9.61 (s, 1H), 8.23 (dd, J = 7.6, 2.4 Hz, 2H), 7.70-7.72 (m, 2H), 6.71 (dd, J = 7.6, 2.4 Hz, 1H), 6.48 (d, J = 2.4 Hz, 1H), 5.77 (s, 1H), 5.12 (s, 1H), 4.43-4.26 (m, 3H), 2.16-2.00 (m, 2H), 1.92-1.75 (m, 3H), 1.71-1.58 (m, 4H), 1.41 (s, 6H), 0.92-0.81 (m, 2H), 0.72-0.60 (m, 2H). |
| 30 Relative configuration | 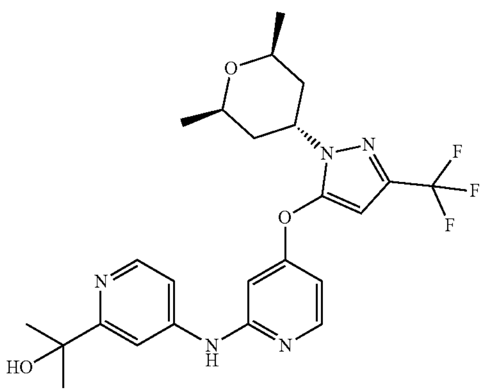 [SMILES: C[C@@H]1C[C@@H](n2nc(C(F)(F)F)cc2Oc2ccnc(Nc3ccnc(C(C)(C)O)c3)c2)C[C@H](C)O1] | 492.1 | HNMR (400 MHz, DMSO-d6, ppm): δ 9.61 (s, 1H), 8.23 (d, J = 5.6 Hz, 1H), 8.20 (d, J = 5.6 Hz, 1H), 7.70-7.67 (m, 2H), 6.72 (dd, J = 5.6, 2.0 Hz, 1H), 6.66 (s, 1H), 6.50 (d, J = 2.0 Hz, 1H), 5.11 (s, 1H), 4.51-4.49 (m, 1H), 3.56-3.52 (m, 2H), 1.86-1.84 (m, 2H), 1.56 (q, J = 12.0 Hz, 2H), 1.37 (s, 6H), 1.08 (d, J = 6.0 Hz, 6H). |
| 31 Relative configuration | 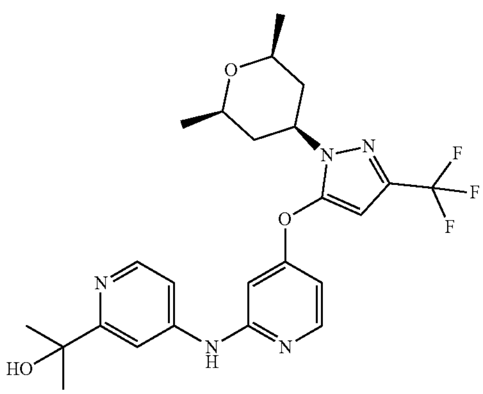 [SMILES: C[C@@H]1C[C@H](n2nc(C(F)(F)F)cc2Oc2ccnc(Nc3ccnc(C(C)(C)O)c3)c2)C[C@H](C)O1] | 492.1 | HNMR (400 MHz, DMSO-d6, ppm): δ 9.59 (s, 1H), 8.22 (d, J = 5.6 Hz, 1H), 8.20 (d, J = 5.6 Hz, 1H), 7.70-7.66 (m, 2H), 6.73-6.71 (m, 2H), 6.48 (d, J = 2.0 Hz, 1H), 5.10 (s, 1H), 4.68 (s, 1H), 4.05-4.01 (m, 2H), 1.83-1.80 (m, 2H), 1.63-1.57 (m, 2H), 1.37 (s, 6H), 1.03 (d, J = 6.4 Hz, 6H). |
| 32 | 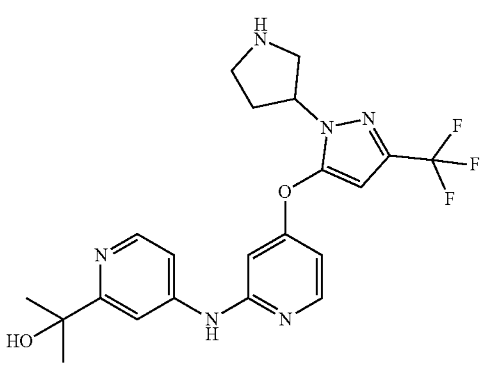 [SMILES: CC(C)(O)c1cc(Nc2cc(Oc3cc(C(F)(F)F)nn3C3CCNC3)ccn2)ccn1] | 449.1 | HNMR (400 MHz, DMSO-d6, ppm): δ 9.59 (s, 1H), 8.23 (d, J = 5.6 Hz, 1H), 8.20 (d, J = 5.6 Hz, 1H), 7.70-7.66 (m, 2H), 6.72-6.69 (m, 2H), 6.44 (d, J = 2.0 Hz, 1H), 5.10 (s, 1H), 4.74-4.70 (m, 1H), 3.11-3.06 (m, 1H), 2.96-2.93 (m, 1H), 2.91-2.79 (m, 2H), 2.05-1.97 (m, 2H), 1.37 (s, 6H). |

TABLE 1-continued

Characterization of Selected Compounds

| Compound No. | Structure | [M + H]+ | 1H- and 19F-NMR |
|---|---|---|---|
| 33 | 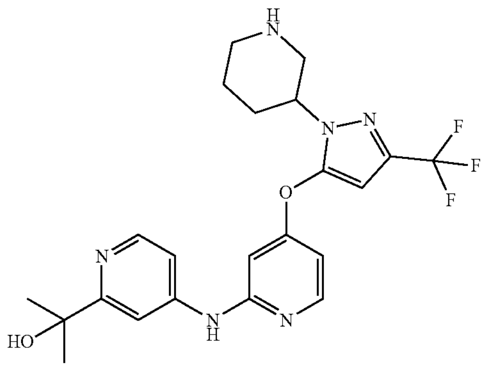 [SMILES: CC(C)(O)c1cc(Nc2cc(Oc3cc(C(F)(F)F)nn3C3CCCNC3)ccn2)ccn1] | 463.1 | HNMR (400 MHz, CD3OD, ppm): δ 8.25 (d, J = 6.0 Hz, 1H), 8.19 (d, J = 6.0 Hz, 1H), 7.86 (d, J = 2.0 Hz, 1H), 7.68-7.66 (m, 1H), 6.71-6.69 (m, 1H), 6.53 (d, J = 2.4 Hz, 1H), 6.40 (s, 1H), 4.35-4.30 (m, 1H), 3.17-3.13 (m, 1H), 3.08-2.96 (m, 2H), 2.67-2.61 (m, 1H), 2.10-2.04 (m, 2H), 1.87-1.83 (m, 1H), 1.61-1.60 (m, 1H) 1.51 (s, 6H). |
| 34 | 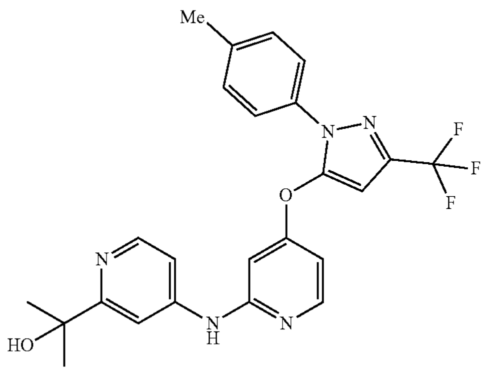 [SMILES: Cc1ccc(-n2nc(C(F)(F)F)cc2Oc2ccnc(Nc3ccnc(C(C)(C)O)c3)c2)cc1] | 470.1 | HNMR (400 MHz, CD3OD, ppm): δ 8.18-8.16 (m, 2H), 7.82 (d, J = 1.6 Hz, 1H), 7.61 (dd, J = 5.6, 2.4 Hz, 1H), 7.46 (d, J = 8.4 Hz, 2H), 7.29 (d, J = 8.4 Hz, 2H), 6.62 (dd, J = 6.0, 2.0 Hz, 1H), 6.58 (s, 1H), 6.48 (d, J = 2.0 Hz, 1H), 2.35 (s, 3H), 1.50 (s, 6H).<br>FNMR (376 MHz, CD3OD, ppm): δ -64.66. |
| 35 | 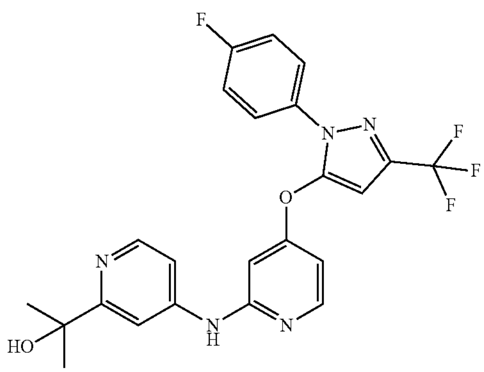 [SMILES: CC(C)(O)c1cc(Nc2cc(Oc3cc(C(F)(F)F)nn3-c3ccc(F)cc3)ccn2)ccn1] | 474.1 | HNMR (400 MHz, DMSO-d6, ppm): δ 9.59 (s, 1H), 8.19 (d, J = 5.6 Hz, 2H), 7.67-7.64 (m, 4H), 7.39-7.34 (m, 2H), 6.93 (s, 1H), 6.71 (dd, J = 5.6, 2.0 Hz, 1H), 6.54 (s, 1H), 5.09 (s, 1H), 1.36 (s, 6H). |
| 36 | 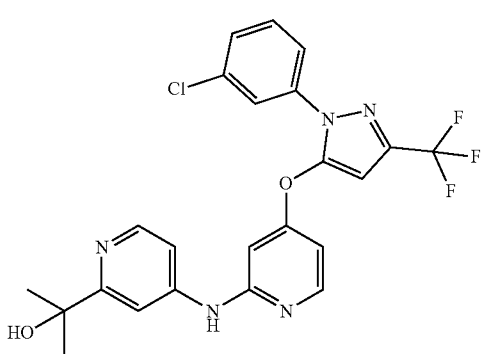 [SMILES: CC(C)(O)c1cc(Nc2cc(Oc3cc(C(F)(F)F)nn3-c3cccc(Cl)c3)ccn2)ccn1] | 490.0 | HNMR (400 MHz, CD3OD, ppm): δ 8.21 (d, J = 5.6 Hz, 1H), 8.17 (d, J = 5.6 Hz, 1H), 7.83 (d, J = 2.0 Hz, 1H), 7.71-7.69 (m, 1H), 7.66-7.58 (m, 2H), 7.50-7.40 (m, 2H), 6.67 (dd, J = 5.6, 2.4 Hz, 1H), 6.60 (s, 1H), 6.54 (d, J = 2.4 Hz, 1H), 1.50 (s, 6H).<br>FNMR (376 MHz, CD3OD, ppm): δ -64.84. |

TABLE 1-continued

Characterization of Selected Compounds

| Compound No. | Structure | [M + H]⁺ | ¹H- and ¹⁹F-NMR |
|---|---|---|---|
| 37 | 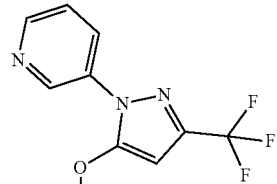 | 457.1 | HNMR (400 MHz, CD₃OD, ppm): δ 8.89 (d, J = 2.4 Hz, 1H), 8.59 (dd, J = 4.8, 1.2 Hz, 1H), 8.22 (d, J = 6.0 Hz, 1H), 8.19-8.15 (m, 2H), 7.83 (d, J = 2.0 Hz, 1H), 7.64 (dd, J = 5.6, 2.0 Hz, 1H), 7.59 (dd, J = 8.4, 4.8 Hz, 1H), 6.72-6.70 (m, 1H), 6.65 (s, 1H), 6.59 (d, J = 2.0 Hz, 1H), 1.50 (s, 6H). |
| 38 | 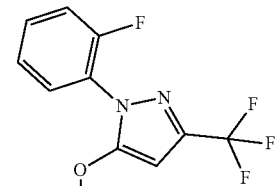 | 474.1 | HNMR (400 MHz, CD₃OD, ppm): δ 8.35 (d, J = 5.6 Hz, 1H), 8.23-8.04 (m, 3H), 7.58-7.56 (m, 2H), 7.35-7.30 (m, 2H), 6.89-6.87 (m, 1H), 6.75 (s, 1H), 6.67 (s, 1H), 1.60 (d, J = 1.2 Hz, 6H). FNMR (376 MHz, CD₃OD, ppm): δ -64.86, -77.01. |
| 40 | 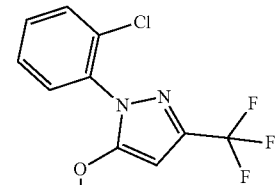 | 490.0 | HNMR (400 MHz, CD₃OD, ppm): δ 8.18-8.17 (m, 2H), 7.83 (d, J = 2.0 Hz, 1H), 7.64-7.60 (m, 2H), 7.55-7.52 (m, 2H), 7.49-7.45 (m, 1H), 6.62 (dd, J = 5.6, 2.0 Hz, 1H), 6.59-6.57 (m, 2H), 1.50 (s, 6H). FNMR (376 MHz, CD₃OD, ppm): δ -64.76. |
| 41 | 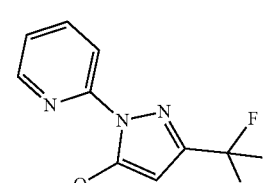 | 457.1 | HNMR (400 MHz, CD₃OD, ppm): δ 8.40 (dd, J = 4.8, 1.2 Hz, 1H), 8.17 (t, J = 6.0 Hz, 2H), 8.01-7.97 (m, 1H), 7.82-7.78 (m, 2H), 7.62-7.60 (m, 1H), 7.42-7.39 (m, 1H), 6.65-6.63 (m, 2H), 6.51 (d, J = 2.0 Hz, 1H), 1.50 (s, 6H). |

TABLE 1-continued

Characterization of Selected Compounds

| Compound No. | Structure | [M + H]+ | 1H- and 19F-NMR |
|---|---|---|---|
| 43 | 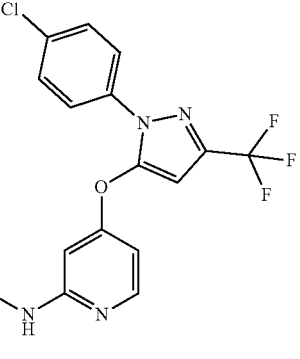 | 490.0 | HNMR (400 MHz, CD3OD, ppm): δ 8.36 (d, J = 5.6 Hz, 1H), 8.21 (d, J = 6.8 Hz, 1H), 8.19-7.91 (m, 2H), 7.65 (d, J = 8.8 Hz, 2H), 7.51 (d, J = 8.8 Hz, 2H), 6.92 (dd, J = 5.6, 2.4 Hz, 1H), 6.70 (d, J = 2.0 Hz, 1H), 6.67 (s, 1H), 1.60 (s, 6H).<br>FNMR (376 MHz, CD3OD, ppm): δ −64.83. |
| 45 | 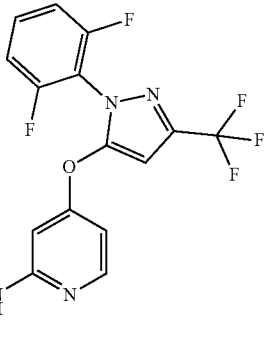 | 492.0 | HNMR (400 MHz, CD3OD, ppm): δ 8.37 (d, J = 8.0 Hz, 1H), 8.23 (d, J = 8.0 Hz, 1H), 8.14-8.04 (m, 2H), 7.67-7.59 (m, 1H), 7.23 (t, J = 8.0 Hz, 2H), 6.88 (dd, J = 5.6, 2.4 Hz, 1H), 6.75 (d, J = 2.4 Hz, 1H), 6.71 (s, 1H), 1.61 (s, 6H). |
| 48 | 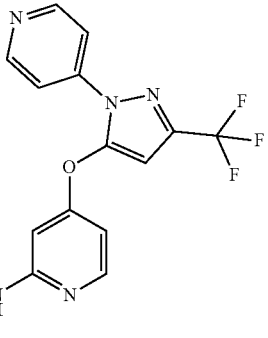 | 457.1 | HNMR (400 MHz, CD3OD, ppm): δ 8.66 (d, J = 6.0 Hz, 2H), 8.27 (d, J = 5.6 Hz, 1H), 8.19 (d, J = 6.0 Hz, 1H), 7.87-7.86 (m, 3H), 7.66 (dd, J = 5.6, 2.0 Hz, 1H), 6.79 (dd, J = 5.6, 2.0 Hz, 1H), 6.65-6.64 (m, 2H), 1.51 (s, 6H).<br>FNMR (376 MHz, CD3OD, ppm): δ −65.21. |
| 49 (TFA salt) Relative configuration | 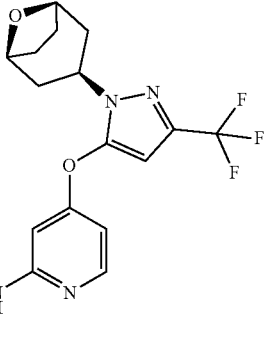 | 490.1 | HNMR (400 MHz, DMSO-d6, ppm): δ 13.72 (s, 1H), 10.90 (s, 1H), 8.42 (d, J = 5.6 Hz, 1H), 8.34 (d, J = 6.8 Hz, 1H), 8.12-7.82 (m, 2H), 7.06 (dd, J = 5.6, 2.4 Hz, 1H), 6.77-6.70 (m, 2H), 6.21 (s, 1H), 4.62-4.57 (m, 1H), 4.45-4.35 (m, 2H), 2.07-2.01 (m, 2H), 1.82-1.80 (m, 2H), 1.75-1.67 (m, 4H), 1.51 (s, 6H). |

TABLE 1-continued

Characterization of Selected Compounds

| Compound No. | Structure | [M + H]+ | 1H- and 19F-NMR |
|---|---|---|---|
| 50 (TFA salt) Relative configuration | 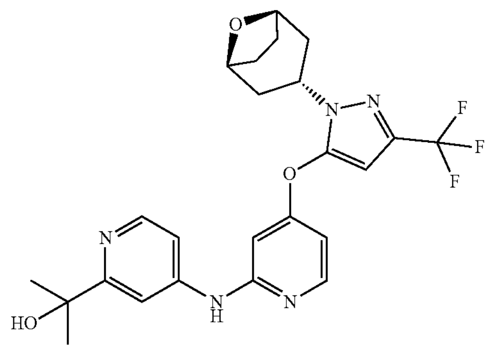 [SMILES: CC(C)(O)c1cc(Nc2cc(Oc3cc(C(F)(F)F)nn3[C@H]3C[C@H]4CC[C@@H](C3)O4)ccn2)ccn1] | 490.1 | HNMR (400 MHz, DMSO-d$_6$, ppm): δ 13.72 (s, 1H), 10.89 (s, 1H), 8.40 (d, J = 6.0 Hz, 1H), 8.34 (d, J = 6.8 Hz, 1H), 8.12-7.88 (m, 2H), 7.02 (dd, J = 6.0, 2.4 Hz, 1H), 6.74 (s, 1H), 6.69 (d, J = 2.0 Hz, 1H), 6.21 (s, 1H), 4.47-4.44 (m, 1H), 4.37-4.28 (s, 2H), 2.35-2.27 (m, 2H), 1.88-1.83 (m, 2H), 1.80-1.76 (m, 4H), 1.51 (s, 6H). |
| 51 | 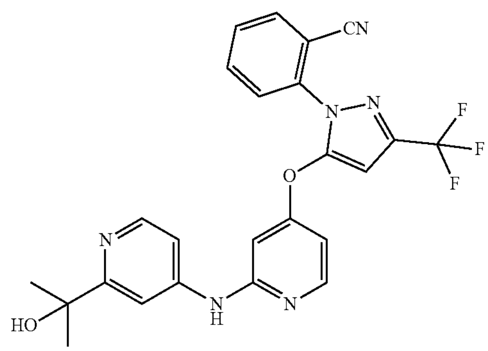 [SMILES: CC(C)(O)c1cc(Nc2cc(Oc3cc(C(F)(F)F)nn3-c3ccccc3C#N)ccn2)ccn1] | 481.1 | HNMR (400 MHz, CD$_3$OD, ppm): δ 8.21-8.17 (m, 2H), 7.94 (d, J = 7.6 Hz, 1H), 7.87-7.84 (m, 2H), 7.73-7.68 (m, 2H), 7.64 (dd, J = 5.6 Hz, 2.0 Hz, 1H), 6.68-6.62 (m, 2H), 6.63 (s, 1H), 1.50 (s, 6H). FNMR (376 MHz, CD$_3$OD, ppm): δ −64.95. |
| 52 (TFA salt) | 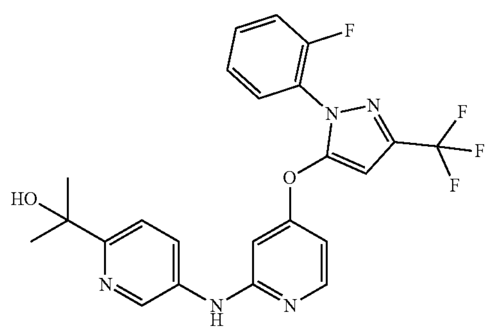 [SMILES: CC(C)(O)c1ccc(Nc2cc(Oc3cc(C(F)(F)F)nn3-c3ccccc3F)ccn2)cn1] | 474.1 | HNMR (400 MHz, DMSO-d$_6$, ppm): δ 10.00 (br s, 1H), 9.15 (br s, 1H), 8.32 (d, J = 8.8 Hz, 1H), 8.18 (d, J = 5.6 Hz, 1H), 7.90 (d, J = 8.8 Hz, 1H), 7.66 (t, J = 7.6 Hz, 1H), 7.61-7.57 (m, 1H), 7.48 (t, J = 9.2 Hz, 1H), 7.37 (t, J = 7.6 Hz, 1H), 6.98 (s, 1H), 6.73 (dd, J = 6.0, 2.0 Hz, 1H), 6.56 (d, J = 2.0 Hz, 1H), 1.49 (s, 6H). |
| 53 (TFA salt) | 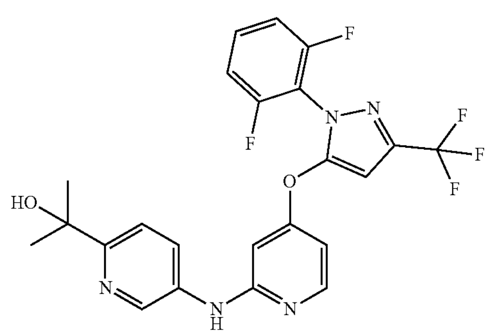 [SMILES: CC(C)(O)c1ccc(Nc2cc(Oc3cc(C(F)(F)F)nn3-c3c(F)cccc3F)ccn2)cn1] | 492.0 | HNMR (400 MHz, DMSO-d$_6$, ppm): δ 9.98 (s, 1H), 9.12 (s, 1H), 8.32-8.30 (m, 1H), 8.18 (d, J = 6.0 Hz, 1H), 7.87 (d, J = 9.2 Hz, 1H), 7.75-7.69 (m, 1H), 7.44-7.40 (m, 2H), 7.05 (s, 1H), 6.71 (dd, J = 6.0, 2.0 Hz, 1H), 6.55 (d, J = 2.0 Hz, 1H), 1.49 (s, 6H). |

TABLE 1-continued

Characterization of Selected Compounds

| Compound No. | Structure | [M + H]⁺ | ¹H- and ¹⁹F-NMR |
|---|---|---|---|
| 54 (TFA salt) | 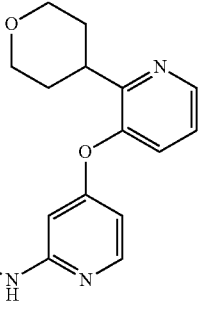 | 407.4 | HNMR (400 MHz, D₂O, ppm): δ 8.43 (d, J = 5.6 Hz, 1H), 8.25 (d, J = 6.0 Hz, 1H), 8.12-8.07 (m, 2H), 7.79-7.76 (m, 1H), 7.64 (d, J = 2.0 Hz, 1H), 7.54 (dd, J = 7.2, 2.0 Hz, 1H), 6.80 (dd, J = 6.0, 2.0 Hz, 1H), 6.76 (d, J = 2.0 Hz, 1H), 3.96 (m, 2H), 3.52-3.43 (m, 3H), 1.93-1.87 (m, 2H), 1.79-1.76 (m, 2H), 1.50 (s, 6H). |
| 55 | 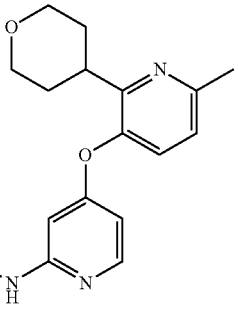 | 421.5 | HNMR (400 MHz, DMSO-d₆, ppm): δ 9.41 (s, 1H), 8.17-8.13 (m, 2H), 7.65-7.64 (m, 2H), 7.47 (d, J = 8.0 Hz, 1H), 7.21 (d, J = 8.0 Hz, 1H), 6.57-6.55 (m, 1H), 6.16 (d, J = 2.0 Hz, 1H), 5.06 (s, 1H), 3.85 (m, 2H), 3.31-3.26 (m, 2H), 3.04-2.98 (m, 1H), 2.48 (s, 3H), 1.87-1.83 (m, 2H), 1.50-1.47 (m, 2H), 1.36 (s, 6H). |
| 57 | 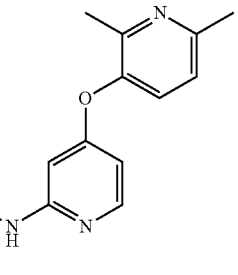 | 351.3 | HNMR (300 MHz, DMSO-d₆, ppm): δ 9.45 (s, 1H), 8.21 (d, J = 5.4 Hz, 1H), 8.17 (d, J = 6.0 Hz, 1H), 7.70-7.65 (m, 2H), 7.51 (d, J = 8.1 Hz, 1H), 7.24 (d, J = 8.1 Hz, 1H), 6.55 (dd, J = 5.7, 2.1 Hz, 1H), 6.18 (d, J = 2.1 Hz, 1H), 5.12 (s, 1H), 2.48 (s, 3H), 2.29 (s, 3H), 1.40 (s, 6H). |
| 58 | 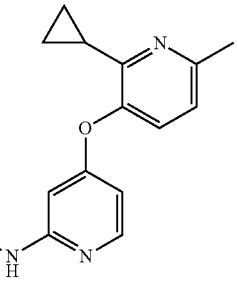 | 377.2 | HNMR (300 MHz, DMSO-d₆, ppm): δ 9.45 (s, 1H), 8.20 (d, J = 6.3 Hz, 1H), 8.17 (d, J = 5.7 Hz, 1H), 7.70-7.66 (m, 2H), 7.48 (d, J = 8.1 Hz, 1H), 7.13 (d, J = 8.1 Hz, 1H), 6.59 (dd, J = 5.8, 2.2 Hz, 1H), 6.22 (d, J = 2.4 Hz, 1H), 5.09 (s, 1H), 2.44 (s, 3H), 2.08-1.96 (m, 1H), 1.40 (s, 6H), 1.00-0.94 (m, 2H), 0.92-0.82 (m, 2H). |

TABLE 1-continued

Characterization of Selected Compounds

| Compound No. | Structure | [M + H]⁺ | ¹H- and ¹⁹F-NMR |
|---|---|---|---|
| 59 | 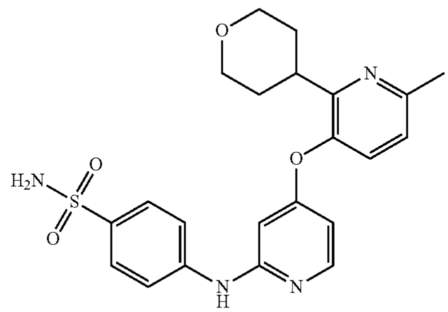 [SMILES: Cc1ccc(Oc2ccnc(Nc3ccc(S(N)(=O)=O)cc3)c2)c(C2CCOCC2)n1] | 441.2 | HNMR (400 MHz, DMSO-d₆, ppm): δ 9.42 (s, 1H), 8.15 (d, J = 6.0 Hz, 1H), 7.80 (d, J = 8.8 Hz, 2H), 7.67 (d, J = 8.8 Hz, 2H), 7.51 (d, J = 8.0 Hz, 1H), 7.25 (d, J = 8.4 Hz, 1H), 7.15-7.05 (m, 2H), 6.59 (dd, J = 6.0, 2.0 Hz, 1H), 6.16 (d, J = 2.0 Hz, 1H), 3.92-3.88 (m, 2H), 3.37-3.31 (m, 2H), 3.11-3.03 (m, 1H), 2.51 (s, 3H), 1.94-1.84 (m, 2H), 1.60-1.46 (m, 2H). |
| 62 | 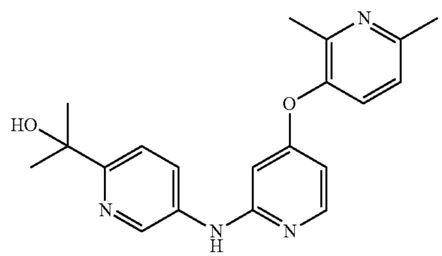 [SMILES: Cc1ccc(Oc2ccnc(Nc3ccc(C(C)(C)O)nc3)c2)c(C)n1] | 351.1 | HNMR (400 MHz, CD₃OD, ppm): δ 8.59 (d, J = 2.4 Hz, 1H), 8.06-8.01 (m, 2H), 7.54 (d, J = 8.8 Hz, 1H), 7.43 (d, J = 8.4 Hz, 1H), 7.22 (d, J = 8.4 Hz, 1H), 6.39 (dd, J = 5.6, 2.0 Hz, 1H), 6.10 (d, J = 2.0 Hz, 1H), 2.52 (s, 3H), 2.36 (s, 3H), 1.50 (s, 6H). |
| 67 | 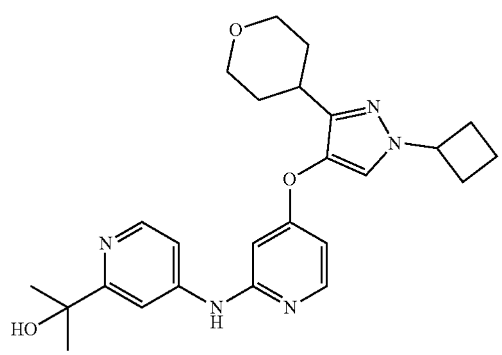 [SMILES: CC(C)(O)c1cc(Nc2cc(Oc3cn(C4CCC4)nc3C3CCOCC3)ccn2)ccn1] | 450.3 | HNMR (300 MHz, DMSO-d₆, ppm): δ 9.49 (s, 1H), 8.20 (d, J = 6.3 Hz, 1H), 8.14 (d, J = 6.0 Hz, 1H), 7.95 (s, 1H), 7.72-7.68 (m, 2H), 6.59 (dd, J = 5.7, 2.1 Hz, 1H), 6.37 (d, J = 2.1 Hz, 1H), 5.10 (s, 1H), 4.77-4.72 (m, 1H), 3.87-3.81 (m, 2H), 3.42-3.22 (m, 2H), 2.74-2.72 (m, 1H), 2.47-2.32 (m, 4H), 1.84-1.65 (m, 6H), 1.40 (s, 6H). |
| 68 | 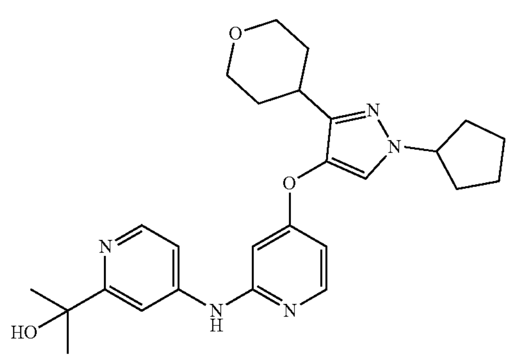 [SMILES: CC(C)(O)c1cc(Nc2cc(Oc3cn(C4CCCC4)nc3C3CCOCC3)ccn2)ccn1] | 464.3 | HNMR (300 MHz, DMSO-d₆, ppm): δ 9.53 (bs, 1H), 8.21 (d, J = 5.7 Hz, 1H), 8.14 (d, J = 6.0 Hz, 1H), 7.87 (s, 1H), 7.73-7.71 (m, 2H), 6.58 (dd, J = 5.7, 2.1 Hz, 1H), 6.37 (d, J = 2.1 Hz, 1H), 5.14 (s, 1H), 4.64-5.59 (m, 1H), 3.89-3.75 (m, 2H), 3.35-3.27 (m, 2H), 2.81-2.65 (m, 1H), 2.15-2.05 (m, 2H), 1.99-1.85 (m, 2H), 1.84-1.72 (m, 2H), 1.71-1.55 (m, 6H), 1.41 (s, 6H). |

TABLE 1-continued

Characterization of Selected Compounds

| Compound No. | Structure | [M + H]+ | 1H- and 19F-NMR |
|---|---|---|---|
| 69 | 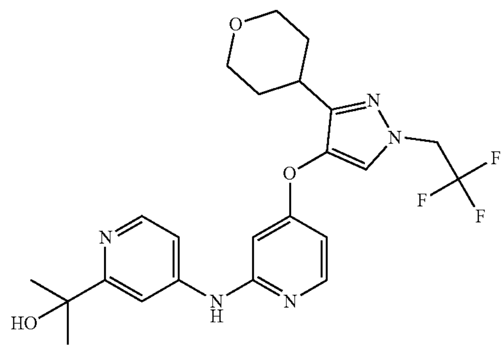 [SMILES: CC(C)(O)c1cc(Nc2cc(Oc3cn(CC(F)(F)F)nc3C3CCOCC3)ccn2)ccn1] | 478.2 | HNMR (300 MHz, DMSO-d6, ppm): δ 9.54 (s, 1H), 8.21 (d, J = 6.3 Hz, 1H), 8.16 (d, J = 6.0 Hz, 1H), 7.96 (s, 1H), 7.72-7.70 (m, 2H), 6.56 (dd, J = 5.7, 2.4 Hz, 1H), 6.38 (d, J = 2.1 Hz, 1H), 5.13-5.07 (m, 3H), 3.86-3.81 (m, 2H), 3.34-3.28 (m, 2H), 2.83-2.72 (m, 1H), 1.71-1.64 (m, 4H), 1.41 (s, 6H). FNMR (282 MHz, DMSO-d6, ppm): δ −70.20. |
| 76 | 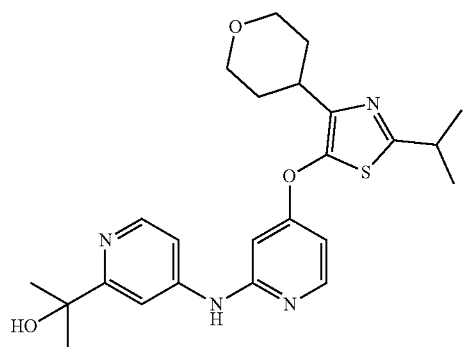 [SMILES: CC(C)c1nc(C2CCOCC2)c(Oc2ccnc(Nc3ccnc(C(C)(C)O)c3)c2)s1] | 455.5 | HNMR (400 MHz, CD3OD, ppm): δ 8.34 (d, J = 5.6 Hz, 1H), 8.22-8.05 (m, 3H), 6.87 (dd, J = 5.6, 2.0 Hz, 1H), 6.62 (d, J = 2.0 Hz, 1H), 3.96-3.92 (m, 2H), 3.44-3.38 (m, 2H), 3.25-3.20 (m, 1H), 2.92-2.84 (m, 1H), 2.01-1.91 (m, 2H), 1.64-1.61 (m, 8H), 1.36 (d, J = 6.8 Hz, 6H). |
| 77 | 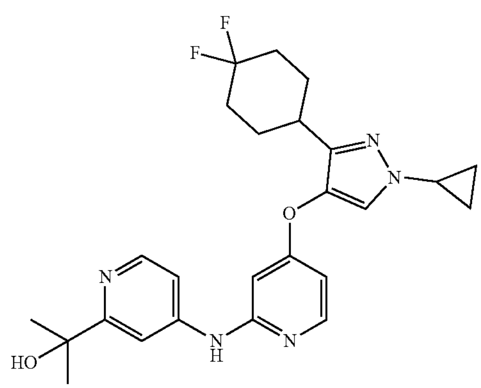 [SMILES: CC(C)(O)c1cc(Nc2cc(Oc3cn(C4CC4)nc3C3CCC(F)(F)CC3)ccn2)ccn1] | 470.5 | HNMR (400 MHz, DMSO-d6, ppm): δ 9.48 (s, 1H), 8.21 (d, J = 5.6 Hz, 1H), 8.14 (d, J = 5.6 Hz, 1H), 7.88 (s, 1H), 7.73-7.68 (m, 2H), 6.58 (dd, J = 6.0, 2.4 Hz, 1H), 6.38 (d, J = 2.4 Hz, 1H), 5.11 (s, 1H), 3.670-3.66 (m, 1H), 2.68-2.62 (m, 1H), 2.10-2.00 (m, 2H), 1.92-1.78 (m, 4H), 1.74-1.64 (m, 2H), 1.41 (s, 6H), 1.08-1.01 (m, 2H), 1.00-0.92 (m, 2H). FNMR (376 MHz, DMSO-d6, ppm): −90.26. |
| 78 (TFA salt) | 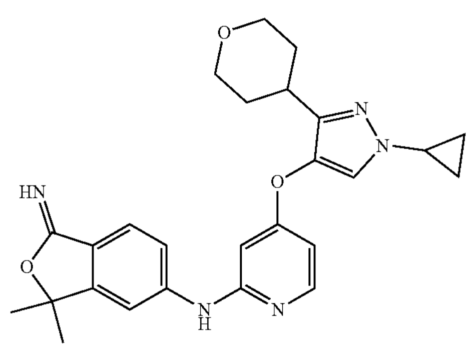 | 460.1 | HNMR (400 MHz, DMSO-d6, ppm): δ 11.16 (s, 1H), 10.93 (s, 1H), 10.06 (s, 1H), 8.17 (d, J = 5.6 Hz, 1H), 8.10 (s, 1H), 8.02 (d, J = 8.8 Hz, 1H), 7.87 (s, 1H), 7.75 (d, J = 7.6 Hz, 1H), 6.67 (dd, J = 6.0, 2.0 Hz, 1H), 6.43 (d, J = 2.0 Hz, 1H), 3.80-3.77 (m, 2H), 3.66-3.62 (m, 1H), 3.30-3.24 (m, 2H), 2.70-2.66 (m, 1H), 1.70 (s, 6H), 1.63-1.61 (m, 4H), 1.01-1.00 (m, 2H), 0.93-0.91 (m, 2H). |

TABLE 1-continued

Characterization of Selected Compounds

| Compound No. | Structure | [M + H]+ | 1H- and 19F-NMR |
|---|---|---|---|
| 79 | 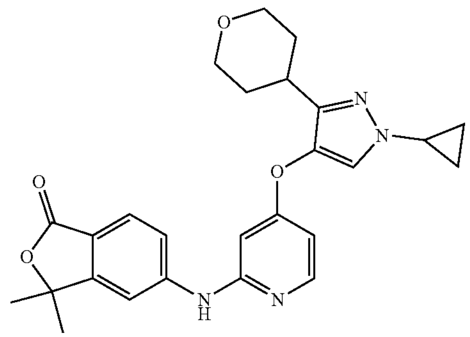 [SMILES: CC1(C)OC(=O)c2ccc(Nc3cc(Oc4cn(C5CC5)nc4C4CCOCC4)ccn3)cc21] | 461.1 | HNMR (400 MHz, DMSO-d6, ppm): δ 9.72 (s, 1H), 8.12 (d, J = 6.0 Hz, 1H), 7.95 (s, 1H), 7.86 (s, 1H), 7.64-7.60 (m, 2H), 6.60 (dd, J = 5.6, 2.0 Hz, 1H), 6.36 (d, J = 2.0 Hz, 1H), 3.80-3.77 (m, 2H), 3.65-3.61 (m, 1H), 3.30-3.24 (m, 2H), 2.70-2.64 (m, 1H), 1.63-1.61 (m, 4H), 1.54 (s, 6H), 1.00-0.99 (m, 2H), 0.94-0.91 (m, 2H). |
| 83 | 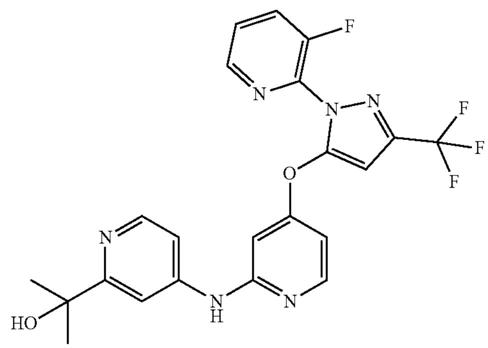 [SMILES: CC(C)(O)c1cc(Nc2cc(Oc3cc(C(F)(F)F)nn3-c3ncccc3F)ccn2)ccn1] | 475.1 | HNMR (400 MHz, DMSO-d6, ppm): δ 9.61 (s, 1H), 8.44 (d, J = 4.8 Hz, 1H), 8.20-8.17 (m, 2H), 8.13-8.08 (m, 1H), 7.75-7.71 (m, 1H), 7.68-7.65 (m, 2H), 7.00 (s, 1H), 6.66-6.64 (dd, J = 5.6, 2.4 Hz, 1H), 6.58 (d, J = 2.4 Hz, 1H), 5.09 (s, 1H), 1.37 (s, 6H). |
| 84 | 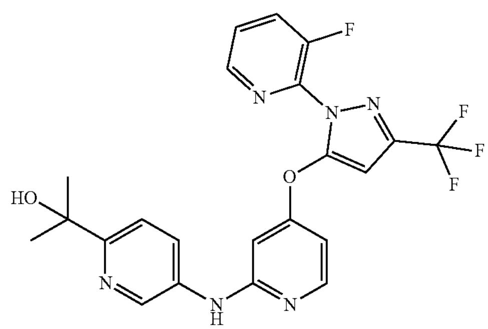 [SMILES: CC(C)(O)c1ccc(Nc2cc(Oc3cc(C(F)(F)F)nn3-c3ncccc3F)ccn2)cn1] | 475.1 | HNMR (400 MHz, DMSO-d6, ppm): δ 9.28 (s, 1H), 8.59 (d, J = 2.4 Hz, 1H), 8.46 (d, J = 4.4 Hz, 1H), 8.13-8.04 (m, 3H), 7.76-7.72 (m, 1H), 7.49 (d, J = 8.8 Hz, 1H), 6.99 (s, 1H), 6.55 (dd, J = 5.6, 2.4 Hz, 1H), 6.47 (d, J = 2.0 Hz, 1H), 5.05 (s, 1H), 1.38 (s, 6H). |
| 85 | 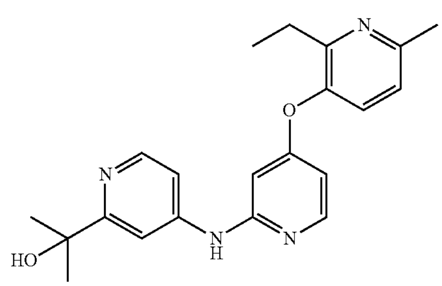 [SMILES: CCc1nc(C)ccc1Oc1ccnc(Nc2ccnc(C(C)(C)O)c2)c1] | 365.1 | HNMR (400 MHz, CD3OD, ppm): δ 8.17-8.13 (m, 2H), 7.78 (d, J = 2.0 Hz, 1H), 7.56 (dd, J = 5.6, 2.0 Hz, 1H), 7.42 (d, J = 8.4 Hz, 1H), 7.21 (d, J = 8.4 Hz, 1H), 6.50 (dd, J = 5.6, 2.0 Hz, 1H), 6.26 (d, J = 2.0 Hz, 1H), 2.71 (q, J = 7.6 Hz, 2H), 2.53 (s, 3H), 1.49 (s, 6H), 1.17 (t, J = 7.6 Hz, 3H). |
| 87 | 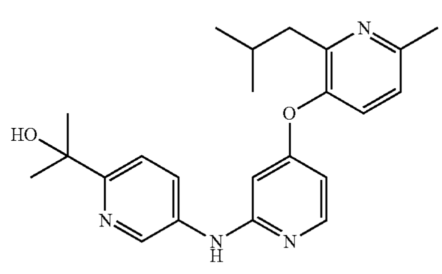 [SMILES: Cc1ccc(Oc2ccnc(Nc3ccc(C(C)(C)O)nc3)c2)c(CC(C)C)n1] | 393.2 | HNMR (400 MHz, DMSO-d6, ppm): δ 9.09 (s, 1H), 8.56 (d, J = 2.4 Hz, 1H), 8.08-8.05 (m, 1H), 8.02 (d, J = 5.6 Hz, 1H), 7.47-7.44 (m, 2H), 7.18 (d, J = 8.4 Hz, 1H), 7.42-7.40 (m, 1H), 6.05 (d, J = 2.0 Hz, 1H), 5.03 (s, 1H), 2.46-2.44 (m, 5H), 2.08-2.01 (m, 1H), 1.36 (s, 6H), 0.81 (d, J = 6.8 Hz, 6H). |

TABLE 1-continued

Characterization of Selected Compounds

| Compound No. | Structure | [M + H]+ | 1H- and 19F-NMR |
|---|---|---|---|
| 89 | 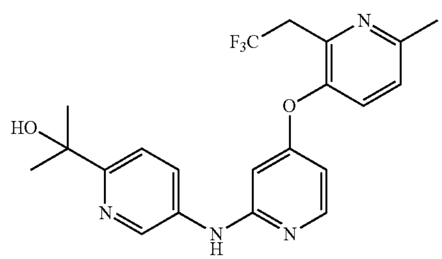 [SMILES: Cc1ccc(Oc2ccnc(Nc3ccc(C(C)(C)O)nc3)c2)c(CC(F)(F)F)n1] | 419.1 | HNMR (400 MHz, DMSO-d6, ppm): δ 9.09 (s, 1H), 8.56 (d, J = 2.0 Hz, 1H), 8.08-8.04 (m, 2H), 7.59 (d, J = 8.4 Hz, 1H), 7.47 (d, J = 8.4 Hz, 1H), 7.36 (d, J = 8.4 Hz, 1H), 6.46-6.44 (m, 1H), 6.13 (d, J = 2.0 Hz, 1H), 5.04 (s, 1H), 3.72-3.64 (m, 2H), 2.49 (s, 3H), 1.36 (s, 6H). |
| 90 | 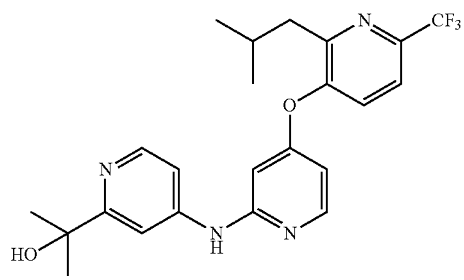 [SMILES: CC(C)Cc1nc(C(F)(F)F)ccc1Oc1ccnc(Nc2ccnc(C(C)(C)O)c2)c1] | 447.2 | HNMR (400 MHz, DMSO-d6, ppm): δ 9.45 (s, 1H), 8.20-8.17 (m, 2H), 7.84-7.83 (m, 2H), 7.65 (s, 2H), 6.62 (dd, J = 6.0 Hz, 2.0 Hz, 1H), 6.30 (d, J = 2.0 Hz, 1H), 5.08 (s, 1H), 2.63 (d, J = 6.8 Hz, 2H), 2.11-2.04 (m, 1H), 1.36 (s, 6 H), 0.84 (d, J = 6.8 Hz, 6H). |

Biological Example 1. TGFβR1 Kinase Inhibition Assay

TGFβR1 kinase assay was performed according to the instruction manual of the ADP-Glo™ Kinase Assay kit provided by Promega. Prepare 1× Kinase buffer (50 mM Tris pH7.5, 0.1% BSA, 10 mM MgCl$_2$, 1 mM DTT). Before activation reaction was started, Compounds were dissolved in DMSO and make 100× solution with 3-fold serial dilution for a total of 10 concentrations. Transfer 50 nL compounds to 384-well plate according to plate map using the automated liquid handler. Prepare enzyme mix containing 2× enzyme mix containing 40 nM TGFβR1 with 1× Kinase buffer, add 2.5 μL enzyme mix to 384-well plate and pre-incubate with compounds at RT for 10 minutes. Prepare 2× substrate mix containing 5.4 μM ATP 1× Kinase buffer and add 2.5 μL substrate mix to 384-well plate, react at RT for 120 min. Add 5 μL ADP-Glo Reagent to terminate the kinase reaction and deplete the remaining ATP, incubate at RT for 60 minutes. Add 10 μL Kinase Detection Reagent to convert ADP to ATP and allow the newly synthesized ATP to be measured using a luciferin reaction, incubate at RT for 30 minutes. Collect luminescence data with Envision.

The results are shown in the table 2.

TABLE 2

TGF βR1 kinase inhibition Activity of Representative Compounds

| Compound | TGFβR1 IC$_{50}$ (nM) |
|---|---|
| Compound A* | 22 |
| 1 | 61 |
| 2 | 53 |
| 3 | 825 |
| 4 | 60 |
| 5 | 43 |
| 6 | 46 |
| 7 | 557 |
| 8 | 173 |
| 9 | 163 |
| 10 | 131 |
| 11 | 24 |
| 12 | 28 |
| 13 | 44 |
| 14 | 37 |
| 15 | 94 |
| 16 | 34 |
| 17 | 12 |
| 18 | >10000 |
| 19 | 7706 |
| 20 | 48 |
| 21 | 37 |
| 22 | 54 |
| 23 | 38 |
| 24 | 223 |
| 25 | 66 |
| 26 | 88 |
| 27 | 58 |
| 28 | 35 |
| 29 | 19 |
| 30 | 89 |
| 31 | 1041 |
| 32 | 868 |
| 33 | 49 |
| 34 | 42 |
| 35 | 86 |
| 36 | 56 |
| 37 | 283 |
| 38 | 18 |
| 39 | 126 |
| 40 | 71 |
| 41 | 12 |
| 42 | 263 |
| 43 | 159 |
| 44 | 141 |

TABLE 2-continued

TGF βR1 kinase inhibition Activity of Representative Compounds

| Compound | TGFβR1 IC$_{50}$ (nM) |
|---|---|
| 45 | 13 |
| 46 | 66 |
| 47 | 103 |
| 48 | 132 |
| 49 | 32 |
| 50 | 113 |
| 51 | 55 |
| 52 | 21 |
| 53 | 18 |
| 54 | 56 |
| 55 | 35 |
| 56 | 220 |
| 57 | 21 |
| 58 | 39 |
| 59 | 32 |
| 60 | 50 |
| 61 | 116 |
| 62 | 29 |
| 63 | 82 |
| 64 | 32 |
| 65 | 14 |
| 66 | 4 |
| 67 | 51 |
| 68 | 631 |
| 69 | 454 |
| 70 | 80 |
| 71 | 25 |
| 72 | 111 |
| 73 | 14 |
| 74 | 17 |
| 75 | 6690 |
| 76 | 90 |

TABLE 2-continued

TGF βR1 kinase inhibition Activity of Representative Compounds

| Compound | TGFβR1 IC$_{50}$ (nM) |
|---|---|
| 77 | 17 |
| 78 | 22 |
| 79 | 29 |
| 80 | 57 |
| 81 | 51 |

*Compound A: 2-(4-(4-((1-cyclopropyl-3-(tetrahydro-2H-pyran-4-yl)-1H-pyrazol-4-yl)oxy)pyridin-2-yl)amino)pyridin-2-yl)propan-2-ol Biological Example 2. TGFβR2 Kinase Inhibition Assay The TGFβR2 enzyme reaction was carried out as follows: 50 nL of compound in DMSO (or DMSO controls) were stamped into 384 white, low-volume plates. 2.5 μL of 2× enzyme solution (final enzyme concentration was 3 ng/uL in 40 mMTris, 7.5; 20 mM MgCl$_2$; 0.1 mg/mL BSA; 1 mM DTT) was dispensed into assay plate. The plate was then sealed and spun at 1000 rpm for 30 s and incubated at room temperature for 10 min. Followed by addition of 2.5 μL of 2× substrate solution that contains both ATP (to make a final concentration of 10 uM) and TGFβR2 substrate (final concentration of 0.2 ug/uL). The plate was then sealed and spun at 1000 rpm for 30 s and the reaction was then incubated at room temperature for 120 min. After that 5 μL ADP-Glo™ Reagent was added into the assay wells to stop the reaction and deplete unconsumed ATP for 40 min at room temperature; then, 10 μL of Detection Reagent was added into the assay wells, followed by 40 min incubation to develop luminescence. The luminescence signal was then collected on Envision 2104 plate reader.

The results are shown in the table 3.

TABLE 3

TGF βR2 kinase inhibition Activity of Representative Compounds

| Compound | TGFβR2 IC$_{50}$ (uM) | Compound | TGFβR2 IC$_{50}$ (uM) | Compound | TGFβR2 IC$_{50}$ (uM) |
|---|---|---|---|---|---|
| 1 | >100 | 33 | >100 | 71 | >100 |
| 2 | >100 | 34 | 17 | 72 | >100 |
| 3 | >100 | 38 | 15 | 73 | >100 |
| 4 | 19 | 41 | 15 | 74 | >100 |
| 5 | >100 | 45 | 21 | 77 | 39 |
| 6 | >100 | 52 | 16 | 78 | >100 |
| 7 | >100 | 53 | 56 | 79 | 73 |
| 8 | >100 | 54 | >100 | 80 | 35 |
| 9 | >100 | 55 | 15 | | |
| 10 | >100 | 56 | 3 | | |
| 11 | >100 | 57 | >100 | | |
| 12 | >100 | 58 | 11 | | |
| 13 | >100 | 59 | 10 | | |
| 14 | >100 | 64 | 3 | | |
| 15 | >100 | 65 | 91 | | |
| 16 | 34 | 66 | 1 | | |
| 17 | 1 | 67 | >100 | | |
| 21 | >100 | 68 | >100 | | |
| 28 | 36 | 69 | >100 | | |
| 29 | 89 | 70 | >100 | | |

Biological Example 3. Human Hepatocyte Clearance Study

The in vitro human hepatocyte clearance of compounds described here was studied using pooled human hepatocytes purchased from BioreclamationIVT (Westbury, N.Y., Cat #X008001, Lot #TQJ). The assay was conducted according to manufacturer's instruction. Briefly, 10 mM stock solutions of test compounds and positive control (Verapamil) were prepared in 100% DMSO. Thawing media (50 mL)

used in the study consists of: 31 mL Williams E medium (GIBCO Cat #12551-032); 15 mL isotonic percoll (GE Healthcare Cat #17-0891-09); 500 uL 100× GlutaMax (GIBCO Cat #35050); 750 uL HEPES (GIBCO Cat #15630-080); 2.5 mL FBS (Corning Cat #35-076-CVR); 50 uL human insulin (GIBCO Cat #12585-014) and 5 uL dexamethasone (NICPBP). Incubation media is made of Williams E medium supplemented with 1× GlutaMax. Both thawing medium and incubation medium (serum-free) were placed in a 37° C. water bath for at least 15 minutes prior to use. Compound stock solutions were diluted to 100 μM by combining 198 μL of 50% acetonitrle/50% water and 2 μL of 10 mM stock solution. Verapamil was use as positive control in the assay. Vials of cryopreserved hepatocytes were removed from storage and thawed in a 37° C. water bath with gentle shaking. Contents of the vial were poured into the 50 mL thawing medium conical tube. Vials were centrifuged at 100 g for 10 minutes at room temperature. Thawing medium was aspirated and hepatocytes were re-suspended with serum-free incubation medium to yield ~1.5×10$^6$ cells/mL. Hepatocyte viability and density were counted using a Trypan Blue exclusion, and then cells were diluted with serum-free incubation medium to a working cell density of 0.5×10$^6$ viable cells/mL. Then, a portion of the hepatocytes at 0.5×10$^6$ viable cells/mL was boiled for 5 minutes prior to adding to the plate as negative control to eliminate the enzymatic activity so that little or no substrate turnover should be observed. The boiled hepatocytes were used to prepare negative samples. Aliquots of 198 μL hepatocytes were dispensed into each well of a 96-well non-coated plate. The plate was placed in the incubator on an orbital shaker at 500 rpm for approximately 10 minutes. Aliquots of 2 μL of the 100 μM test compound or positive control were added into respective wells of the non-coated 96-well plate to start the reaction. This assay was performed in duplicate. The plate was incubated in the incubator on an orbital shaker at 500 rpm for the designated time points. Twenty-five microliter of contents were transferred and mixed with 6 volumes (150 μL) of cold acetonitrile with IS (200 nM imipramine, 200 nM labetalol and 200 nM diclofenac) to terminate the reaction at time points of 0, 15, 30, 60, 90 and 120 minutes. Samples were centrifuged at 3,220 g for 25 minutes and aliquots of 150 μL of the supernatants were used for LC-MS/MS analysis. For data analysis, all calculations were carried out using Microsoft Excel. Peak areas were determined from extracted ion chromatograms. The in vitro half-life ($t_{1/2}$) of parent compound was determined by regression analysis of the percent parent disappearance vs. time curve. The in vitro half-life (in vitro ti) was determined from the slope value: in vitro $t_{1/2}$=0.693/k. Conversion of the in vitro $t_{1/2}$ (in minutes) into the scale-up unbound intrinsic clearance (Scaled-up unbound $CL_{int}$, in mL/min/kg) was done using the following equation (mean of duplicate determinations): Scaled-up unbound $CL_{int}$=kV/N× scaling factor, where V=incubation volume (0.5 mL); N=number of hepatocytes per well (0.25× 10$^6$ cells). Scaling factors for in vivo intrinsic clearance prediction using human hepatocytes are listed as: liver weight (g liver/kg body weight): 25.7; hepatocyte concentration (10$^6$ cells/g liver): 99; scaling factor: 2544.3.

The results are shown in the table 4.

TABLE 4

Human Hepatocyte Clearance of Exemplary Compounds

| Compound | Human Hepatocyte Remaining Percentage @ 120 min (%) | Human In vitro $T_{1/2}$ (min) | Human In vitro $Cl_{int}$ (μL/min/10$^6$ cells) | Human Scale-up $Cl_{int}$ (mL/min/kg) |
|---|---|---|---|---|
| Compound A* | 48 | 111 | 12.5 | 31.7 |
| 2 | 72 | 246 | 5.6 | 14.3 |
| 11 | 71 | 242 | 5.7 | 14.6 |
| 12 | 64 | 180 | 7.7 | 19.6 |
| 13 | 65 | 185 | 7.5 | 19.0 |
| 23 | 88 | 626 | 2.2 | 5.6 |
| 54 | 61 | 203 | 6.8 | 17.4 |
| 57 | 89 | 584 | 2.4 | 6.0 |

*Compound A: 2-(4-((4-((1-cyclopropyl-3-(tetrahydro-2H-pyran-4-yl)-1H-pyrazol-4-yl)oxy)pyridin-2-yl)amino)pyridin-2-yl)propan-2-ol
** If calculated $CL_{int}$ < 0, then $T_{1/2}$ and CLint were reported as "∞" and "0.00", respectively.

Biological Example 4. Assessment of P-Glycoprotein Substrate Potential of Test Compounds in MDR1-Transfected MDCK Cells MDCK-MDR1 cells were seeded into 96-well HTS Transwell plate at the density of 5.45×10$^5$/cm$^2$. Cells were cultivated for 4-7 days before the transport assay. Transepithelial electrical resistance (TEER) of MDCK-MDR1 monolayer was measured before the experiment with the Millicell Epithelial Volt-Ohm measuring system.

Transport assay: Cell monolayers were pre-incubated in transport medium (TM, HBSS with 25 mM HEPES, pH 7.4) for 30 min at 37° C. After preincubation, the study was initiated by adding the test compound to the donor side and TM to the receiver side. Compound transport was assessed at 1 μM in two directions (apical, AP to basolateral, BL and BL to AP) and the study was carried out in the presence and absence of P-gp inhibitor verapamil in both AP and BL compartments. After two hours incubation, aliquots of 50 μL from donor or receiver side were removed and mixed with 4 volumes of acetonitrile containing internal standards (200 nM alprazolam, 200 nM labetalol, 2 μM ketoprofen). Samples were analyzed by UPLC-MS/MS. All incubations were performed in duplicate. After the transport experiment, Lucifer Yellow leakage was measured in a fluorescence plate reader at 485 nM excitation and 530 nM emission.

Data Analysis: All calculations were carried out using Microsoft Excel. Peak areas are determined from extracted ion chromatograms.

The apparent permeability coefficient (Papp), in units of centimeter per second, was calculated for MDCK-MDR1 drug transport assays using the following equation:

$$P_{app} = \frac{V_A}{Area \times time} \times \frac{[drug]_{acceptor}}{[drug]_{initial, donor}}$$

Where VA is the volume (in mL) in the acceptor well, Area is the surface area of the membrane (0.143 cm2 for Transwell-96 Well Permeable Supports), and time is the total transport time in seconds.

The efflux ratio was determined using the following equation:

$$\text{Efflux Ratio} = \frac{P_{app(B\,A)}}{P_{app(A\,B)}}$$

Where Papp (B-A) indicates the apparent permeability coefficient in basolateral to apical direction, and Papp (A-B) indicates the apparent permeability coefficient in apical to basolateral direction.

The recovery was determined using the following equation:

$$\text{Recovery \%} = \frac{[\text{drug}]_{acceptor} \times V_A + [\text{drug}]_{donor} \times V_D}{[\text{drug}]_{initial,donor} \times V_D} \times 100$$

Where VA is the volume (in mL) in the acceptor well (0.235 mL for Ap→Bl flux, and 0.75 mL for Bl→Ap), VD is the volume (in mL) in the donor well (0.75 mL for Ap→Bl flux, and 0.235 mL for Bl→Ap)

The leakage of Lucifer Yellow, in unit of percentage (%), was calculated using the following equation:

$$\% \, LY \text{ leakage} = 100 \times \frac{[LY]_{acceptor}}{[LY]_{donor} + [LY]_{acceptor}}$$

LY leakage of <1% is acceptable to indicate the well-qualified MDCK-MDR1 monolayer Data Analysis.

The results are shown in the table 5.

TABLE 5

Permeability Results in MDCK-MDR1 Cell Line of Exemplary Compounds

| Compound | Papp (A-B) ($10^{-6}$, cm/s) | Papp (B-A) ($10^{-6}$, cm/s) | Efflux Ratio |
|---|---|---|---|
| Compound A* | 2.75 | 37.76 | 13.72 |
| 2 | 4.95 | 14.87 | 3.00 |
| 11 | 7.38 | 6.24 | 0.85 |
| 41 | 3.63 | 4.88 | 1.35 |
| 57 | 12.36 | 18.03 | 1.46 |

*Compound A: 2-(4-((4-((1-cyclopropyl-3-(tetrahydro-2H-pyran-4-yl)-1H-pyrazol-4-yl)oxy)pyridin-2-yl)amino)pyridin-2-yl)propan-2-ol The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention.

Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A compound of Formula I-1, or a pharmaceutically acceptable salt thereof:

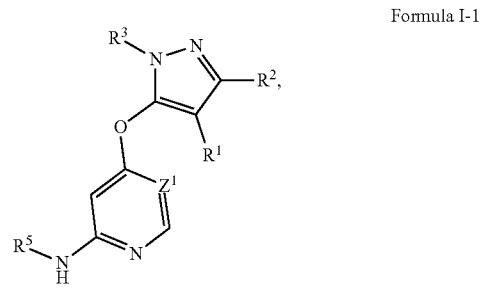

Formula I-1 wherein:

Z$^1$ is CH or N;

R$^1$ and R$^2$ are each independently hydrogen, halogen, —CN, —CO-G$^1$, —SO$_2$-G$^1$, —NR$^{10}$R$^{11}$, —O—R$^{20}$, an optionally substituted alkyl, an optionally substituted alkenyl, an optionally substituted alkynyl, an optionally substituted C$_{3-6}$ carbocyclic ring, an optionally substituted 5-8 membered heterocyclic ring, an optionally substituted phenyl, or an optionally substituted 5-10 membered heteroaryl;

or R$^1$ and R$^2$ together form an optionally substituted phenyl, an optionally substituted heteroaryl, an optionally substituted 5-8 membered carbocyclic, or an optionally substituted 5-8 membered heterocyclic ring;

R[3] is hydrogen, a nitrogen protecting group, an optionally substituted alkyl, an optionally substituted $C_{3-6}$ carbocyclic ring, an optionally substituted 5-8 membered heterocyclic ring, an optionally substituted phenyl, or an optionally substituted 5-10 membered heteroaryl;

R[5] is an optionally substituted 5-8 membered heterocyclic ring, an optionally substituted phenyl, or an optionally substituted 5-10 membered heteroaryl, wherein $G^1$ at each occurrence is independently hydrogen, $-NR^{10}R^{11}$, $-O-R^{20}$ an optionally substituted alkyl, an optionally substituted alkenyl, an optionally substituted alkynyl, an optionally substituted $C_{3-6}$ carbocyclic ring, an optionally substituted 5-8 membered heterocyclic ring, an optionally substituted phenyl, or an optionally substituted 5-10 membered heteroaryl;

wherein each of $R^{10}$ and $R^{11}$ at each occurrence is independently hydrogen, a nitrogen protecting group, an optionally substituted alkyl, an optionally substituted alkenyl, an optionally substituted alkynyl, an optionally substituted $C_{3-6}$ carbocyclic ring, an optionally substituted 5-8 membered heterocyclic ring, an optionally substituted phenyl, or an optionally substituted 5-10 membered heteroaryl; or $R^{10}$ and $R^{11}$ together form an optionally substituted 5-7 membered heterocyclic or an optionally substituted 5-10 membered heteroaryl; and wherein $R^{20}$ at each occurrence is independently hydrogen, an oxygen protecting group, an optionally substituted alkyl, an optionally substituted alkenyl, an optionally substituted alkynyl, an optionally substituted $C_{3-6}$ carbocyclic ring, an optionally substituted 5-8 membered heterocyclic ring, an optionally substituted phenyl, or an optionally substituted 5-10 membered heteroaryl.

2. The compound of claim 1, or a pharmaceutically acceptable salt thereof, characterized as having Formula I-2:

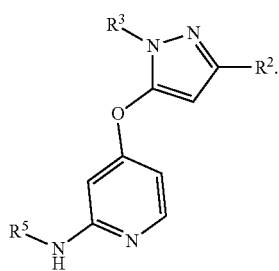

Formula I-2

3. The compound of claim 1, or a pharmaceutically acceptable salt thereof, wherein $R^2$ is selected from halogen, an optionally substituted $C_{1-4}$ alkyl, an optionally substituted $C_{3-6}$ cycloalkyl, an optionally substituted 4-8 membered heterocyclyl, an optionally substituted $C_{1-4}$ alkoxy, an optionally substituted $C_{3-6}$ cycloalkoxy, an optionally substituted phenyl, and an optionally substituted 5 or 6 membered heteroaryl.

4. The compound of claim 3, or a pharmaceutically acceptable salt thereof, wherein the optionally substituted $C_{1-4}$ alkyl, $C_{3-6}$ cycloalkyl, 4-8 membered heterocyclyl, $C_{1-4}$ alkoxy or $C_{3-6}$ cycloalkoxy is optionally substituted with 1-3 substituents independently selected from F, $C_{1-4}$ alkyl, and $C_{1-4}$ alkoxy; and wherein the optionally substituted phenyl, or 5 or 6 membered heteroaryl is optionally substituted with 1-3 substituents independently selected from halogen, —CN, $C_{1-4}$ alkyl, fluorine substituted $C_{1-4}$ alkyl, $C_{1-4}$ alkoxy, and fluorine substituted $C_{1-4}$ alkoxy.

5. The compound of claim 1, or a pharmaceutically acceptable salt thereof, wherein $R^2$ is selected from methyl, ethyl, isopropyl, methoxy, $-CHF_2$, $-CF_3$, cyclopropyl, cyclobutyl, cyclopentyl, $-CH_2-CHF_2$ and $-CH_2-CF_3$.

6. The compound of claim 1, or a pharmaceutically acceptable salt thereof, wherein $R^3$ is selected from an optionally substituted $C_{1-4}$ alkyl, an optionally substituted $C_{3-6}$ cycloalkyl, an optionally substituted 4-8 membered heterocyclyl, an optionally substituted phenyl, and an optionally substituted 5 or 6 membered heteroaryl.

7. The compound of claim 1, or a pharmaceutically acceptable salt thereof, wherein $R^3$ is methyl, ethyl, isopropyl, tert-butyl, $-CHF_2$, $-CF_3$, $-CH_2-CHF_2$, $-CH_2-CF_3$,

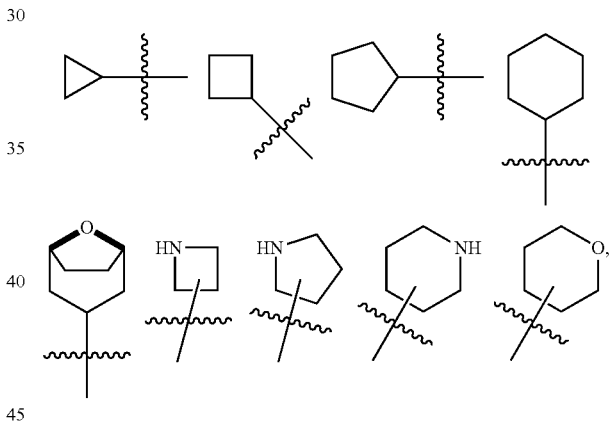

8. The compound of claim 1, or a pharmaceutically acceptable salt thereof, wherein $R^3$ is selected from

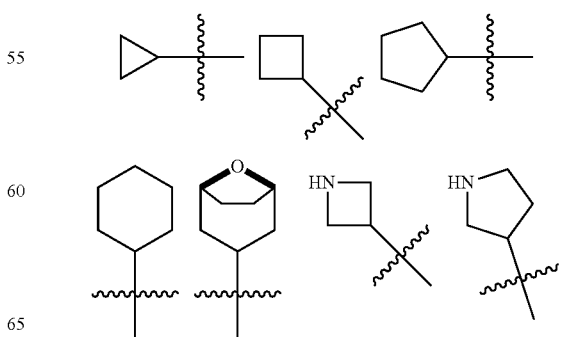

each of which is optionally substituted with 1 or 2 substituents independently selected from F and methyl.

9. The compound of claim 1, or a pharmaceutically acceptable salt thereof, wherein $R^3$ is selected from -continued

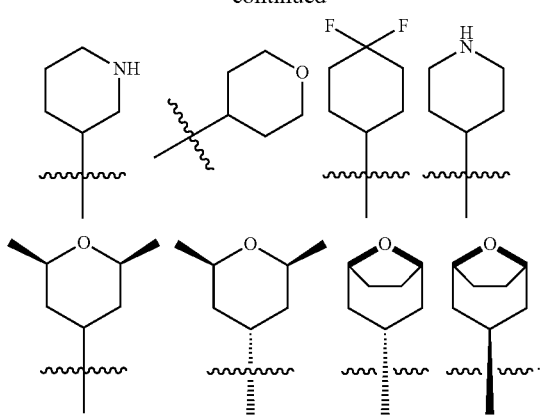

10. The compound of claim 1, or a pharmaceutically acceptable salt thereof, wherein $R^3$ is selected from

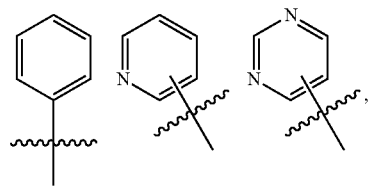

each of which is optionally substituted with 1 or 2 substituents independently selected from F, Cl, methyl, and CN.

11. The compound of claim 1, or a pharmaceutically acceptable salt thereof, wherein $R^3$ is selected from

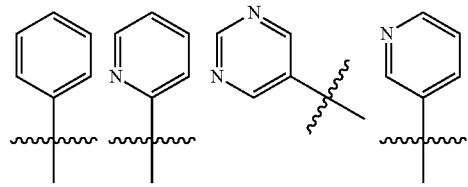

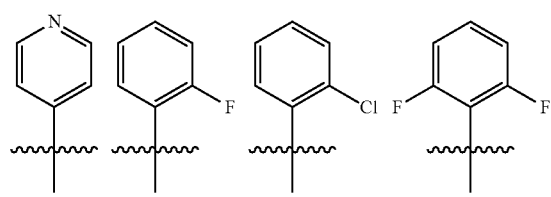

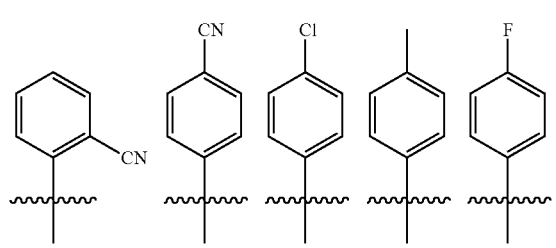

-continued

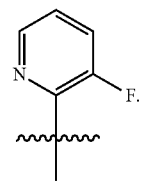

12. The compound of claim 1, or a pharmaceutically acceptable salt thereof, wherein $R^5$ is selected from:

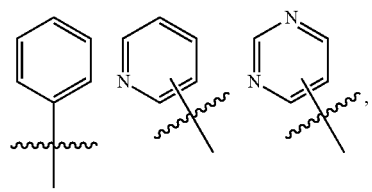

each of which is substituted with one substituent selected from

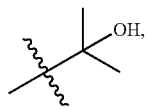 [SMILES: *C(C)(C)O]

—CONH$_2$, and

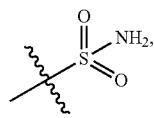 [SMILES: *S(N)(=O)=O]

and further optionally substituted.

13. The compound of claim 1, or a pharmaceutically acceptable salt thereof, wherein $R^5$ is selected from:

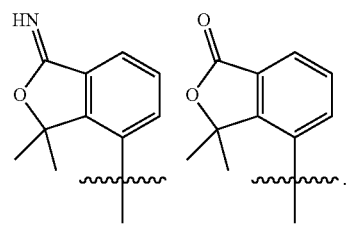

14. The compound of claim 1, or a pharmaceutically acceptable salt thereof, characterized as having Formula I-3, I-4, or I-5:

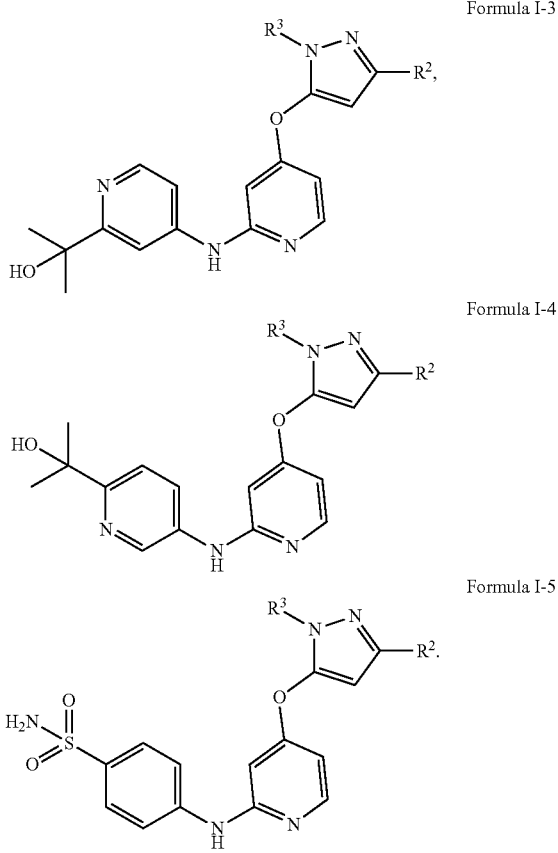

Formula I-3

Formula I-4

Formula I-5

15. A compound of Formula II, or a pharmaceutically acceptable salt thereof:

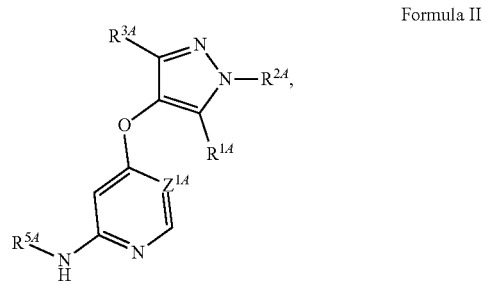

Formula II wherein:
$R^{14}$ is hydrogen, halogen, or an optionally substituted $C_{1-4}$ alkyl,
$R^{24}$ is —$CH_2CF_3$, or $C_{4-6}$ cycloalkyl, wherein the $C_{4-6}$ cycloalkyl is optionally substituted with 1-3 substituents independently selected from fluorine and methyl; or $R^{14}$ and $R^{24}$ together form an optionally substituted heteroaryl, or an optionally substituted 5-8 membered heterocyclic ring;
$R^{34}$ is hydrogen, halogen, —CN, —CO-$G^1$, —$SO_2$-$G^1$, —$NR^{10}R^{11}$, —O—$R^{20}$, an optionally substituted alkyl, an optionally substituted alkenyl, an optionally substituted alkynyl, an optionally substituted $C_{3-6}$ carbocyclic ring, an optionally substituted 5-8 membered heterocyclic ring, an optionally substituted phenyl, or an optionally substituted 5-10 membered heteroaryl;
$Z^{14}$ is N or CH,
$R^{54}$ is hydrogen, a nitrogen protecting group, an optionally substituted alkyl, an optionally substituted $C_{3-6}$ carbocyclic ring, an optionally substituted 5-8 membered heterocyclic ring, an optionally substituted phenyl, or an optionally substituted 5-10 membered heteroaryl;
wherein $G^1$ at each occurrence is independently hydrogen, —$NR^{10}R^{11}$, —O—$R^{20}$ an optionally substituted alkyl, an optionally substituted alkenyl, an optionally substituted alkynyl, an optionally substituted $C_{3-6}$ carbocyclic ring, an optionally substituted 5-8 membered heterocyclic ring, an optionally substituted phenyl, or an optionally substituted 5-10 membered heteroaryl;
wherein each of $R^{10}$ and $R^{11}$ at each occurrence is independently hydrogen, a nitrogen protecting group, an optionally substituted alkyl, an optionally substituted alkenyl, an optionally substituted alkynyl, an optionally substituted $C_{3-6}$ carbocyclic ring, an optionally substituted 5-8 membered heterocyclic ring, an optionally substituted phenyl, or an optionally substituted 5-10 membered heteroaryl; or $R^{10}$ and $R^{11}$ together form an optionally substituted 5-7 membered heterocyclic or an optionally substituted 5-10 membered heteroaryl; and
wherein $R^{20}$ at each occurrence is independently hydrogen, an oxygen protecting group, an optionally substituted alkyl, an optionally substituted alkenyl, an optionally substituted alkynyl, an optionally substituted $C_{3-6}$ carbocyclic ring, an optionally substituted 5-8 membered heterocyclic ring, an optionally substituted phenyl, or an optionally substituted 5-10 membered heteroaryl.

16. A pharmaceutical composition comprising the compound of claim 1, or a pharmaceutically acceptable salt thereof, and optionally a pharmaceutically acceptable excipient or carrier.

17. A method of treating cancer, fibrosis, or an immune related disease in a subject in need thereof, comprising administering to the subject a therapeutically effective amount of the compound of claim 1 or a pharmaceutical salt thereof.

18. A method of inhibiting TGF-beta signaling in a subject in need thereof, comprising administering to the subject an effective amount of the compound of claim 1 or a pharmaceutical salt thereof.

19. The compound of claim 1, or a pharmaceutically acceptable salt thereof, wherein the compound is selected from:

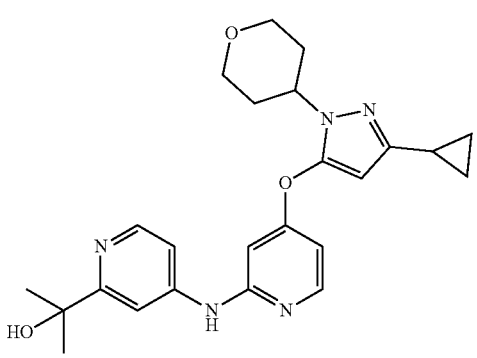

1

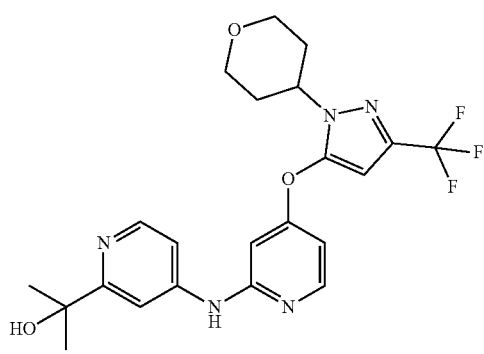
2
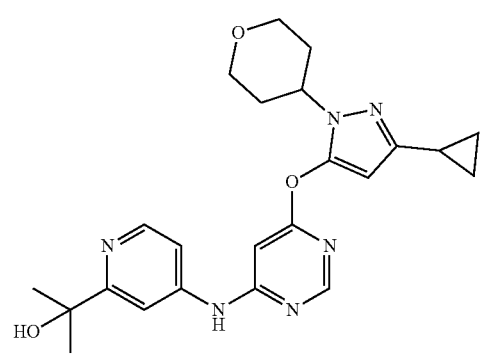
3
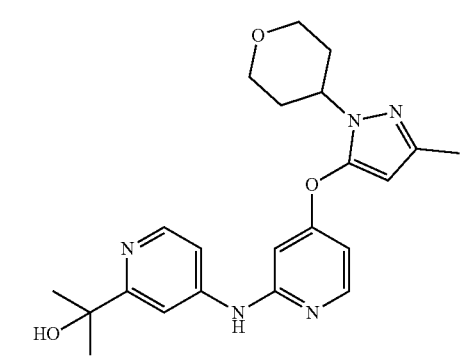
4
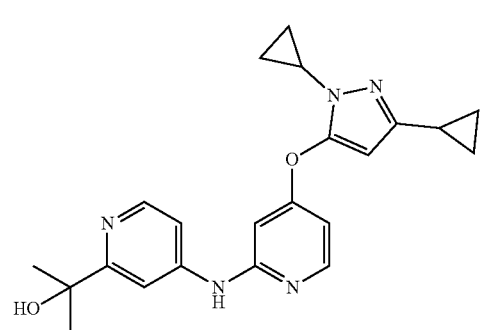
5
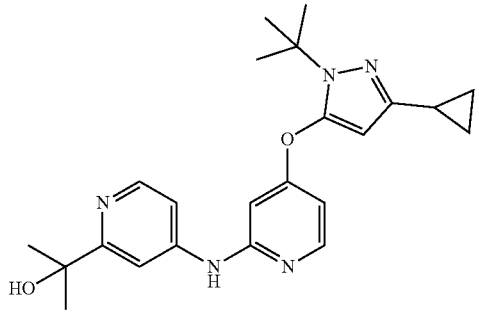
6
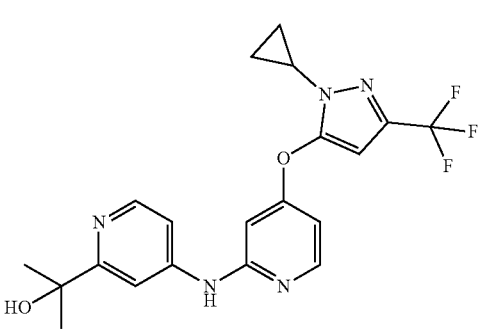
7
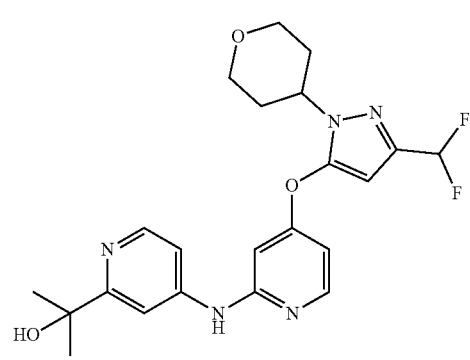
8
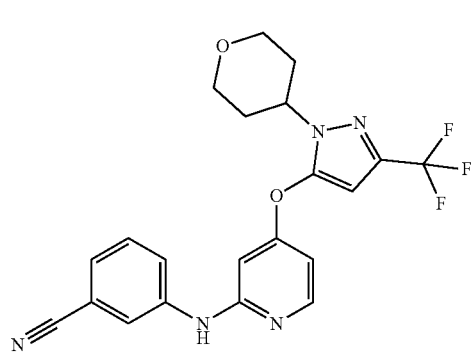
9
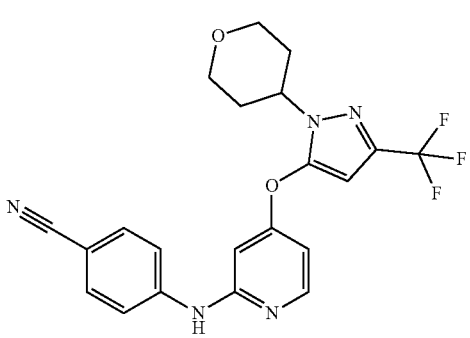
10

11
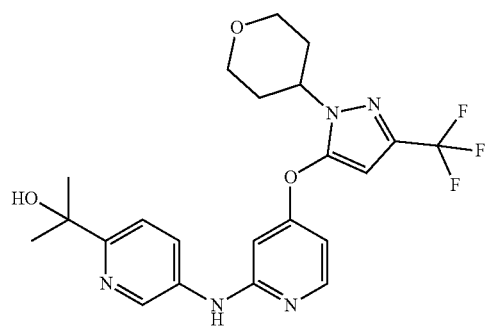
12
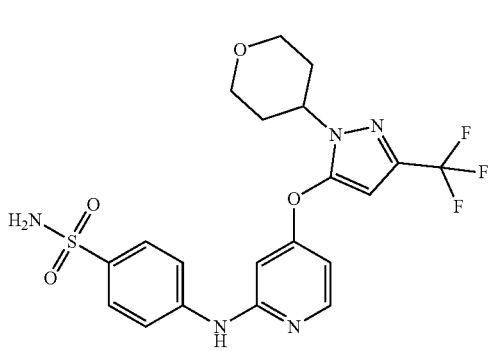
13
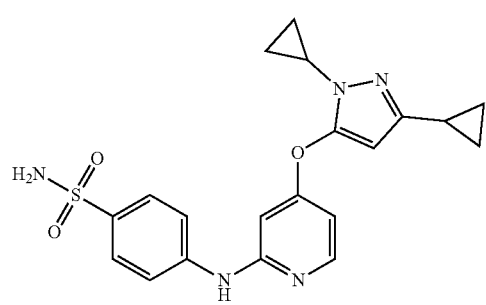
14
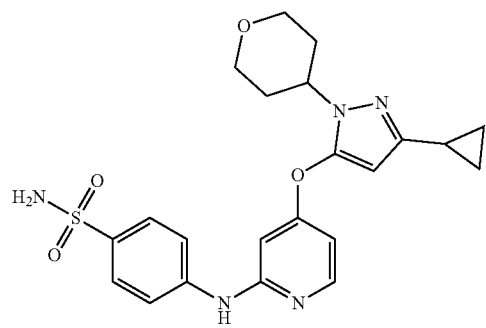
15
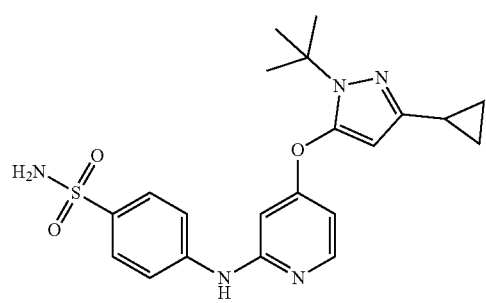
16
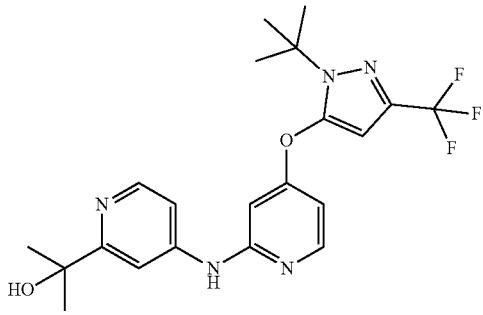
17
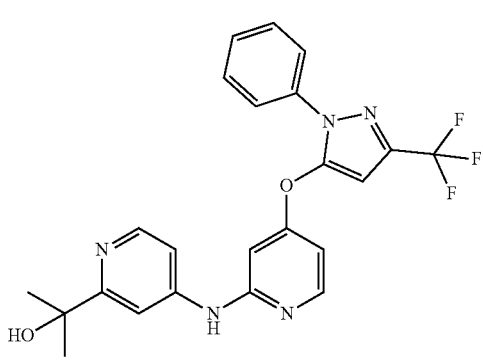
18
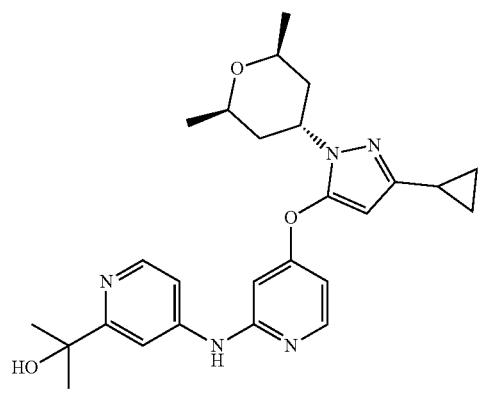
19
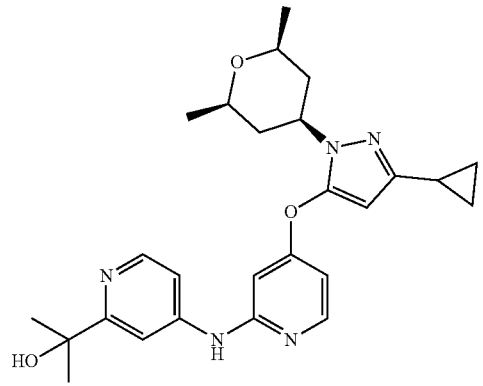

20
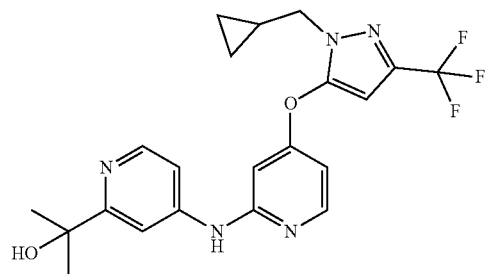
21
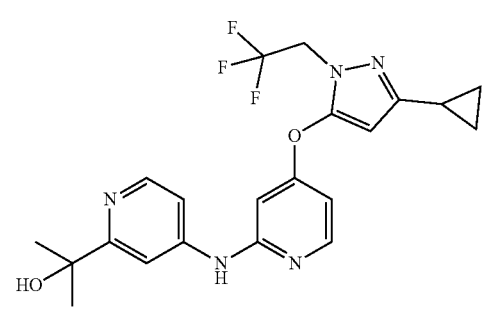
22
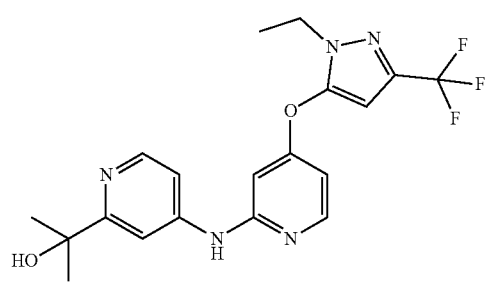
23
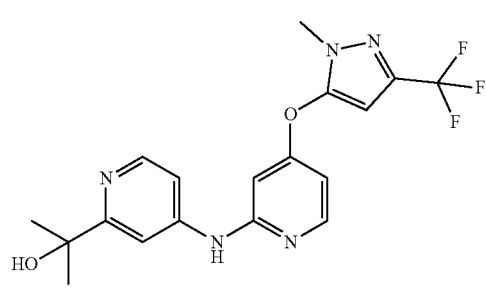
24
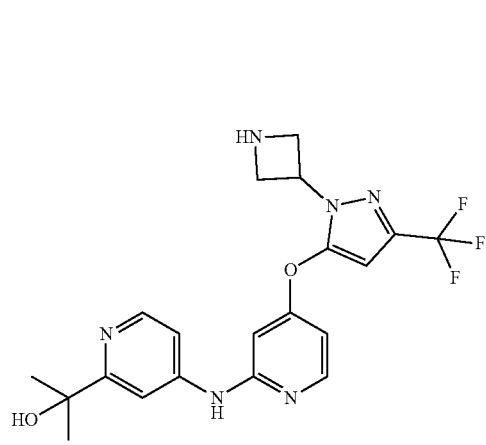
25
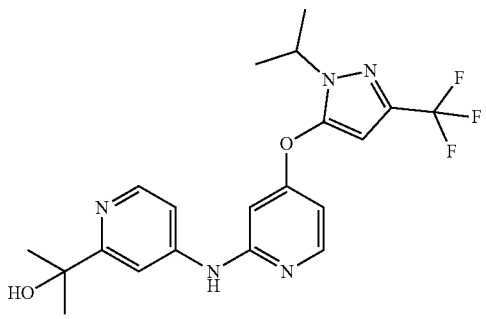
26
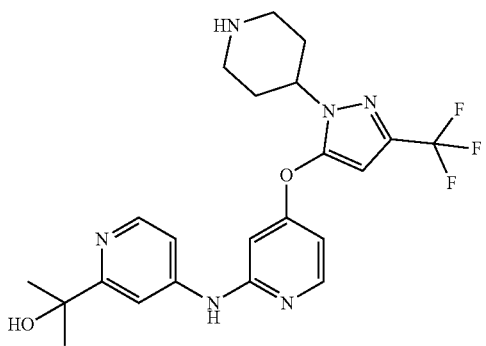
27
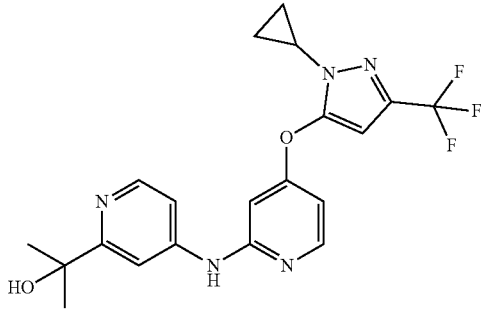
28
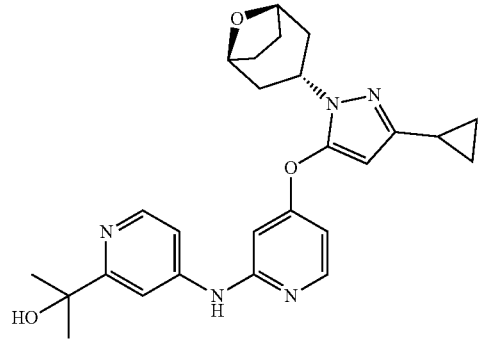

29
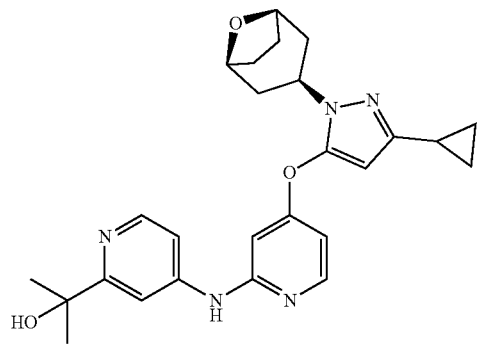
30
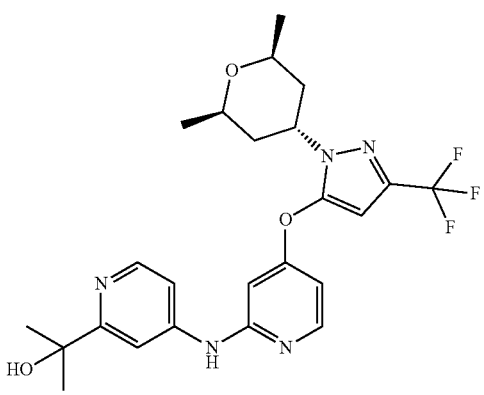
31
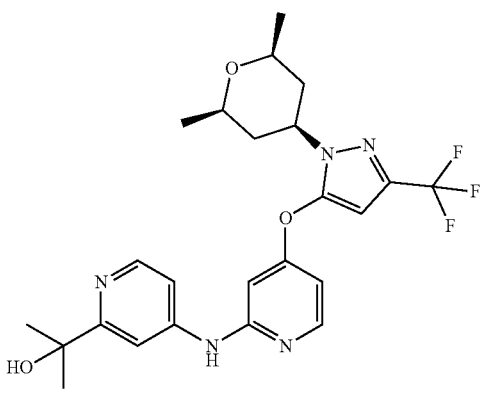
32
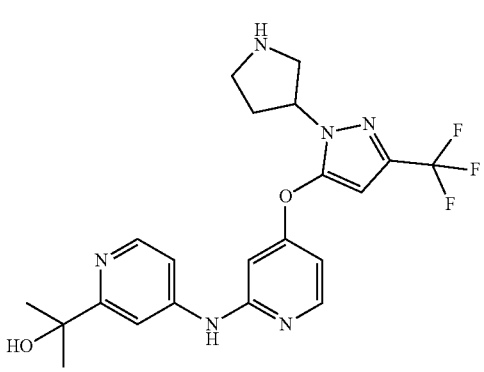
33
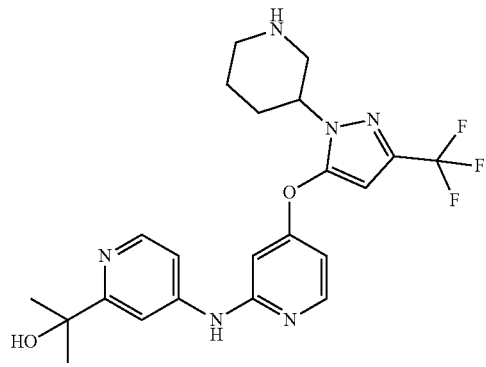
34
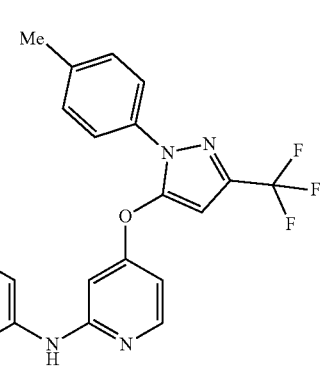
35
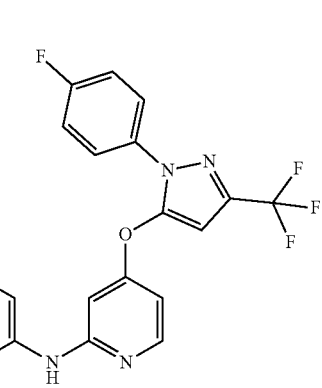
36
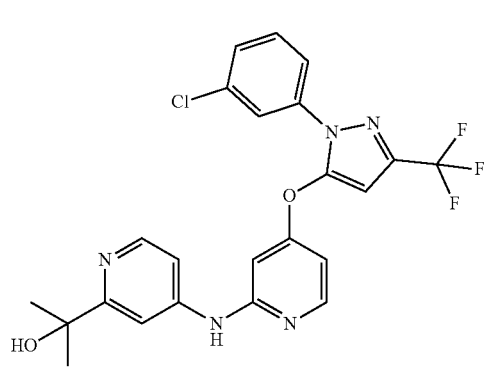

37
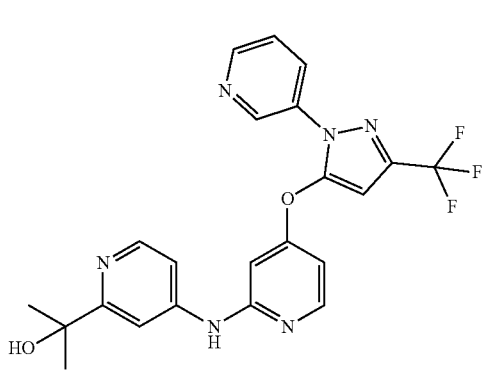
38
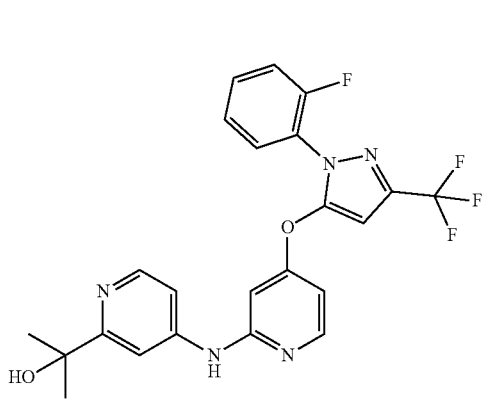
39
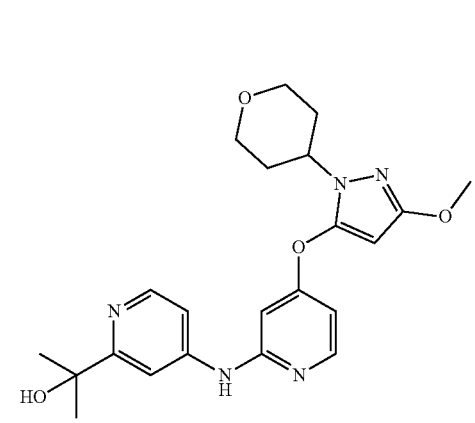
40
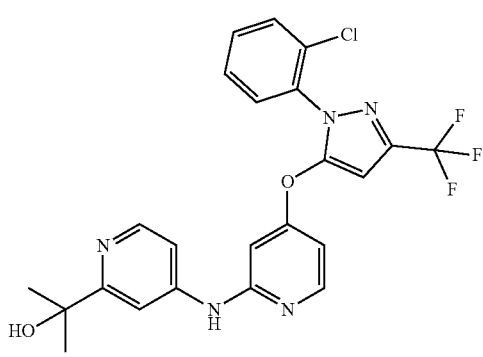
41
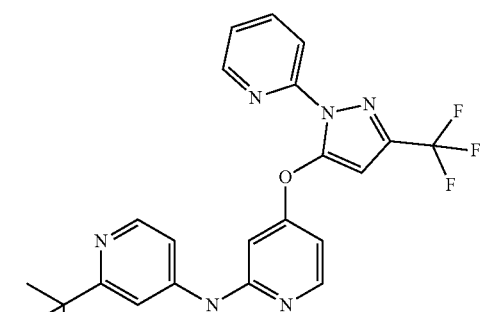
42
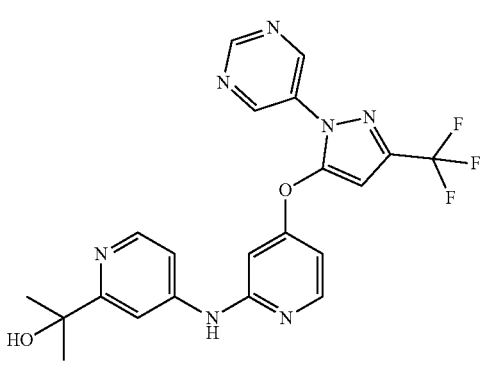
43
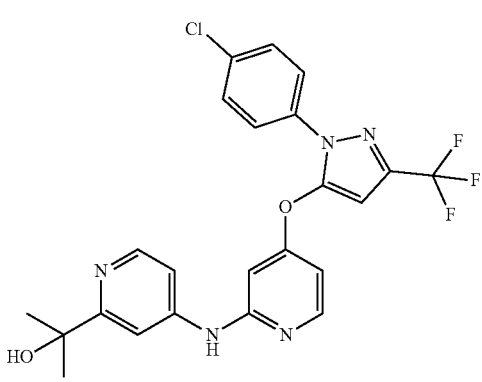
44
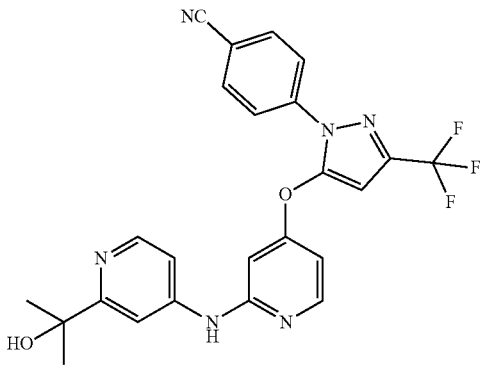

45
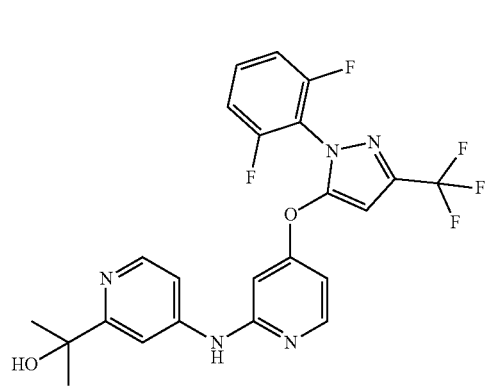
46
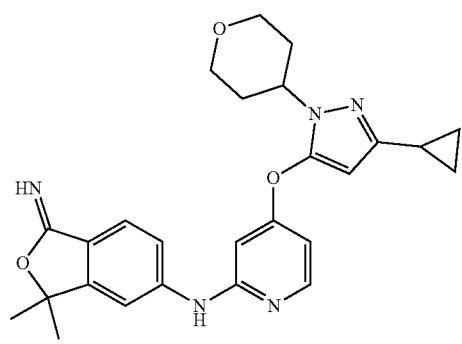
47
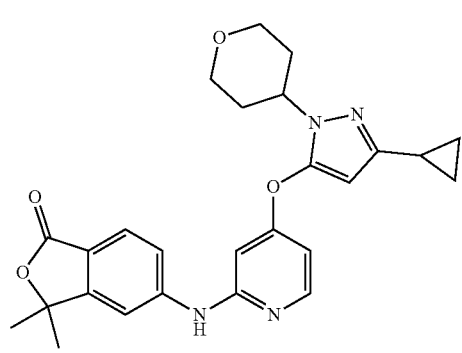
48
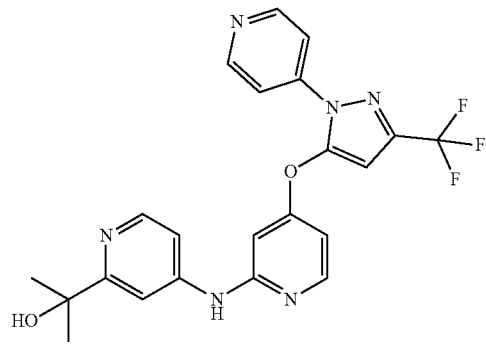
49
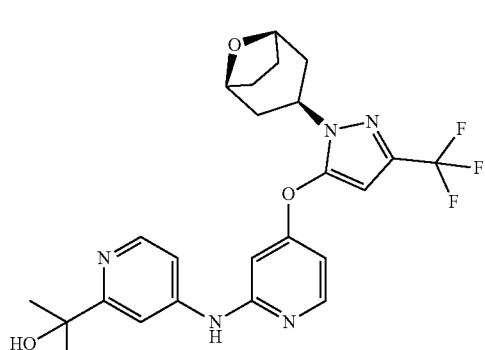
50
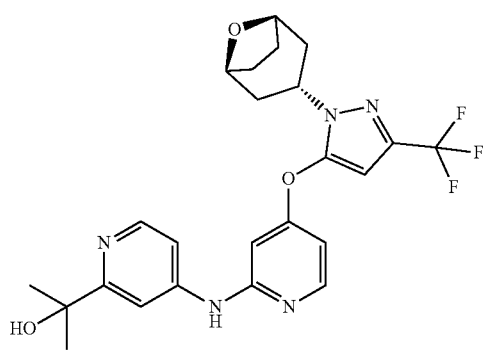
51
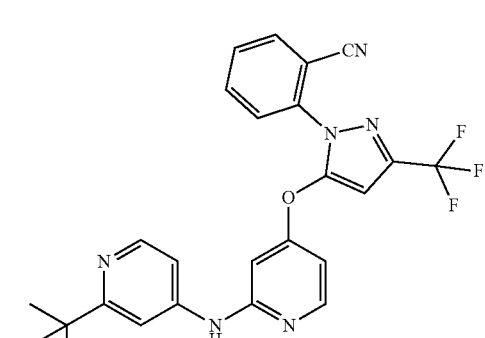
52
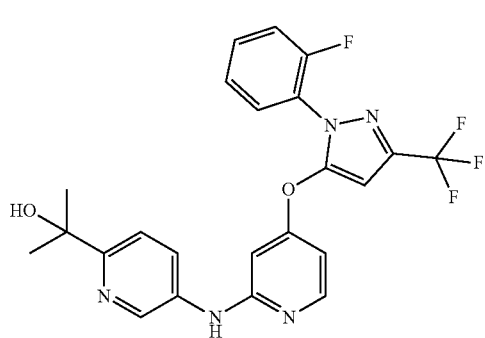

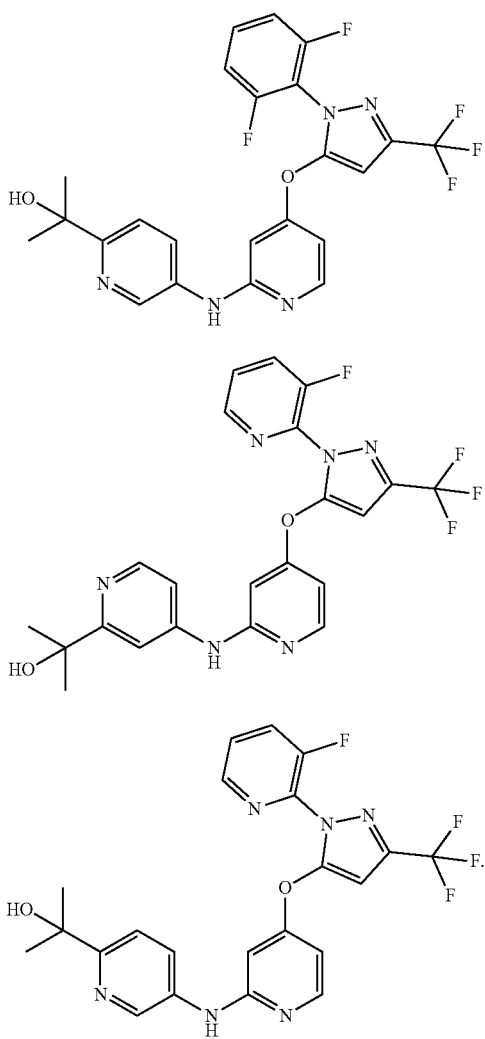

20. The compound of claim 14, or a pharmaceutically acceptable salt thereof, wherein $R^2$ is selected from methyl, ethyl, isopropyl, methoxy, —$CHF_2$, —$CF_3$, cyclopropyl, cyclobutyl, cyclopentyl, —$CH_2$—$CHF_2$ and —$CH_2$—$CF_3$.

21. The compound of claim 20, or a pharmaceutically acceptable salt thereof, wherein $R^3$ is methyl, ethyl, isopropyl, tert-butyl, —$CHF_2$, —$CF_3$, —$CH_2$—$CHF_2$, —$CH_2$—$CF_3$,

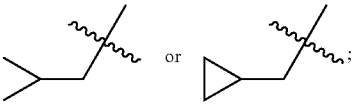

or $R^3$ is selected from

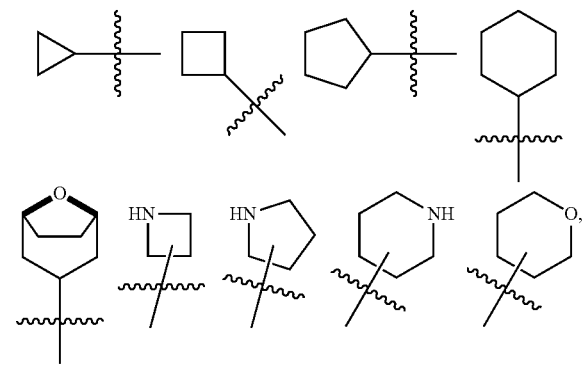

each of which is optionally substituted with 1 or 2 substituents independently selected from F and methyl; or $R^3$ is selected from

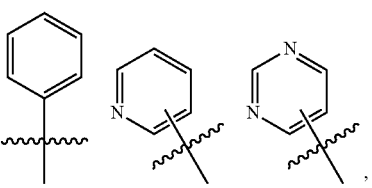

each of which is optionally substituted with 1 or 2 substituents independently selected from F, Cl, methyl, and CN.

* * * * *